US011453674B2

(12) United States Patent
Wu et al.

(10) Patent No.: US 11,453,674 B2
(45) Date of Patent: Sep. 27, 2022

(54) HETEROCYCLIC COMPOUND, PREPARATION METHOD AND USE THEREOF IN MEDICINE

(71) Applicant: SUZHOU SINOVENT PHARMACEUTICALS CO., LTD., Suzhou (CN)

(72) Inventors: Yuchuan Wu, Beijing (CN); Xi Chen, Beijing (CN); Shaoqiang Huang, Beijing (CN); Yonghan Hu, Beijing (CN); Linhai Qu, Beijing (CN); Jinlian Zhu, Beijing (CN); Xiao Liu, Beijing (CN)

(73) Assignee: EVOPOINT BIOSCIENCES CO., LTD., Suzhou (CN)

( * ) Notice: Subject to any disclaimer, the term of this patent is extended or adjusted under 35 U.S.C. 154(b) by 0 days.

(21) Appl. No.: 16/963,020

(22) PCT Filed: Jan. 18, 2019

(86) PCT No.: PCT/CN2019/072419
§ 371 (c)(1),
(2) Date: Jul. 17, 2020

(87) PCT Pub. No.: WO2019/141259
PCT Pub. Date: Jul. 25, 2019

(65) Prior Publication Data
US 2020/0347070 A1 Nov. 5, 2020

(51) Int. Cl.
C07D 487/04 (2006.01)
C07D 231/56 (2006.01)
C07D 401/12 (2006.01)
C07D 471/04 (2006.01)
C07D 491/048 (2006.01)

(52) U.S. Cl.
CPC ......... C07D 487/04 (2013.01); C07D 231/56 (2013.01); C07D 401/12 (2013.01); C07D 471/04 (2013.01); C07D 491/048 (2013.01)

(58) Field of Classification Search
None
See application file for complete search history.

(56) References Cited

U.S. PATENT DOCUMENTS

| 4,400,387 A | 8/1983 | Rosseels et al. |
| 2005/0267108 A1 | 12/2005 | Hsieh et al. |
| 2009/0142832 A1 | 6/2009 | Dalton et al. |
| 2018/0282321 A1 | 10/2018 | Shi et al. |

FOREIGN PATENT DOCUMENTS

| CA | 2998034 A1 | 3/2017 | |
| CA | 3043942 A1 | 5/2018 | |
| CN | 106045898 A | 10/2016 | |
| CN | 106432229 A | 2/2017 | |
| CN | 108084186 A | 5/2018 | |
| CN | 108727267 A | 11/2018 | |
| EP | 0061380 A1 * | 9/1982 | ........... C07D 487/04 |
| EP | 0149419 A1 | 7/1985 | |
| EP | 3543240 A1 | 9/2019 | |
| JP | 2018526417 A | 9/2018 | |
| JP | 2021510719 A | 4/2021 | |
| WO | WO-200605006 A2 | 1/2006 | |
| WO | WO-2010057121 A1 | 5/2010 | |
| WO | WO-2012048058 A2 | 4/2012 | |

(Continued)

OTHER PUBLICATIONS

Machine translation of EP 0061380.*

(Continued)

Primary Examiner — Heidi Reese
(74) Attorney, Agent, or Firm — Marshall, Gerstein & Borun LLP

(57) ABSTRACT

Provided are a heterocyclic compound, a preparation method and the use thereof in medicine, and particularly involved are a heterocyclic compound for preventing and/or treating hypernricemia and gout, a preparation method and the use thereof in medicine. In particular, provided are a compound as shown in formula (I) and/or formula (II) or a tautomer thereof and a pharmaceutically acceptable salt thereof, a preparation method therefor and a method and the use thereof for treating hypernricemia and gout.

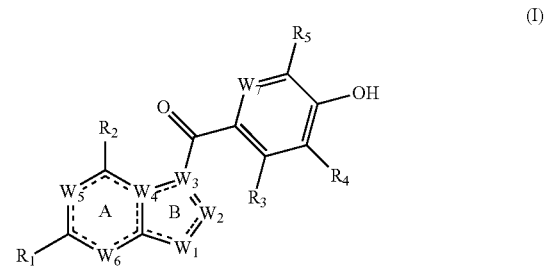

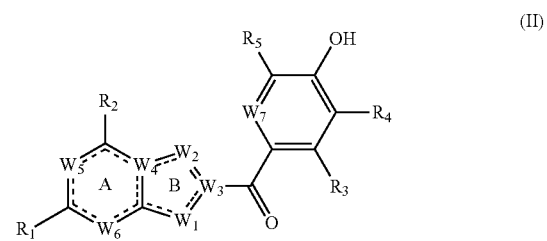

3 Claims, No Drawings

(56) References Cited

FOREIGN PATENT DOCUMENTS

WO  WO-2013112878 A1  8/2013
WO  WO-2018090921 A1  5/2018

OTHER PUBLICATIONS

Sanfilippo, P. et al., J. Med. ChSanfilippo, P. et al., J. Med. Chem., 1988, vol. 31, pp. 2221-2227em., 1988, vol. 31, pp. 2221-2227.*
CAPLUS Accession No. 1988:570365.*
Extended European Search Report for Application No. EP 19741276.0, dated Nov. 10. 2021.
Jie Fu et al., "Discovery of 1 H-benzo d[ 1,2,3]triazol-1-yl 3,4,5-trimethoxybenzoate as a potential antiproliferative agent by inhibiting histone deacetylase", *Bioorganic & Medicinal Chemistry*, vol. 18, pp. 8457-8462 (2010).
M.F. Wempe et al., "Human Uric Acid Transporter 1 (hURAT1): An Inhibitor Structure-Activity Relationship (SAR) Study", *Nucleosides, Nucleotides and Nucleic Aads*, vol. 30, pp. 1312-1323 (2011).
Hao Yang et al., "Synthesis and in vitro characterization of cinnoline and benzimidazole analogues as phosphodiesterase 10A inhibitors", *Bioorganic & Medicinal Chemistry Letters*, vol. 25, No. 4, pp. 919-924 (2015).
Oliver R. Thiel et al., "Addressing Process Safety Hazards: Replacement of para-Methoxybenzyl Chloride Leads to a Safer and Shorter Route", *American Chemical Society*, vol. 1181, pp. 269-282 (2014).
Database Registry, Chemical Abstracts Service, "benzimidazole compounds", retrieved from STN Database accession No. 1788832-61-0/RN, Jun. 25, 2015.
International Search Report and Written Opinion for PCT/CN2019/072419, dated Mar. 27, 2019.
STN. "Registry", RN: 918511-73-k 870557-88-3; 14145-68-3; 102021-88-5; 15815-29-9; 885694-11-1; 1788832-61-0; 1787965-90-5; 126521-89-0; 457943-27-0; 448198-66-1; 748087-11-8; 115407-41-5; 115407-40-4; 84855-10-7 (Jun. 25, 2015).

* cited by examiner

HETEROCYCLIC COMPOUND, PREPARATION METHOD AND USE THEREOF IN MEDICINE

TECHNICAL FIELD

The present invention relates to a pharmaceutical for preventing and/or treating hyperuricemia and gout, in particular to a human uric acid transporter (hURAT1) inhibitor, a preparation method thereof, a pharmaceutical composition comprising the same, and use thereof.

BACKGROUND OF THE INVENTION

Gout is a group of heterogeneous metabolic diseases that result from the deposition of urate in joints and soft tissues due to a long period of hyperuricemia. The normal concentration of blood uric acid is 150-380 μmol/L in males and 100-300 μmol/L in females before menopause. As for postmenopausal females, the concentration of blood uric acid is close to that of males. The saturated concentration of serum uric acid at 37° C. is about 416 μmol/L, and hyperuricemia occurs when the concentration is greater than this value. Hyperuricemia is the biochemical basis of gout.

The incidence of gout in the general population is 1-2%. Currently, there are tens of millions of gout patients worldwide. In China, with the improvement of people's living standard and the change of the dietary in recent years, the incidence of gout is increasing year by year, and the prevalence of gout reached 1.1% in general population by 2008 (The Journal of Foot and Ankle Surgery, 48(1):70-73).

At present, pharmaceuticals for treating hyperuricemia and gout mainly include: anti-inflammatory analgesics such as non-steroidal anti-inflammatory drugs (NSAIDs) for controlling symptoms such as joint swelling and pain during acute gouty arthritis; uricopoiesis-inhibiting drugs such as xanthine oxidase inhibitors (febuxostat); uricosurics such as probenecid and benzbromarone; and uricolytic drugs such as uricase for rapidly decomposing blood uric acid during acute gouty arthritis. Among them, uricosurics play a very important role in treating hyperuricemia and gout. The mechanism of action for such drugs is inhibiting the active reabsorption of urate in proximal convoluted tubules and promoting the excretion of urate in urine by inhibiting uric acid transporter 1 (hURAT1) on the brush-border membrane of epithelial cells of the proximal convoluted tubules of kidney, thereby reducing the blood uric acid concentration of and controlling the gout attack. Such drugs mainly include probenecid, benzbromarone and the like. However, uricosurics have serious side effects, for example, benzbromarone has hepatotoxicity and risks of causing fulminant hepatitis. It has been reported that benzbromarone is oxidized in vivo to generate two metabolites with o-benzoquinone structures, which is the direct cause of benzbromarone-induced hepatotoxicity (Chem. Res. Toxicol., 2007, 20(12):1833-1842). Specifically, benzbromarone is oxidized in the human body by CYP2C9 to generate 6-hydroxybenzbromarone, followed by two metabolic pathways: in one pathway, 6-hydroxybenzbromarone is oxidized by CYP2C9 to generate 5,6-dihydroxybenzbromarone, which is further oxidized to generate an o-benzoquinone type metabolite; in the other pathway, 6-hydroxybenzbromarone is oxidized by CYP2C9 to generate 6,7-dihydroxybenzbromarone (or 4,6-dihydroxybenzbromarone), which is further oxidized by other P450s enzymes to generate another o-benzoquinone type metabolite.

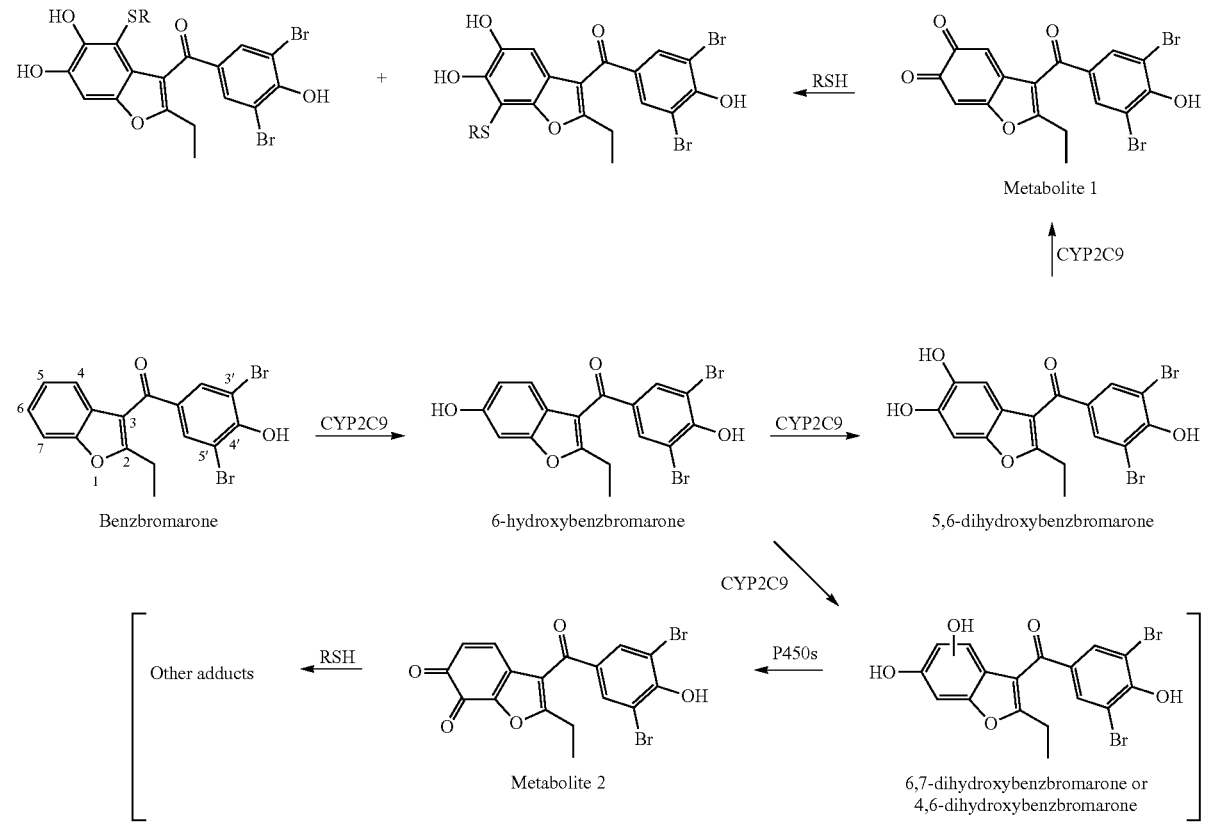

The two o-benzoquinone-like metabolites are chemically active and may undergo conjugate addition with sulfhydryl on cysteine residues of a protein or a polypeptide, thus changing the spatial structure of the protein or the polypeptide, causing denaturation/inactivation of the protein or polypeptide.

Furthermore, it has been reported that benzbromarone undergoes ipso-substitution metabolism in vivo to generate metabolites 2,6-dibromohydroquinone (DBH) and 2,6-dibromobenzoquinone (DBBQ), in the liver (Novel Bioactuation Pathway of Benzbromone meditated by Cytochrome P450, Yuma Kitagawa et al., Drug Metab Dispos 43:1303-1306, September 2015). The two metabolites have strong toxicity on liver, and are also one of the causes of benzbromarone-induced hepatotoxicity.

Based on the above-mentioned mechanism of toxicity, in order to avoid side effects caused by toxic metabolites of benzbromarone and to maintain the uricosuric activity of benzbromarone, efforts on modifying the structure of benzbromarone were made to interfere with or reduce the production of metabolites of benzbromarone, and a series of efficient and low-toxicity uricosurics were developed for preventing and treating hyperuricemia and gout. See, WO2012/048058A2, CN106432229A, WO2009/145456A2, CN106045898A, CN102718735B, etc. However, no satisfactory results have been obtained until now. Therefore, at present, there is still an urgent need for uricosurics with good efficacy and mild toxicity in clinic.

SUMMARY OF THE INVENTION

The present invention is intended to provide a human uric acid transporter (hURAT1) inhibitor, which has highly selective uricosuric activity and significantly reduced toxicity on liver.

For the purpose described above, in one aspect, the present invention provides a compound of formula (I) and/or formula (II), or a tautomer thereof and a pharmaceutically acceptable salt thereof,

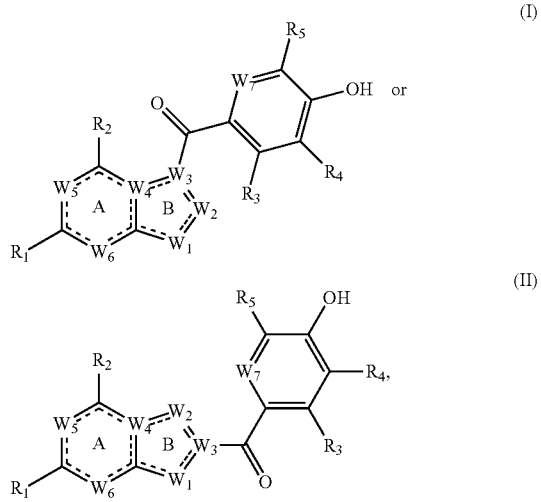

wherein, ring A is a six-membered aromatic or heteroaromatic ring and ring B is a five-membered heteroaromatic ring, $W_1$ is selected from N and O;
$W_2$ is selected from $CR_6$ and $NR_7$;
$W_3$ and $W_4$ are each independently selected from C and N;
$W_5$, $W_6$ and $W_7$ are each independently selected from $CR_8$ and N;
$R_1$, $R_2$, $R_3$, $R_4$, $R_5$, $R_6$, $R_7$ and $R_8$ are each independently selected from hydrogen, deuterium, halogen, cyano, hydroxy, $C_{1-20}$ alkyl, $C_{1-20}$ alkoxy, and $C_{1-20}$ haloalkyl;
provided that the following are excluded:
when $W_1$ is selected from O, $W_2$, $W_3$, $W_4$, $W_5$, $W_6$, and $W_7$ are $CR_6$;
when $W_1$ and $W_4$ are selected from N, $W_2$ is $CR_6$, $W_3$ is C, and $W_5$, $W_6$, and $W_7$ are $CR_8$.

In another aspect, the present invention provides a method for preparing a compound of formula (Ia) and/or formula (Ib) or a tautomer thereof and a pharmaceutically acceptable salt thereof.

In yet another aspect, the present invention provides a pharmaceutical composition for preventing or treating hypemricemia and gout, which comprises the compound of formula (Ia) and/or formula (Ib) or the tautomer thereof or the pharmaceutically acceptable salt thereof.

In still another aspect, the present invention provides a method for treating hyperuricemia and gout, comprising administering to an individual with hyperuricemia or gout the compound of formula (Ia) and/or formula (Ib) or the tautomer thereof and the pharmaceutically acceptable salt thereof, or the pharmaceutical composition comprising the compound of formula (Ia) and/or formula (Ib) or the tautomer thereof or the pharmaceutically acceptable salt thereof described herein.

DETAILED DESCRIPTION

Definitions

As used herein, the term "alkyl" refers to linear or branched, saturated hydrocarbyl having 1 to 20 carbon atoms. Preferably, the alkyl is an alkyl having 1 to 12 carbon atoms. More preferably, the alkyl is an alkyl having 1 to 6 carbon atoms. Most preferably, the alkyl is an alkyl having 1 to 4 carbon atoms. Examples of alkyl include, but are not limited to, methyl, ethyl, 1-propyl (n-propyl), 2-propyl (isopropyl), 1-butyl (n-butyl), 2-methyl-1-propyl (isobutyl), 2-butyl (sec-butyl), 2-methyl-2-propyl (tert-butyl), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, 1-nonyl, 1-decyl, and the like.

As used herein, the term "halogen" refers to fluorine, chlorine, bromine, and iodine.

As used herein, the term "alkoxy" refers to "—O-alkyl", wherein alkyl is defined above.

As used herein, the term "haloalkyl" refers to an alkyl substituted with one or more halogens, wherein the halogens and alkyl are as defined above.

As used herein, the term "tautomer" refers to isomers of a compound that differ from each other in proton position and/or electron distribution. Proton tautomers and valence tautomers are described, and it is understood that more than two tautomers may exist for a given compound. Examples of tautomers include, but are not limited to, tautomeric forms of heteroaryl containing ring atoms linked to a ring-NH-moiety and a ring=N-moiety, and the ring-NH-moiety and the ring=N-moiety are present, for example, in pyrazoles, imidazoles, benzimidazoles, triazoles and tetrazoles (see, e.g., Smith, March's Advanced Organic Chemistry (5th edition), page 1218-1223, Wiley-Interscience, 2001; Katritzky A. and Elguero J., et. al., The Tautomer of Heterocycles, Academic Press (1976)).

As used herein, the term "pharmaceutically acceptable salt" refers to a salt of a compound that is pharmaceutically acceptable and possesses desired pharmacological activities (or can be converted to a form that possesses the activities) of the parent compound. Such salts include acid addition salts formed with inorganic acids such as hydrochloric acid, hydrobromic acid, sulfuric acid, nitric acid, phosphoric acid, and the like, or with organic acids such as acetic acid, trifluoroacetic acid, benzenesulfonic acid, benzoic acid, (1R)-(−)-10-camphorsulfonic acid, citric acid, ethanesulfonic acid, fumaric acid, glucoheptonic acid, gluconic acid, lactic acid, maleic acid, malonic acid, mandelic acid, methanesulfonic acid, 2-naphthalenesulfonic acid, oleic acid, palmitic acid, propionic acid, stearic acid, succinic acid, tartaric acid, p-toluenesulfonic acid, trimethylacetic acid, and the like; and salts formed when an acidic proton in the parent compound is a metal ion, e.g., an alkali metal ion (such as sodium or potassium), an alkaline earth metal ion (such as calcium or magnesium), or an aluminum ion; or complexes formed with organic bases such as diethanolamine, triethanolamine, N-Methyl-N-decanoylglucamine, and the like. Also included are ammonium and substituted or quaternized ammonium salts. A representative, non-limiting list of pharmaceutically acceptable salts can be found in S. M. Berge et al., J. Pharma Sci., 66(1), 1-19 (1977) and Remington: The Science and Practice of Pharmacy, R. Hendrickson (ed.), 21st edition, Lippincott, Williams & Wilkins, Philadelphia, Pa., (2005) page 732, table 38-5, both of which are incorporated herein by reference.

As used herein, "prevention" refers to a scheme that prevents the onset of a disease or disorder such that the clinical symptoms of the disease do not progress. Thus, "prevention" relates to provide a treatment (e.g., administration of a therapeutic substance) for an individual prior to detection of signs of disease in the individual (e.g., administering a therapeutic substance to an individual in the absence of detectable signs of disease in the individual). The individual may be an individual at risk of developing a disease, e.g., an individual having one or more risk factors known to be associated with the development or onset of a disease.

As used herein, the term "treat" refers to therapeutic treatments and prophylactic or preventative or protective measures, which aim at preventing or slowing down (alleviating) an undesired pathological change or disorder. For purposes of the present invention, beneficial or desired clinical results include, but are not limited to, alleviated symptoms, reduced severity of disease, delayed or slowed disease progression, improved or palliated disease state, and response (either partial or complete), regardless of their detectability.

"Individual" refers to humans, domesticated animals (e.g., dogs and cats), farm animals (e.g., cows, horses, sheep, goats, and pigs), laboratory animals (e.g., mice, rats, hamsters, guinea pigs, pigs, rabbits, dogs, and monkeys), and the like.

Unless otherwise specified, compounds of a given formula described herein include the disclosed compounds and all pharmaceutically acceptable salts, tautomers and deuterated forms thereof.

In certain embodiments, the present invention provides a compound of formula (Ia) and/or formula (IIa) or a tautomer thereof or a pharmaceutically acceptable salt thereof,

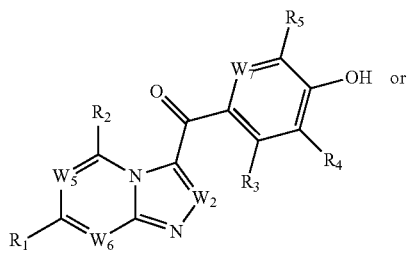

(Ia)

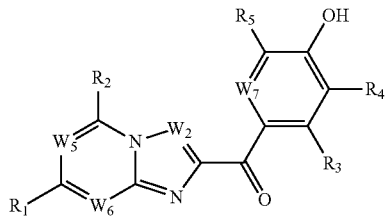

(IIa)

wherein, $W_2$ is selected from $CR_6$;

$W_5$, $W_6$ and $W_7$ are each independently selected from $CR_8$ and N;

$R_1$, $R_2$, $R_3$, $R_4$, $R_5$, $R_6$, and $R_8$ are each independently selected from hydrogen, deuterium, halogen, cyano, hydroxy, $C_{1-20}$ alkyl, $C_{1-20}$ alkoxy, and $C_{1-20}$ haloalkyl.

In certain preferred embodiments, the present invention provides a compound of formula (Ib) and/or (IIb) or a tautomer thereof or a pharmaceutically acceptable salt thereof,

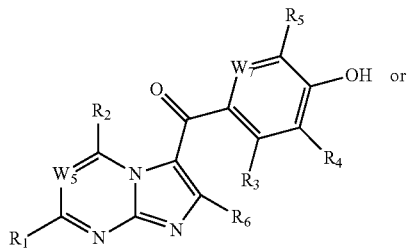

(Ib)

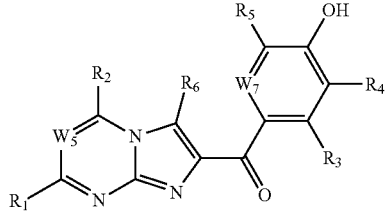

(IIb)

wherein, $W_5$ and $W_7$ are each independently selected from $CR_8$ or N;

$R_1$, $R_2$, $R_3$, $R_4$, $R_5$, $R_6$, and $R_8$ are each independently selected from hydrogen, deuterium, halogen, cyano, hydroxy, $C_{1-20}$ alkyl, $C_{1-20}$ alkoxy, and $C_{1-20}$ haloalkyl.

In certain preferred embodiments, the present invention provides a compound of formula (Ic) and/or formula (IIc) or a tautomer thereof or a pharmaceutically acceptable salt thereof,

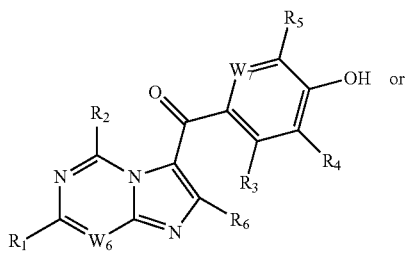

(Ic)

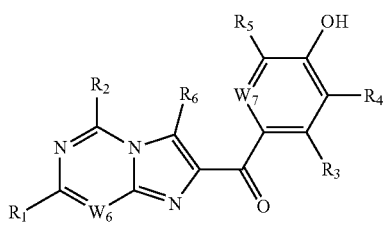

(IIc)

wherein, $W_6$ and $W_7$ are each independently selected from $CR_6$ or N;

$R_1$, $R_2$, $R_3$, $R_4$, $R_5$, $R_6$, and $R_8$ are each independently selected from hydrogen, deuterium, halogen, cyano, hydroxy, $C_{1-20}$ alkyl, $C_{1-20}$ alkoxy, and $C_{1-20}$ haloalkyl.

In certain preferred embodiments, the present invention provides a compound of formula (Id) and/or (IId) or a tautomer thereof or a pharmaceutically acceptable salt thereof,

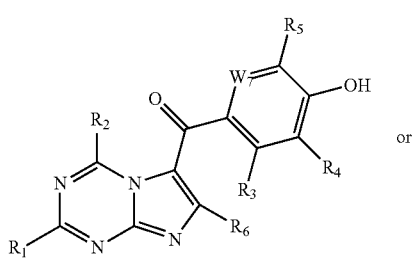

(Id)

or

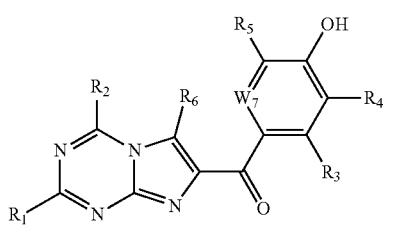

(IId)

wherein, $W_7$ is selected from $CR_8$ or N;

$R_1$, $R_2$, $R_3$, $R_4$, $R_5$, $R_6$, and $R_8$ are each independently selected from hydrogen, deuterium, halogen, cyano, hydroxy, $C_{1-20}$ alkyl, $C_{1-20}$ alkoxy, and $C_{1-20}$ haloalkyl.

In certain preferred embodiments, the present invention provides a compound of formula (Ie) or a tautomer thereof or a pharmaceutically acceptable salt thereof,

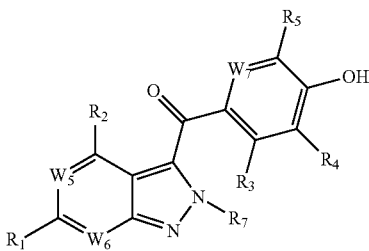

(Ie)

wherein, $W_5$, $W_6$ and $W_7$ are each independently selected from $CR_8$ and N;

$R_1$, $R_2$, $R_3$, $R_4$, $R_5$, $R_7$, and $R_8$ are each independently selected from hydrogen, deuterium, halogen, cyano, hydroxy, $C_{1-20}$ alkyl, $C_{1-20}$ alkoxy, and $C_{1-20}$ haloalkyl.

In certain preferred embodiments, the present invention provides a compound of formula (If) or a tautomer thereof or a pharmaceutically acceptable salt thereof,

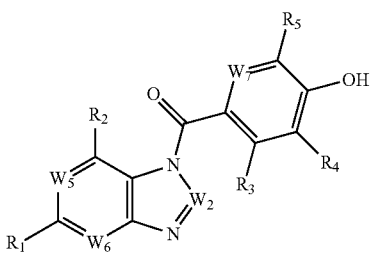

(If)

wherein, $W_2$ is selected from $CR_6$;

$W_5$, $W_6$ and $W_7$ are each independently selected from $CR_8$ and N;

$R_1$, $R_2$, $R_3$, $R_4$, $R_5$, $R_6$, and $R_8$ are each independently selected from hydrogen, deuterium, halogen, cyano, hydroxy, $C_{1-20}$ alkyl, $C_{1-20}$ alkoxy, and $C_{1-20}$ haloalkyl.

In certain preferred embodiments, the present invention provides a compound of formula (Ig) or a tautomer thereof or a pharmaceutically acceptable salt thereof,

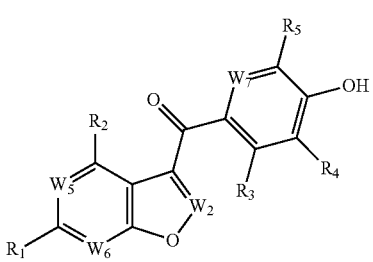

(Ig)

wherein, $W_2$ is selected from $CR_6$;

$W_5$, $W_6$ and $W_7$ are each independently selected from $CR_8$ and N;

$R_1$, $R_2$, $R_3$, $R_4$, $R_5$, $R_6$, and $R_8$ are each independently selected from hydrogen, deuterium, halogen, cyano, hydroxy, $C_{1-20}$ alkyl, $C_{1-20}$ alkoxy, and $C_{1-20}$ haloalkyl.

In a most preferred embodiment, the compound disclosed herein is selected from:
(3,5-dibromo-4-hydroxyphenyl)(2-ethylimidazo[1,2-c]pyrimidin-3-yl)methanone;
(3,5-dibromo-4-hydroxyphenyl)(2-ethylfuro[3,2-c]pyridin-3-yl)methanone;
(3,5-dibromo-4-hydroxyphenyl)(2-ethyl-7-(trifluoromethyl)imidazo[1,2-a]pyrimidin-3-yl)methanone;
(6-bromo-2-ethylimidazo[1,2-a]pyrimidin-3-yl)(3,5-dibromo-4-hydroxyphenyl)methanone;
(3,5-dibromo-4-hydroxyphenyl)(2-ethyl-6-fluoroimidazo[1,2-a]pyrimidin-3-yl)methanone;
(3,5-dibromo-4-hydroxyphenyl)(2-ethyl-6-(trifluoromethyl)imidazo[1,2-a]pyrimidin-3-yl)methanone;
(6-chloro-2-ethylimidazo[1,2-a]pyrimidin-3-yl)(3,5-dibromo-4-hydroxyphenyl)methanone;
(3,5-dibromo-4-hydroxyphenyl)(2-ethyl-7-(trifluoromethyl)imidazo[1,2-c]pyrimidin-3-yl)methanone;
(4,6-dibromo-5-hydroxypyridin-2-yl)(2-ethyl-5-fluoro-2H-indazol-3-yl)methanone;
(3,5-dibromo-4-hydroxyphenyl)(2-ethyl-5-fluoro-2H-indazol-3-yl)methanone;
3-bromo-5-(2-ethyl-6-(trifluoromethyl)imidazo[1,2-a]pyrimidin-3-carbonyl)-2-hydroxybenzo nitrile;
3-bromo-5-(2-ethyl-6-fluoroimidazo[1,2-a]pyrimidin-3-carbonyl)-2-hydroxybenzonitrile;
3-bromo-5-(3-ethyl-6-(trifluoromethyl)imidazo[1,2-a]pyrimidin-2-carbonyl)-2-hydroxybenzo nitrile;
5-(2-ethyl-6-fluoroimidazo[1,2-a]pyrimidine-3-carbonyl)-2-hydroxyiso phthalonitrile 2,2,2-trifluoroacetate;
(3,5-dibromo-4-hydroxyphenyl)(2-ethyl-2H-pyrazolo[4,3-c]pyridin-3-yl)methanone;
3-bromo-5-(2-ethyl-7-(trifluoromethyl)imidazo[1,2-a]pyrimidin-3-carbonyl)-2-hydroxybenzo nitrile;
(3-bromo-4-hydroxy-5-(trifluoromethyl)phenyl)(2-ethyl-6-fluoroimidazo[1,2-a]pyrimidin-3-yl)methanone;
(3-bromo-4-hydroxy-5-(trifluoromethyl)phenyl)(2-ethyl-6-(trifluoromethyl)imidazo[1,2-a]pyrimidin-3-yl)methanone;
(3,5-dibromo-4-hydroxyphenyl)(3-ethyl-6-fluoroimidazo[1,2-a]pyrimidin-2-yl)methanone;
3-bromo-5-(3-ethyl-6-fluoroimidazo[1,2-a]pyrimidin-2-carbonyl)-2-hydroxybenzonitrile;
(3,5-dibromo-4-hydroxyphenyl)(2-ethyl-7-($^{2}$H)imidazo[1,2-c]pyrimidin-3-yl)methanone;
(3,5-dibromo-4-hydroxyphenyl)(2-ethyl-2H-indazol-3-yl)methanone;
(4,6-dibromo-5-hydroxypyridin-2-yl)(2-ethyl-5-fluoro-benzofuran-3-yl)methanone;
(4-bromo-5-hydroxy-6-(trifluoromethyl)pyridin-2-yl)(2-ethyl-6-fluoroimidazo[1,2-a]pyrimidin-3-yl)methanone;
(4-bromo-5-hydroxy-6-(trifluoromethyl)pyridin-2-yl)(2-ethyl-6-(trifluoromethyl)imidazo[1,2-a]pyrimidin-3-yl)methanone;
(7-ethylimidazo[1,2-a][1,3,5]triazin-6-yl)(3,5-dibromo-4-hydroxyphenyl)methanone;
(7-hydroxy-2-ethylimidazo[1,2-f]pyrimidin-3-yl)(3,5-dibromo-4-hydroxyphenyl)methanone;
(3-bromo-4-hydroxy-5-(trifluoromethyl)phenyl)(3-ethyl-6-fluoroimidazo[1,2-a]pyrimidin-2-yl)methanone;
(3-bromo-4-hydroxy-5-(trifluoromethyl)phenyl)(3-ethyl-6-(trifluoromethyl)-imidazo[1,2-a]pyrimidin-2-yl)methanone;
(2,6-difluoro-3,5-dibromo-4-hydroxyphenyl)(2-ethyl-6-fluoro-imidazo[1,2-a]pyrimidin-3-yl) methanone;
(2,6-difluoro-3,5-dibromo-4-hydroxyphenyl)(2-ethyl-6-(trifluoromethyl)imidazo[1,2-a]pyrimidin-3-yl)methanone;
(3,5-dibromo-4-hydroxyphenyl)(2-ethyl-2H-pyrazolo[3,4-d]pyrimidin-3-yl)methanone;
3-bromo-5-(2-ethyl-2H-pyrazolo[3,4-d]pyrimidine-3-carbonyl)-2-hydroxybenzonitrile;
(3,5-dibromo-4-hydroxyphenyl)(2-ethylimidazo[4,5-c]pyrimidin-3-yl)methanone;
(3,5-dibromo-4-hydroxyphenyl)(2-ethylfuro[3,2-c]pyridin-3-yl)methanone;
2,6-dibromo-4-([2-ethylimidazo[1,2-a]pyrimidin-3-yl]carbonyl)phenol;
(7-chloro-2-ethylimidazo[1,2-f]pyrimidin-3-yl)(3,5-dibromo-4-hydroxyphenyl)methanone;
3-bromo-5-(2-ethylimidazo[1,2-a]pyrimidine-3-carbonyl)-2-hydroxybenzonitrile;
(4-bromo-5-hydroxy-6-(trifluoromethyl)pyridin-2-yl)(2-ethylimidazo[1,2-a]pyrimidin-3-yl)methanone;
(3-bromo-4-hydroxy-5-(trifluoromethyl)phenyl)(2-ethyl-imidazo[1,2-a]pyrimidin-3-yl)methan one;
or tautomers or pharmaceutically acceptable salts thereof.

In certain embodiments, the present invention provides a method for preparing the compound disclosed herein:

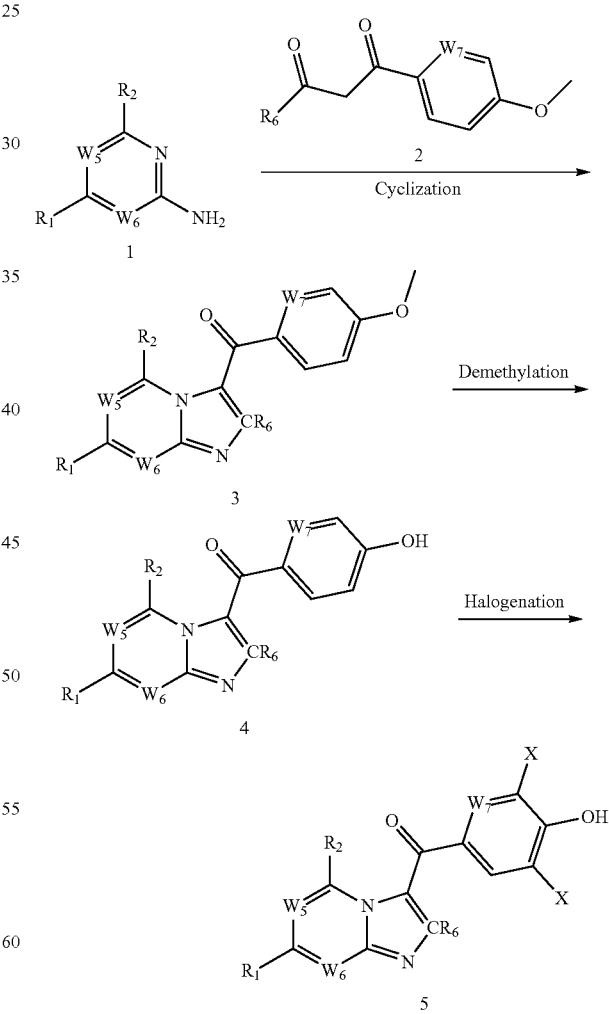

Scheme I

Step 1: Heteroaromatic amine compound 1 and 1,3-diketone compound 2 undergo cyclization to give anisole intermediate compound 3, wherein the catalyst preferably comprises (diacetoxyiodo)benzene, [bis(trifluoroacetoxy) iodo]benzene, and the like in combination with boron trifluoride etherate;

Step 2: The anisole intermediate compound 3 obtained in Step 1 undergoes demethylation to give phenol compound 4 in the presence of a catalyst, wherein the catalyst is commonly used in the art to remove the methyl protecting group of a hydroxyl, including but not limited to boron tribromide, sodium ethanethiolate and the like, and commonly used catalysts and methodology are detailed in Greene, T. W. and Wuts, P. G. M., Greene's Protective Groups in Organic Synthesis, 4th edition, John Wiley and Sons;

Step 3: The phenol compound 4 obtained in Step 2 undergoes halogenation to give phenol compound 5 (X is halogen), wherein a halogenating reagent includes halogen elements (such as bromine and iodine), chlorosuccinimide, bromosuccinimide, iodosuccinimide, phosphorus trichloride, phosphorus pentachloride, phosphorus tribromide, phosphorus pentabromide, and the like.

In addition, the scheme I may optionally further comprise the following:

Step 4: The phenol compound 5 obtained in Step 3 further undergoes cyanation in which one or more halogens on the phenol ring are substituted with cyano.

Step 1: Compound 6 reacts with acyl halide compound 7 under an alkaline condition to give anisole intermediate compound 8, wherein the alkali used may be an inorganic alkali or an organic alkali; the inorganic alkali can be selected from hydroxides of alkali metals or alkaline earth metals (e.g., sodium hydroxide, potassium hydroxide, barium hydroxide, lithium hydroxide, calcium hydroxide, and magnesium hydroxide), carbonates or bicarbonates of alkali metals or alkaline earth metals (e.g., potassium carbonate, sodium carbonate, lithium carbonate, calcium carbonate, magnesium carbonate, and sodium bicarbonate), alkoxides of alkali metals or alkaline earth metals (e.g., sodium methoxide, sodium ethoxide, sodium tert-butoxide, potassium tert-butoxide, etc.), amides of alkali metals or alkaline earth metals (e.g., sodium amide, sodium bis(trimethylsilyl)amide, and LDA), n-butyllithium, sec-butyllithium, and tert-butyllithium; and the organic alkali can be selected from organic amines commonly used in the art, such as triethylamine, trimethylamine, pyridine, piperidine, 4-dimethylaminopyridine, morpholine, N-methylmorpholine, N,N,N',N-tetramethylethylenediamine, DBU, DBN, DABCO, etc.;

Step 2: The anisole intermediate compound 8 obtained in Step 1 undergoes demethylation to give phenol compound 9 in the presence of a catalyst, wherein the catalyst is commonly used in the art to remove the methyl protecting group of a hydroxyl, including but not limited to boron tribromide, sodium ethanethiolate and the like, and commonly used catalysts and methodology are detailed in Greene, T. W. and Wuts, P. G. M., Greene's Protective Groups in Organic Synthesis, 4th edition, John Wiley and Sons;

Step 3: The phenol compound 9 obtained in Step 2 undergoes halogenation to give phenol compound 10 (X is halogen), wherein a halogenating reagent includes halogen elements (such as bromine and iodine), chlorosuccinimide, bromosuccinimide, iodosuccinimide, phosphorus trichloride, phosphorus pentachloride, phosphorus tribromide, phosphorus pentabromide, and the like.

In addition, the scheme II may optionally further comprise the following:

Step 4: the phenol compound 5 obtained in Step 3 further undergoes cyanation in which one or more halogens on the phenol ring are substituted with cyano.

In certain embodiments, the present invention further provides a pharmaceutical composition for preventing and/or treating hyperuricemia and gout, comprising a compound of formula (Ia) and/or formula (Ib) or a tautomer thereof or a pharmaceutically acceptable salt thereof disclosed herein, and a pharmaceutically acceptable carrier. The pharmaceutical composition of the present invention comprises, about 90 wt. % to about 80 wt. %, 80 wt. % to about 70 wt. %, 70 wt. % to about 60 wt. %, 60 wt. % to about 50 wt. %, 50 wt. % to about 40 wt. %, 40 wt. % to about 30 wt. %, 30 wt. % to about 20 wt. %, 20 wt. % to about 10 wt. %, 10 wt. % to about 1.0 wt. %, 1.0 wt. % to about 0.1 wt. %, or 0.1 wt. % to about 0.01 wt. % of the compound of formula (Ia) and/or formula (Ib) or the tautomer thereof or the pharmaceutically acceptable salt thereof disclosed herein. The pharmaceutically acceptable carrier may be a solid or a liquid. The solid carrier may be one or more substances used as excipients, diluents, sweeteners, solubilizers, lubricants, binders, tablet disintegrating agents, stabilizers, preservatives, or encapsulating materials. The liquid carrier may be a solvent or a liquid dispersion medium. Suitable solid carriers include, but are not limited to, for example, cellulose, glucose, lactose, mannitol, magnesium stearate, magnesium carbonate, sodium carbonate, sodium saccharin, sucrose, dextrin, Scheme II

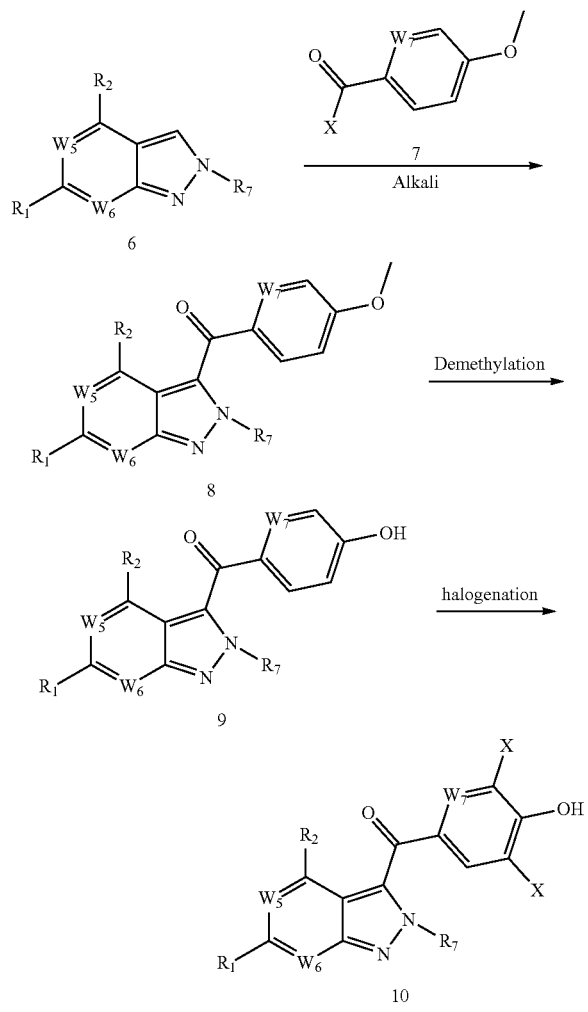

talc, starch, pectin, gelatin, tragacanth, acacia, sodium alginate, parabens, methylcellulose, sodium carboxymethylcellulose, wax of low melting point, cocoa butter, and the like. Suitable liquid carriers include, but are not limited to, water, ethanol, polyols (e.g., glycerol, propylene glycol, liquid polyethylene glycols, and the like), vegetable oils (e.g., peanut oil, cottonseed oil, safflower oil, sesame oil, olive oil, corn oil, and soybean oil), glycerides, agar, pyrogen-free water, isotonic saline, Ringer's solution, and mixtures thereof.

Methods for preparing the pharmaceutical composition of the present invention are generally known in the art, for example, as described in "Remington: the Science and Practice of Pharmacy, 19th edition, 1995". Generally known methods for preparing the pharmaceutical composition of the present invention include conventional mixing, granulating, tableting, coating, dissolving or lyophilizing processes.

The therapeutically effective amount of the compound or the pharmaceutical composition comprising the same described herein may be readily determined by routine experimentations. The most effective and convenient route of administration may be determined by routine experimentations.

The pharmaceutical composition of the present invention may be administered to a patient or subject in need of treatment by any suitable route of administration, including oral administration, parenteral administration (including subcutaneous, intramuscular, intravenous, intraurethral and intradermal administrations), rectal administration, nasal administration, vaginal administration or administration via an implantable reservoir. Preferably, the pharmaceutical composition of the invention present is administered orally.

The orally administered composition in the present invention comprises a solid dosage form such as pill, tablet, caplet, capsule (including immediate release, timed release and sustained release formulations), granule, and powder; or a liquid dosage form such as solution, syrup, elixir, emulsion, and suspension. Sterile solutions or ocular drug delivery devices are intended for ocular administration. Sterile solutions, emulsions and suspensions are intended for parenteral administration.

The dosage of the pharmaceutical composition of the present invention depends on various factors including the age, weight and condition of a patient and the route of administration. The exact dosage to be administered is left to the discretion of the attending physician. The actual dose levels and time frame of the active ingredient of the pharmaceutical composition of the present invention may be varied to obtain an amount of the active ingredient that, for a particular patient, composition and route of administration, may induce the desired therapeutic response without posing toxicity to the patient. Typically, the medicament or pharmaceutical composition of the present invention is administered at a dose sufficient to reduce or eliminate symptoms associated with bacterial infection.

The preferred dose of the medicament or pharmaceutical composition of the present invention is the maximum dose that a patient can tolerate and that does not produce serious or unacceptable side effects. Exemplary dose ranges include 0.01 to 250 mg/day, 0.01 to 100 mg/day, 1 to 100 mg/day, 10 to 100 mg/day, 1 to 10 mg/day, and 0.01 to 10 mg/day. The preferred dose of the medicament is the maximum dose that a patient can tolerate and that does not produce serious or unacceptable side effects. In examples, the medicament is administered at a dose of about 0.01 to about 100 mg/kg bw/day, about 0.1 to about 10 mg/kg/day, or about 1.0 to about 10 mg/kg bw/day.

In one embodiment, a therapeutically effective dose results in a serum medicament concentration from about 0.1 ng/mL to about 50-100 mg/mL. Typically, these pharmaceutical compositions should be administrated at a dose of about 0.001 to about 2000 mg/kg bw/day. For example, the range of the dose for systemic administration to a human patient may be 1-10 mg/kg, 20-80 mg/kg, 5-50 mg/kg, 75-150 mg/kg, 100-500 mg/kg, 250-750 mg/kg, 500-1000 mg/kg, 1-10 mg/kg, 5-50 mg/kg, 25-75 mg/kg, 50-100 mg/kg, 100-250 mg/kg, 50-100 mg/kg, 250-500 mg/kg, 500-750 mg/kg, 750-1000 mg/kg, 1000-1500 mg/kg, 10 1500-2000 mg/kg, 5 mg/kg, 20 mg/kg, 50 mg/kg, 100 mg/kg, 500 mg/kg, 1000 mg/kg, 1500 mg/kg, or 2000 mg/kg. Pharmaceutical unit dosage forms are prepared to provide about 1 to about 5000 mg (e.g., about 100 to about 2500 mg) of the compound or combination of essential ingredients per unit dosage form. Preferred unit dose formulations are those containing a daily dose or unit, a daily sub-dose, or an appropriate fraction thereof, as discussed herein, of a given ingredient.

The present invention is further illustrated by the following specific examples, which are not intended to limit the present invention. Many modifications and adjustments may be made by those skilled in the art in light of the above teachings without departing from the spirit and scope of the present invention.

EXAMPLES

Example 1: Synthesis of (3,5-dibromo-4-hydroxyphenyl)(2-ethylfuro[3,2-c]pyridin-3-yl) methanone

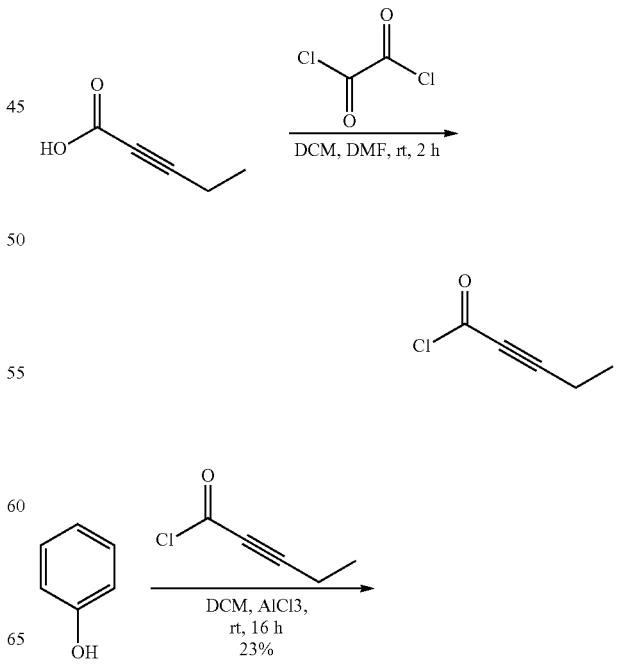

-continued

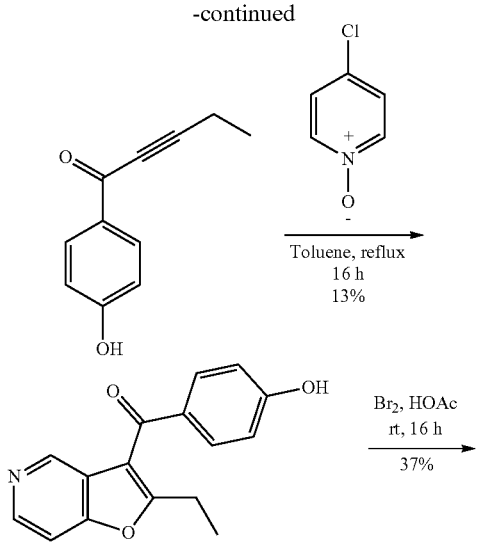

Step 1: Synthesis of pent-2-ynoyl chloride

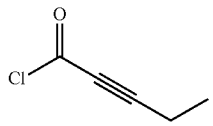

To a solution of pent-2-ynoic acid (2.45 g, 25 mmol) in dichloromethane (50 mL) was added oxalyl chloride (3.465 g, 27.5 mmol) and a drop of N,N-dimethylformamide. The mixture was stirred at room temperature for 2 h to give pent-2-ynoyl chloride (0.5 M in dichloromethane, 50 mL, 25 mmol), which was directly used in the next step without purification.

Step 2: Synthesis of 1-(4-hydroxyphenyl)pent-2-yn-1-one

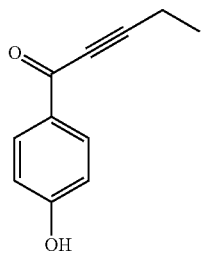

A mixture of phenol (2.35 g, 25 mmol) and aluminum chloride hexahydrate (16.5 g, 125 mmol) in dichloromethane (100 mL) was stirred at 0° C. for 2 h. Pent-2-ynoyl chloride (0.5 M in dichloromethane, 50 mL, 25 mmol) was added to the mixture. The resulting mixture was stirred at room temperature overnight. The mixture was poured into ice and the pH value was adjusted to 8 with saturated aqueous sodium bicarbonate. Then dichloromethane (50 mL×3) was added for extraction. The organic phases were washed with saturated brine, dried over anhydrous sodium sulfate, filtered and concentrated. The residue was purified by flash chromatography (petroleum ether/ethyl acetate=1/1) to give 1-(4-hydroxyphenyl)pent-2-yn-1-one (1 g, 23%) in the form of a yellow solid. LCMS (ESI) [M+H]$^+$=175.

Step 3: Synthesis of (2-ethylfuro[3,2-c]pyridin-3-yl)(4-hydroxyphenyl)methanone

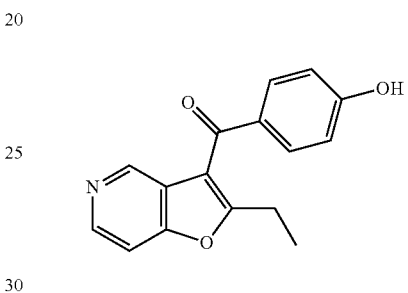

To a solution of 1-(4-hydroxyphenyl)pent-2-yn-1-one (1 g, 5.75 mmol) in toluene (30 mL) was added 4-chloropyridin-1-oxide (742 mg, 5.75 mmol). The mixture was stirred at 130° C. for 16 h. The mixture was concentrated, and the residue was purified by flash chromatography (petroleum ether/ethyl acetate=1/4) to give (2-ethylfuro[3,2-c]pyridin-3-yl)(4-hydroxyphenyl) methanone (0.2 g, 13%) in the form of a yellow solid. LCMS (ESI) [M+H]$^+$=268.0.

Step 4: Synthesis of (3,5-dibromo-4-hydroxyphenyl)(2-ethylfuro[3,2-c]pyridin-3-yl)methanone

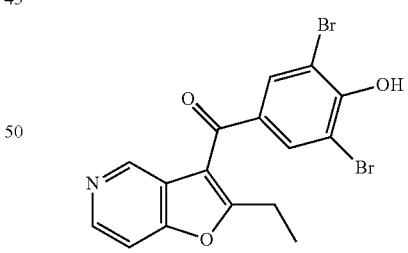

To a solution of (2-ethylfuro[3,2-c]pyridin-3-yl)(4-hydroxyphenyl)methanone (0.19 g, 0.71 mmol) in acetic acid (2 mL) was added bromine water (166 mg, 1.07 mmol) at 0° C. The mixture was stirred at room temperature for 6 h, then concentrated. The residue was purified by Prep-TLC (methanol/dichloromethane=1/20) to give (3,5-dibromo-4-hydroxyphenyl) (2-ethylfuro[3,2-c]pyridin-3-yl)methanone (0.11 g, 37%). LCMS (ESI) [M+H]$^+$=424; $^1$H NMR (400 MHz, DMSO-d$_6$) δ 8.75 (s, 1H), 8.52 (d, J=5.6 Hz, 1H), 7.98 (s, 2H), 7.79 (dd, J=5.6 Hz, 1H), 2.82 (q, J=7.2 Hz, 2H), 1.28 (t, J=7.6 Hz, 3H).

Example 2: Synthesis of (3,5-dibromo-4-hydroxyphenyl)(2-ethyl-7-(trifluoromethyl) imidazo[1,2-a]pyrimidin-3-yl)methanone

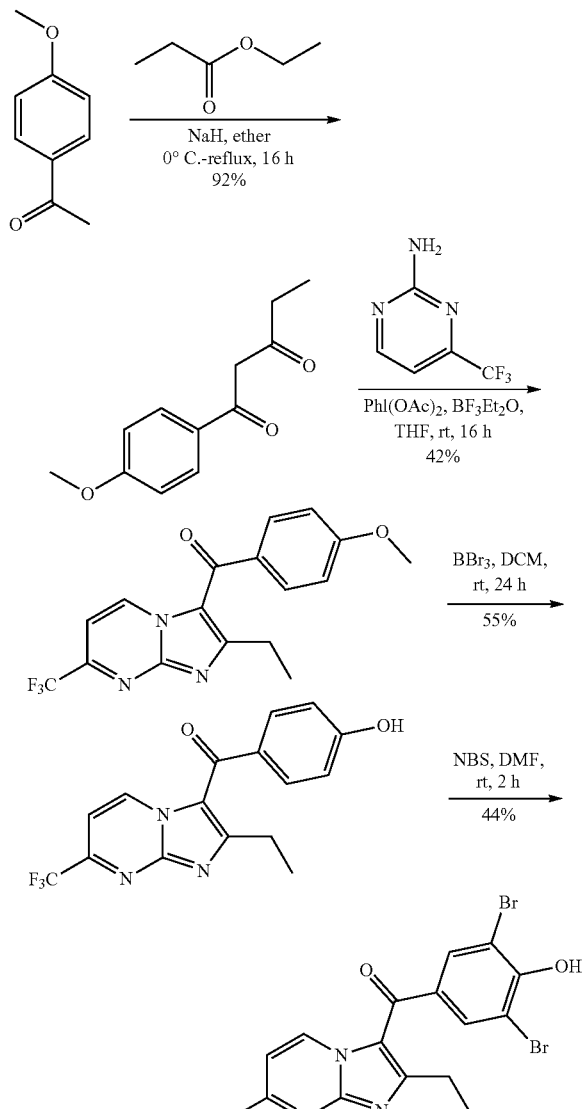

Step 1: Synthesis of 1-(4-methoxyphenyl)pentane-1,3-dione

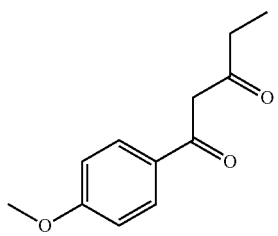

To a solution of sodium hydride (11.2 g, 60% in oil, 280 mmol) in diethyl ether (250 mL) was added ethanol (1 mL), and then a solution of 4-methoxyacetophenone (20 g, 133 mmol) in diethyl ether (50 mL) was added over a period of 5 min. Ethyl propionate (23.4 g, 266 mmol) was added to the mixture above rapidly, and the resulting mixture was heated under reflux for 16 h. After cooling to room temperature, the mixture was diluted with water (400 mL). The solid precipitated was collected and washed with water and diethyl ether to give the crude product (sodium salt). The crude product was dissolved in water, acidized with hydrochloric acid and then extracted with ethyl acetate. The organic phases were concentrated to give 1-(4-methoxyphenyl)pentane-1,3-dione (25 g, 92%) in the form of a yellow oil. LCMS (ESI) [M+H]$^+$=207.

Step 2: Synthesis of (2-ethyl-7-(trifluoromethyl) imidazo[1,2-a]pyrimidin-3-yl) (4-methoxyphenyl)methanone

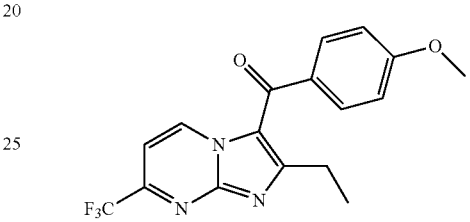

A solution of 1-(4-methoxyphenyl)pentane-1,3-dione (0.35 g, 1.69 mmol), 4-(trifluoromethyl)pyrimidin-2-amine (0.332 g, 2.03 mmol) and (diacetoxyiodo)benzene (0.820 g, 2.53 mmol) in tetrahydrofuran (15 mL) was stirred at room temperature for 2 h. Then boron trifluoride etherate (0.14 g, 1.00 mmol) was added, and the resulting mixture was stirred at room temperature overnight. The reaction was quenched with water and ethyl acetate (20 mL×3) was added for extraction. The organic phases were washed with water (20 mL×2), dried over anhydrous sodium sulfate, filtered and concentrated. The residue was purified by flash chromatography (petroleum ether/ethyl acetate=3/1) to give (2-ethyl-7-(trifluoromethyl) imidazo[1,2-a]pyrimidin-3-yl)(4-methoxyphenyl)methanone (150 mg, 42%) in the form of a yellow oil. LCMS (ESI) [M+H]$^+$=350.

Step 3: Synthesis of (2-ethyl-7-(trifluoromethyl) imidazo[1,2-a]pyrimidin-3-yl) (4-hydroxyphenyl)methanone

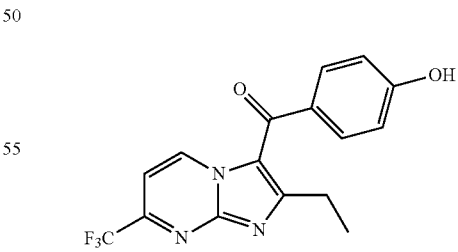

To a solution of (2-ethyl-7-(trifluoromethyl)imidazo[1,2-a]pyrimidin-3-yl) (4-methoxyphenyl)-methanone (200 mg, 0.571 mmol) in dichloromethane (2 mL) was added boron tribromide (17% in dichloromethane, 5 mL). The mixture was stirred at room temperature for 24 h. Then the reaction was quenched with water and ethyl acetate (20 mL×3) was added for extraction. The organic phases were washed with water (20 mL×2), dried over anhydrous sodium sulfate, filtered and concentrated to give (2-ethyl-7-(trifluoromethyl)imidazo[1,2-a]pyrimidin-3-yl)(4-hydroxyphenyl)methanone (110 mg, 55%) in the form of a brown solid. LCMS (ESI) [M+H]$^+$=336.

Step 4: Synthesis of (3,5-dibromo-4-hydroxyphenyl)(2-ethyl-7-(trifluoromethyl)imidazo[1,2-a]pyrimidin-3-yl)methanone

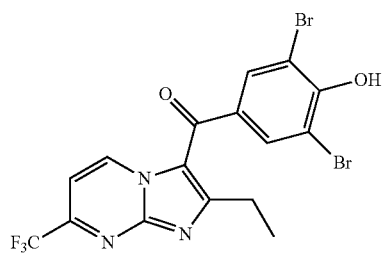 [SMILES: CCc1nc2nc(C(F)(F)F)ccn2c1C(=O)c1cc(Br)c(O)c(Br)c1]

To a solution of (2-ethyl-7-(trifluoromethyl)imidazo[1,2-a]pyrimidin-3-yl) (4-hydroxyphenyl)-methanone (110 mg, 0.328 mmol) in N,N-dimethylformamide (5.0 mL) was added N-bromosuccinimide (118.8 mg, 0.67 mmol) at 0° C. The mixture was stirred at room temperature for 2 h, then concentrated. The residue was purified by Prep-HPLC to give (3,5-dibromo-4-hydroxyphenyl)(2-ethyl-7-(trifluoromethyl)imidazo[1,2-a]pyrimidin-3-yl)methanone (66 mg, 44%). LCMS (ESI) [M+H]$^+$=492; $^1$H NMR (400 MHz, DMSO-d$_6$) δ 9.57-9.55 (m, 1H), 7.92 (s, 2H), 7.73-7.71 (m, 1H), 2.60 (q, 2H), 1.23 (t, 3H).

Example 3: Synthesis of (6-bromo-2-ethylimidazo[1,2-a]pyrimidin-3-yl)(3,5-dibromo-4-hydroxyphenyl)methanone

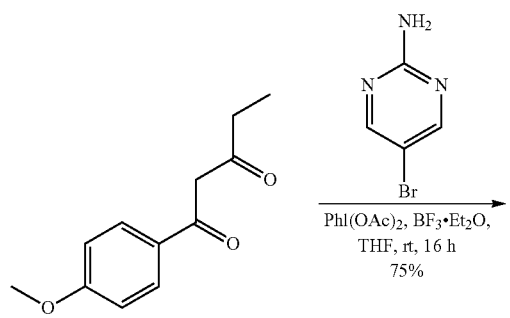

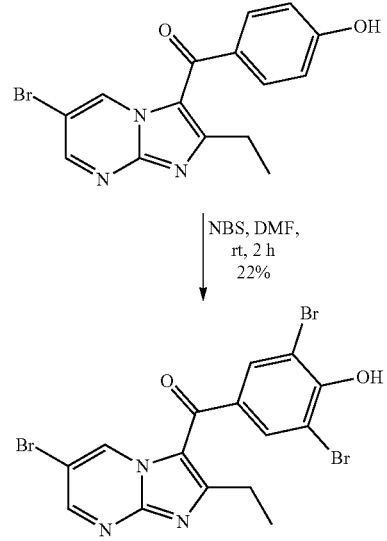

Step 1: Synthesis of (6-bromo-2-ethylimidazo[1,2-a]pyrimidin-3-yl)(4-methoxyphenyl) methanone A solution of 1-(4-methoxyphenyl)pentane-1,3-dione (1.00 g, 4.85 mmol), 5-bromopyrimidin-2-amine (1.01 g, 5.82 mmol) and (diacetoxyiodo)benzene (2.34 g, 7.28 mmol) in tetrahydrofuran (15 mL) was stirred at room temperature for 2 h. Then boron trifluoride etherate (0.14 g, 1.00 mmol) was added, and the resulting mixture was stirred at room temperature overnight. The reaction was quenched with water and ethyl acetate (20 mL×3) was added for extraction. The organic phases were washed with water (20 mL×2), dried over anhydrous sodium sulfate, filtered and concentrated. The residue was purified by flash chromatography (petroleum ether/ethyl acetate=3/1) to give (6-bromo-2-ethylimidazo[1,2-a]pyrimidin-3-yl)(4-methoxyphenyl) methanone (750 mg, 75%) in the form of a yellow oil. LCMS (ESI) [M+H]$^+$=360.

Step 2: Synthesis of (6-bromo-2-ethylimidazo[1,2-a]pyrimidin-3-yl)(4-hydroxyphenyl) methanone

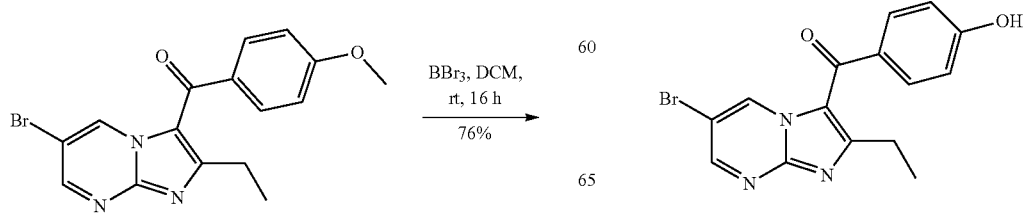

To a solution of (6-bromo-2-ethylimidazo[1,2-a]pyrimidin-3-yl)(4-methoxyphenyl) methanone (500 mg, 1.38 mmol) in dichloromethane (2 mL) was added boron tribromide (17% in dichloromethane, 5 mL, 8.5 mmol). The mixture was stirred at room temperature for 24 h. Then the reaction was quenched with water and ethyl acetate (20 mL×3) was added for extraction. The organic phases were washed with water (20 mL×2), dried over anhydrous sodium sulfate, filtered and concentrated to give (6-bromo-2-ethylimidazo[1,2-a]pyrimidin-3-yl) (4-hydroxyphenyl)methanone (380 mg, 76%) in the form of a brown solid. LCMS (ESI) [M+H]$^+$=346.

Step 3: Synthesis of (6-bromo-2-ethylimidazo[1,2-a]pyrimidin-3-yl)(3,5-dibromo-4-hydroxyphenyl) methanone

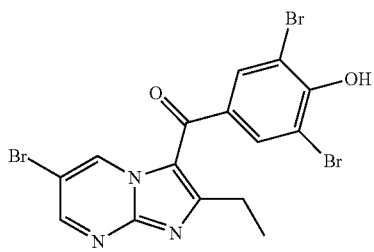 [SMILES: CCc1nc2ncc(Br)cn2c1C(=O)c1cc(Br)c(O)c(Br)c1]

To a solution of (6-bromo-2-ethylimidazo[1,2-a]pyrimidin-3-yl)(4-hydroxyphenyl) methanone (100 mg, 0.289 mmol) in N,N-dimethylformamide (5.0 mL) was added N-bromosuccinimide (51 mg, 0.289 mmol) at 0° C. The mixture was stirred at room temperature for 2 h, then concentrated. The residue was purified by Prep-HPLC to give (6-bromo-2-ethylimidazo[1,2-a]pyrimidin-3-yl)(3,5-dibromo-4-hydroxyphenyl)methanone (22 mg, 22%). LCMS (ESI) [M+H]$^+$=492; $^1$H NMR (400 MHz, DMSO-d$_6$) δ 9.42 (s, 1H), 8.83 (s, 1H), 7.85 (s, 2H), 2.60 (q, 2H), 1.20 (t, 3H).

Example 4: Synthesis of (3,5-dibromo-4-hydroxyphenyl)(2-ethyl-6-fluoroimidazo[1,2-a]pyrimidin-3-yl)methanone

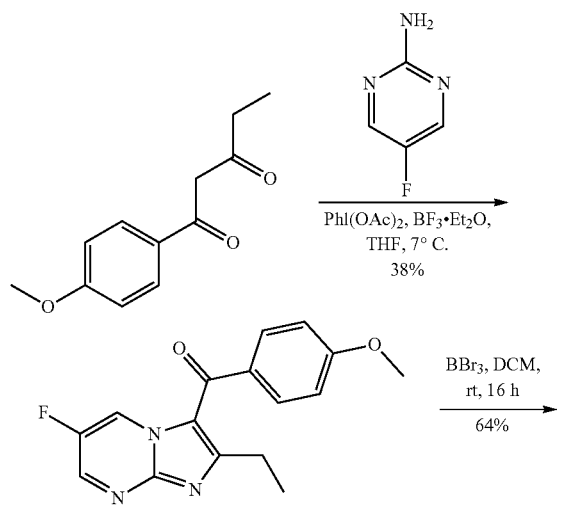

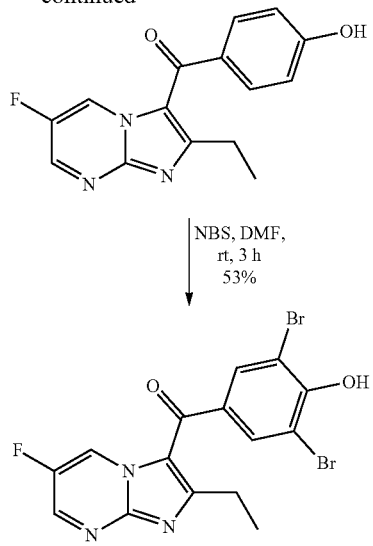

Step 1: Synthesis of (2-ethyl-6-fluoroimidazo[1,2-a]pyrimidin-3-yl)(4-methoxyphenyl) methanone

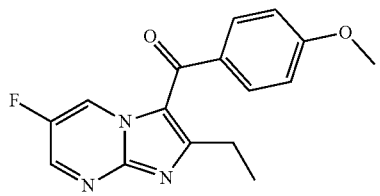 [SMILES: CCc1nc2ncc(F)cn2c1C(=O)c1ccc(OC)cc1]

A solution of 1-(4-methoxyphenyl)pentane-1,3-dione (20 g, 97 mmol), (diacetoxyiodo) benzene (30.8 g, 96 mmol), boron trifluoride etherate (1.2 g, 16 mmol) and 5-fluoropyrimidin-2-amine (9.04 g, 80 mmol) in tetrahydrofuran (300 mL) was stirred at room temperature overnight. The mixture was poured into saturated aqueous sodium bicarbonate (300 mL) and then ethyl acetate (100 mL×3) was added for extraction. The organic phases were washed with saturated brine, dried over anhydrous sodium sulfate, filtered and concentrated. The residue was purified by flash chromatography (petroleum ether/ethyl acetate=1/1) to give (2-ethyl-6-fluoroimidazo[1,2-a]pyrimidin-3-yl)(4-methoxyphenyl) methanone (9 g, 38%) in the form of a yellow solid. LCMS (ESI) [M+H]$^+$=300.1.

Step 2: Synthesis of (2-ethyl-6-fluoroimidazo[1,2-a]pyrimidin-3-yl)(4-hydroxyphenyl) methanone

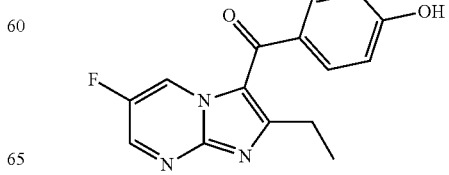

To a solution of (2-ethyl-6-fluoroimidazo[1,2-a]pyrimidin-3-yl)(4-methoxyphenyl) methanone (9 g, 30.1 mmol) in anhydrous dichloromethane (60 mL) was added boron tribromide (10 mL) dropwise at 0° C. under nitrogen atmosphere. The mixture was stirred at room temperature for 16 h. The mixture was slowly poured into saturated aqueous sodium bicarbonate (100 mL) at 0° C. and then ethyl acetate (150 mL×3) was added for extraction. The organic phases were washed with saturated brine (150 mL), dried over anhydrous sodium sulfate, filtered and concentrated to give (2-ethyl-6-fluoroimidazo[1,2-a]pyrimidin-3-yl) (4-hydroxyphenyl)methanone (5.5 g, 64%) in the form of a yellow solid, which was directly used in the next step without purification. LCMS (ESI) [M+H]$^+$=286.0.

Step 3: Synthesis of (3,5-dibromo-4-hydroxyphenyl)(2-ethyl-6-fluoroimidazo[1,2-a]pyrimidin-3-yl) methanone

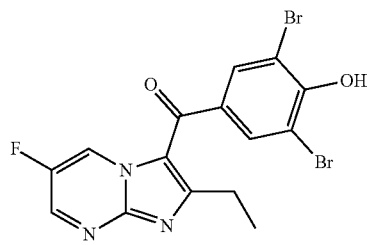

To a solution of (2-ethyl-6-fluoroimidazo[1,2-a]pyrimidin-3-yl)(4-hydroxyphenyl) methanone (5.5 g, 19.3 mmol) in N,N-dimethylformamide (50 mL) was added N-bromosuccinimide (8.2 g, 46.3 mmol) dropwise at 0° C. The mixture was stirred at room temperature for 3 h. The reaction was quenched with water and a solid was precipitated. The mixture was filtered and the filter cake was washed with water, recrystallized from acetonitrile, and then washed with mixed solution of methanol/dichloromethane (1/10) to give (3,5-dibromo-4-hydroxyphenyl)(2-ethyl-6-fluoroimidazo[1,2-a]pyrimidin-3-yl)methanone (4.5 g, 53%). LCMS (ESI) [M+H]$^+$=441.7; $^1$H NMR (400 MHz, DMSO-d$_6$) δ 10.98 (s, 1H), 9.51 (s, 1H), 8.99 (s, 1H), 7.91 (s, 2H), 2.50 (q, J=7.6 Hz, 2H), 1.19 (t, J=7.6 Hz, 3H).

Example 5: Synthesis of (3,5-dibromo-4-hydroxyphenyl)(2-ethyl-6-(trifluoromethyl) imidazo[1,2-a]pyrimidin-3-yl)methanone

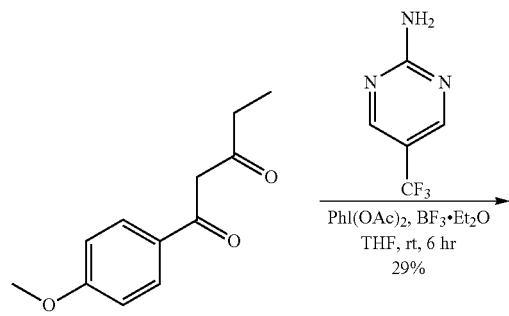

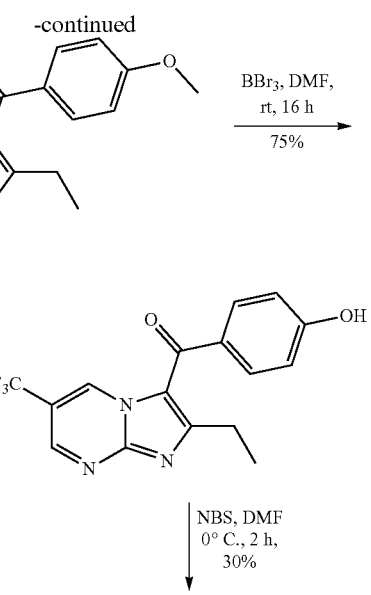

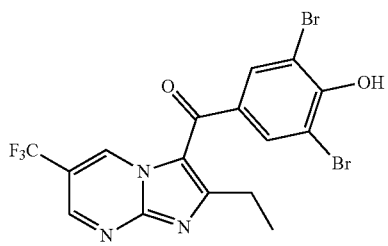

Step 1: Synthesis of (2-ethyl-6-(trifluoromethyl) imidazo[1,2-a]pyrimidin-3-yl) (4-methoxyphenyl) methanone

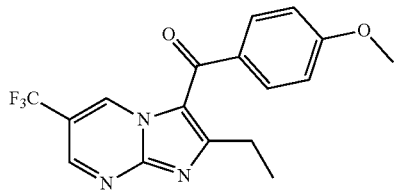 [SMILES: CCc1nc2ncc(C(F)(F)F)cn2c1C(=O)c1ccc(OC)cc1]

A solution of 1-(4-methoxyphenyl)pentane-1,3-dione (4.50 g, 21.84 mmol), 5-(trifluoromethyl)pyrimidin-2-amine (7.40 g, 45.39 mmol) and (diacetoxyiodo)benzene (13.30 g, 41.30 mmol) in tetrahydrofuran (80 mL) was stirred at room temperature for 2 h. Then boron trifluoride etherate (0.7 g, 5.00 mmol) was added, and the resulting mixture was stirred at room temperature overnight. The reaction was quenched with water and ethyl acetate (40 mL×3) was added for extraction. The organic phases were washed with water (20 mL×2), dried over anhydrous sodium sulfate, filtered and concentrated. The residue was purified by flash chromatography (petroleum ether/ethyl acetate=3/1) to give (2-ethyl-6-(trifluoromethyl) imidazo[1,2-a]pyrimidin-3-yl)(4-methoxyphenyl)methanone (2.20 g, 29%) in the form of a yellow oil. LCMS (ESI) [M+H]$^+$=350.

Step 2: Synthesis of (2-ethyl-6-(trifluoromethyl) imidazo[1,2-a]pyrimidin-3-yl) (4-hydroxyphenyl) methanone

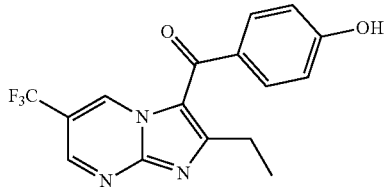 [SMILES: CCc1nc2ncc(C(F)(F)F)cn2c1C(=O)c1ccc(O)cc1]

To a solution of (2-ethyl-6-(trifluoromethyl)imidazo[1,2-a]pyrimidin-3-yl) (4-methoxyphenyl)-methanone (4.90 g, 14.04 mmol) in dichloromethane (25 mL) was added boron tribromide (27.0 g, 10 mL, 107.70 mmol). The mixture was stirred at room temperature overnight. The mixture was poured into saturated aqueous sodium bicarbonate (100 mL) and a yellow solid was precipitated. The mixture was filtered and the filter cake was washed with petroleum ether (30 mL×3) and dried to give (2-ethyl-6-(trifluoromethyl)imidazo[1,2-a]pyrimidin-3-yl)(4-hydroxyphenyl)methanone (3.50 g, 75%) in the form of a brown solid. LCMS (ESI) [M+H]$^+$=336.

Step 3: Synthesis of (3,5-dibromo-4-hydroxyphenyl)(2-ethyl-6-(trifluoromethyl)imidazo[1,2-a]pyrimidin-3-yl)methanone

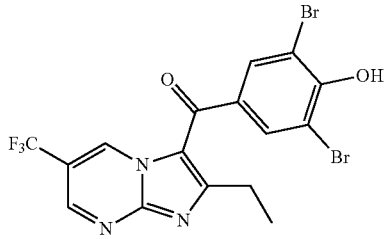 [SMILES: CCc1nc2ncc(C(F)(F)F)cn2c1C(=O)c1cc(Br)c(O)c(Br)c1]

To a solution of (2-ethyl-6-(trifluoromethyl)imidazo[1,2-a]pyrimidin-3-yl) (4-hydroxyphenyl)methanone (6.40 g, 19.10 mmol) in N,N-dimethylformamide (60 mL) was slowly added N-bromosuccinimide (120 mg, 0.67 mmol) at 0° C. The mixture was stirred at room temperature for 2 h. Then the reaction was quenched with water and a solid was precipitated. The mixture was filtered, and the filter cake was washed with water, acetonitrile and petroleum ether and dried to give (3,5-dibromo-4-hydroxyphenyl)(2-ethyl-6-(trifluoromethyl)imidazo[1,2-a]pyrimidin-3-yl)methanone (2.80 g, 30%). LCMS (ESI) [M+H]$^+$=492; $^1$H NMR (400 MHz, DMSO-d$_6$) δ 9.62 (s, 1H), 9.14 (s, 1H), 7.92 (s, 2H), 2.53 (q, 2H), 1.22 (t, 3H).

Example 6: Synthesis of (6-chloro-2-ethylimidazo[1,2-a]pyrimidin-3-yl)(3,5-dibromo-4-hydroxyphenyl)methanone

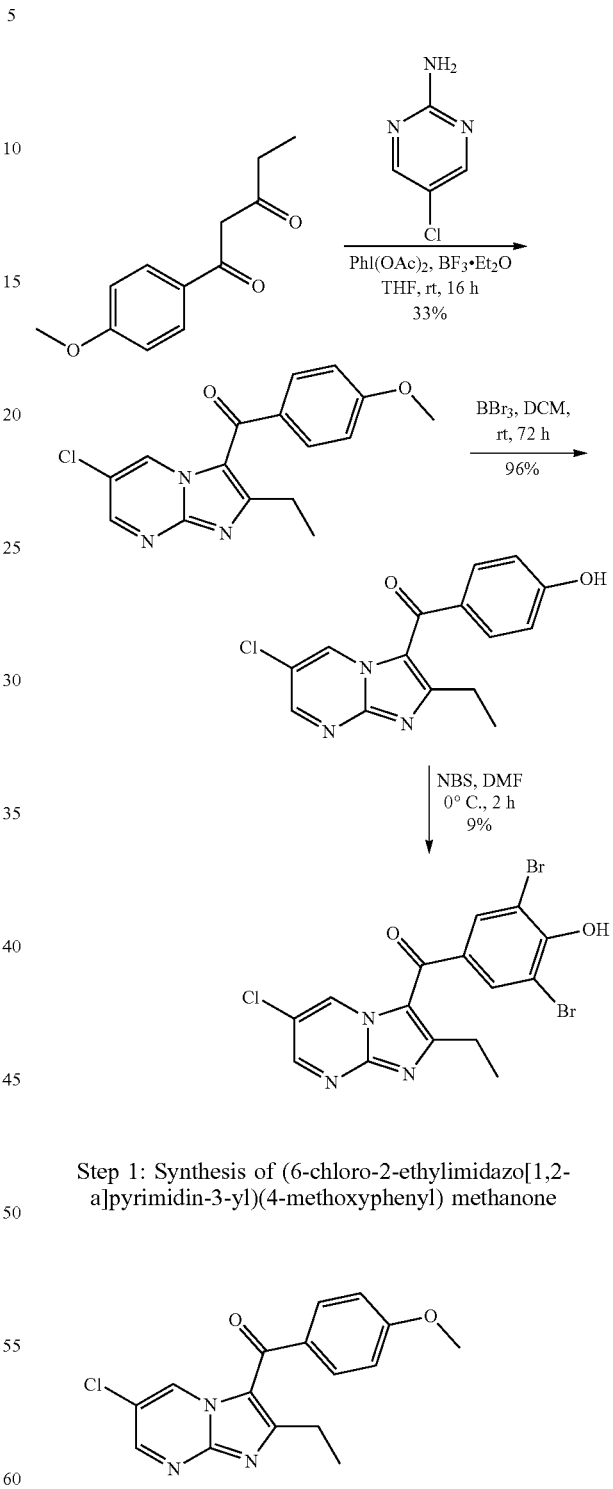

Step 1: Synthesis of (6-chloro-2-ethylimidazo[1,2-a]pyrimidin-3-yl)(4-methoxyphenyl) methanone

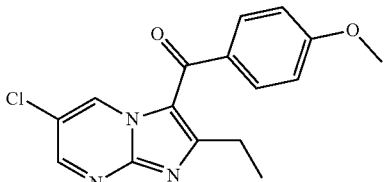

A solution of 1-(4-methoxyphenyl)pentane-1,3-dione (1.00 g, 4.85 mmol), 5-chloropyridin-2-amine (0.75 g, 5.82 mmol) and (diacetoxyiodo)benzene (2.30 g, 7.28 mmol) in tetrahydrofuran (15 mL) was stirred at room temperature for 2 h. Then boron trifluoride etherate (0.14 g, 1.00 mmol) was added, and the resulting mixture was stirred at room temperature overnight. The reaction was quenched with water and ethyl acetate (20 mL×3) was added for extraction. The organic phases were washed with water (20 mL×2), dried over anhydrous sodium sulfate, filtered and concentrated. The residue was purified by flash chromatography (petroleum ether/ethyl acetate=3/1) to give (6-chloro-2-ethylimidazo[1,2-a]pyrimidin-3-yl) (4-methoxyphenyl)methanone (500 mg, 33%) in the form of a yellow oil. LCMS (ESI) [M+H]$^+$=316.

Step 2: Synthesis of (6-chloro-2-ethylimidazo[1,2-a]pyrimidin-3-yl)(4-hydroxyphenyl) methanone

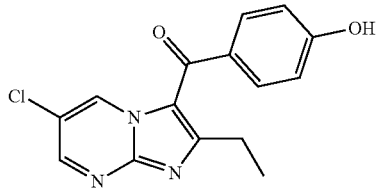 [SMILES: CCc1nc2ncc(Cl)cn2c1C(=O)c1ccc(O)cc1]

To a solution of (6-chloro-2-ethylimidazo[1,2-a]pyrimidin-3-yl)(4-methoxyphenyl) methanone (250 mg, 0.79 mmol) in dichloromethane (2 mL) was added boron tribromide (17% in dichloromethane, 5 mL, 8.5 mmol). The mixture was stirred at room temperature for 72 h. Then the reaction was quenched with water and ethyl acetate (20 mL×3) was added for extraction. The organic phases were washed with water (20 mL×2), dried over anhydrous sodium sulfate, filtered and concentrated to give (6-chloro-2-ethylimidazo[1,2-a]pyrimidin-3-yl) (4-hydroxyphenyl)methanone (230 mg, 96%) in the form of a deep red solid. LCMS (ESI) [M+H]$^+$=302.

Step 3: Synthesis of (6-chloro-2-ethylimidazo[1,2-a]pyrimidin-3-yl)(3,5-dibromo-4-hydroxyphenyl)-methanone

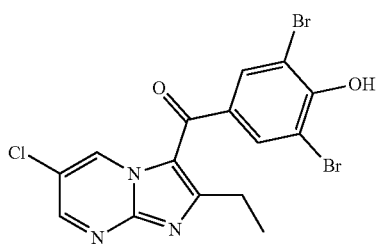 [SMILES: CCc1nc2ncc(Cl)cn2c1C(=O)c1cc(Br)c(O)c(Br)c1]

To a solution of (6-chloro-2-ethylimidazo[1,2-a]pyrimidin-3-yl)(4-hydroxyphenyl)-methanone (50 mg, 0.17 mmol) in N,N-dimethylformamide (3.0 mL) was added N-bromosuccinimide (75 mg, 0.42 mmol) slowly at 0° C. The mixture was stirred at room temperature for 2 h, then concentrated. The residue was purified by Prep-HPLC to give (6-chloro-2-ethylimidazo[1,2-a]pyrimidin-3-yl)(3,5-dibromo-4-hydroxyphenyl)-methanone (6.9 mg, 9%). LCMS (ESI) [M+H]$^+$=458; $^1$H NMR (400 MHz, DMSO-d$_6$) δ 9.40 (s, 1H), 8.83 (s, 1H), 7.87 (s, 2H), 2.52 (q, 2H), 1.22 (t, 3H).

Example 7: Synthesis of (3,5-dibromo-4-hydroxyphenyl)(2-ethyl-7-(trifluoromethyl) imidazo[1,2-c]pyrimidin-3-yl)methanone

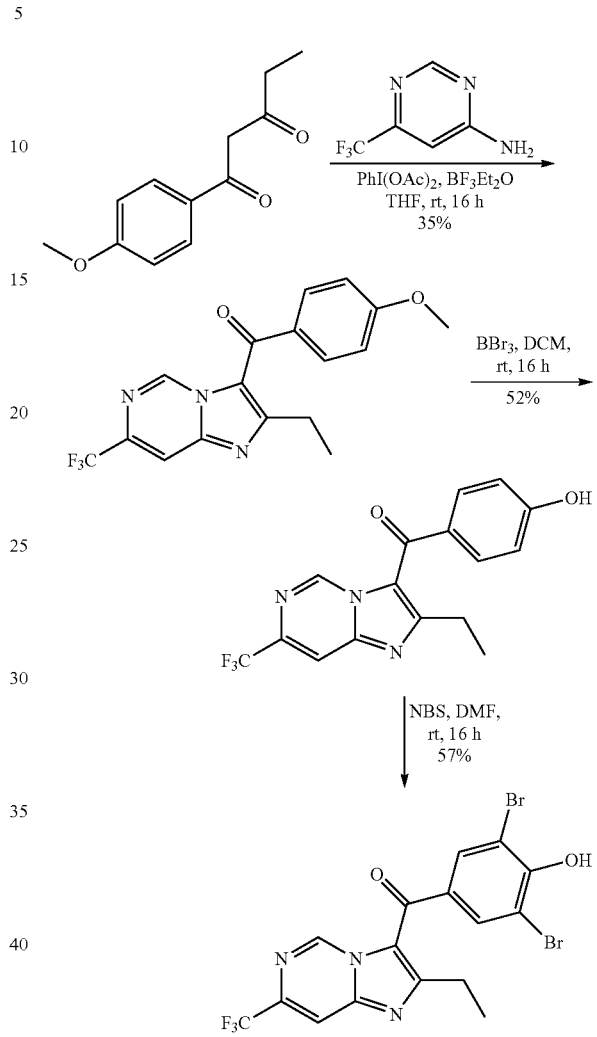

Step 1: Synthesis of (2-ethyl-7-(trifluoromethyl) imidazo[1,2-c]pyrimidin-3-yl) (4-methoxyphenyl) methanone

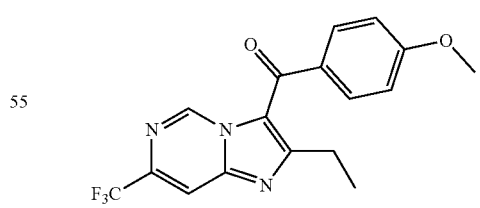

A solution of 1-(4-methoxyphenyl)pentane-1,3-dione (20 g, 97 mmol), (diacetoxyiodo) benzene (30.8 g, 96 mmol), boron trifluoride etherate (1.2 g, 16 mmol) and 6-(trifluoromethyl) pyrimidin-4-amine (13 g, 80 mmol) in tetrahydrofuran (300 mL) was stirred at room temperature overnight. The mixture was poured into saturated aqueous sodium bicarbonate (300 mL) and then ethyl acetate (100 mL×3) was added for extraction. The organic phases were washed with saturated brine, dried over anhydrous sodium sulfate, filtered and concentrated. The residue was purified by flash chromatography (petroleum ether/ethyl acetate=2/1) to give (2-ethyl-7-(trifluoromethyl)imidazo[1,2-c]pyrimidin-3-yl)(4-methoxyphenyl) methanone (10 g, 35%). LCMS (ESI) [M+H]⁺=350.0.

Step 2: Synthesis of (2-ethyl-7-(trifluoromethyl) imidazo[1,2-c]pyrimidin-3-yl) (4-hydroxyphenyl) methanone

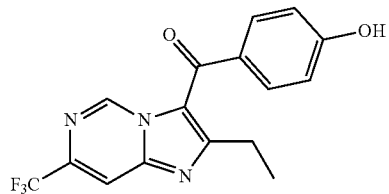 [SMILES: CCc1nc2cc(C(F)(F)F)ncn2c1C(=O)c1ccc(O)cc1]

To a solution of (2-ethyl-7-(trifluoromethyl)imidazo[1,2-c]pyrimidin-3-yl) (4-methoxyphenyl)methanone (10 g, 28.6 mmol) in anhydrous dichloromethane (60 mL) was added boron tribromide (10 mL) dropwise at 0° C. The mixture was stirred at room temperature for 16 h. The mixture was poured into saturated aqueous sodium bicarbonate (100 mL) at 0° C. and then ethyl acetate (150 mL×3) was added for extraction. The organic phases were washed with saturated brine (150 mL), dried over sodium sulfate, filtered and concentrated to give (2-ethyl-7-(trifluoromethyl)imidazo[1,2-c]pyrimidin-3-yl)(4-hydroxyphenyl)methanone (5.0 g, 52%), which was directly used in the next step without purification. LCMS (ESI) [M+H]⁺=336.0.

Step 3: Synthesis of (3,5-dibromo-4-hydroxyphenyl)(2-ethyl-7-(trifluoromethyl)imidazo[1,2-c]pyrimidin-3-yl)methanone

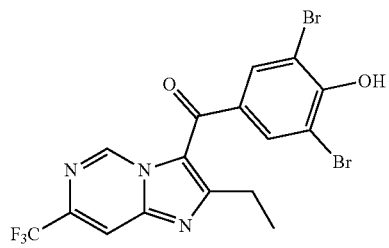 [SMILES: CCc1nc2cc(C(F)(F)F)ncn2c1C(=O)c1cc(Br)c(O)c(Br)c1]

To a solution of (2-ethyl-7-(trifluoromethyl)imidazo[1,2-c]pyrimidin-3-yl) (4-hydroxyphenyl)methanone (5.0 g, 14.9 mmol) in N,N-dimethylformamide (50 mL) was added N-bromosuccinimide (6.3 g, 35.8 mmol) dropwise at 0° C. The mixture was stirred at room temperature for 3 h. The reaction was quenched with water and a solid was precipitated. The mixture was filtered and the filter cake was washed with water, recrystallized from acetonitrile, and further purified by flash chromatography (methanol/dichloromethane=1/20) to give (3,5-dibromo-4-hydroxyphenyl) (2-ethyl-7-(trifluoromethyl)imidazo[1,2-c]pyrimidin-3-yl) methanone (4.2 g, 57%). LCMS (ESI) [M+H]⁺=492.7; ¹H NMR (400 MHz, DMSO-d₆) δ 9.76 (s, 1H), 8.42 (s, 1H), 7.95 (s, 2H), 2.52 (q, J=7.6 Hz, 2H), 1.22 (t, J=7.6 Hz, 3H).

Example 8: Synthesis of (4,6-dibromo-5-hydroxypyridin-2-yl)(2-ethyl-5-fluoro-2H-indazol-3-yl) methanone

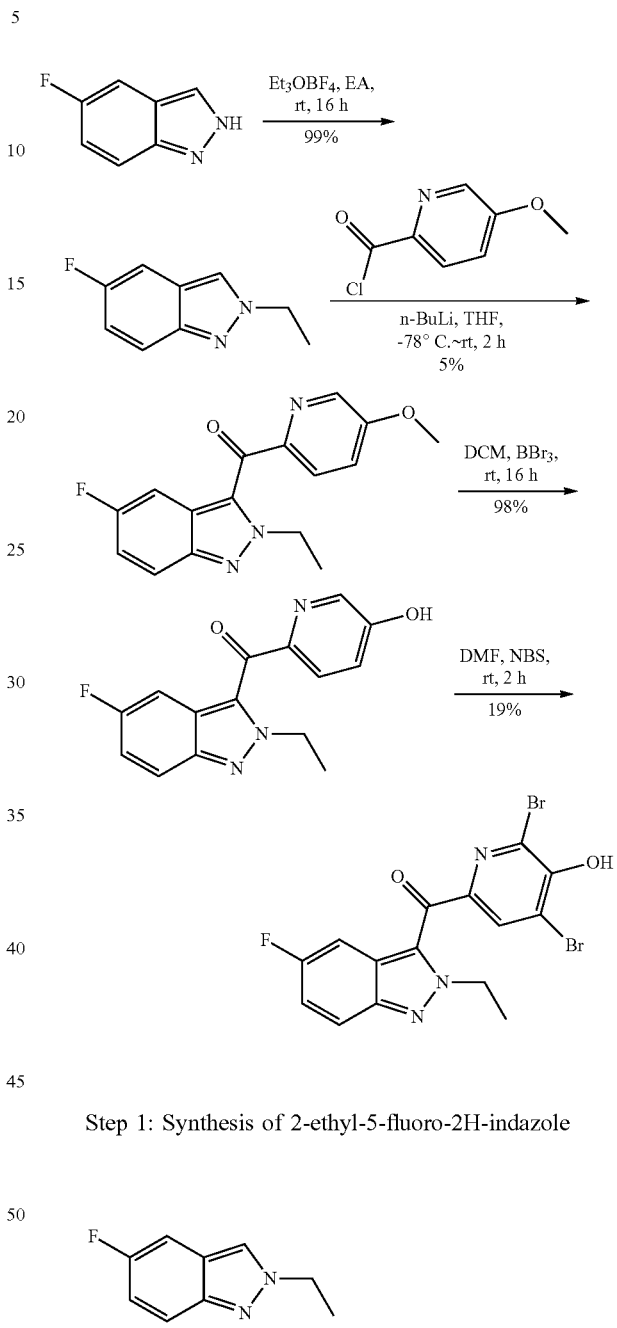

Step 1: Synthesis of 2-ethyl-5-fluoro-2H-indazole

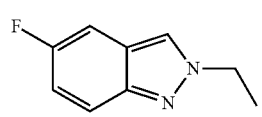

To a solution of 5-fluoro-2H-indazole (1.9 g, 13.9 mmol) in ethyl acetate (25 mL) was added triethyloxonium tetrafluoroborate (4 g, 20.9 mmol) and the resulting mixture was stirred at room temperature for 16 h. The mixture was diluted with water (20 mL) and then ethyl acetate (20 mL×2) was added for extraction. The organic phases were washed with saturated brine, dried over anhydrous sodium sulfate, filtered and concentrated. The residue was purified by flash chromatography (petroleum ether/ethyl acetate=7/3) to give 2-ethyl-5-fluoro-2H-indazole (2.29 g, 99%) in the form of a yellow oil. LCMS (ESI) [M+H]⁺=165.

Step 2: Synthesis of (2-ethyl-5-fluoro-2H-indazol-3-yl)(5-methoxypyridin-2-yl)methanone

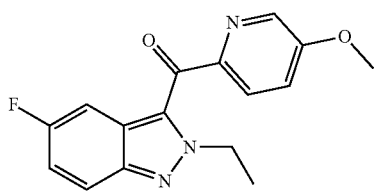

To a solution of 2-ethyl-5-fluoro-2H-indazole (164 mg, 1 mmol) in anhydrous tetrahydrofuran (5 mL) was added n-butyllithium (0.8 mL, 2.5 M in tetrahydrofuran, 2 mmol) dropwise at −78° C. under argon atmosphere. The mixture was stirred at −20° C. for 30 min. After the mixture was cooled to −78° C., 5-methoxypicolinoyl chloride (342 mg, 2 mmol) was added and the resulting mixture was stirred at room temperature for 1 h. The reaction was quenched with water and then ethyl acetate (20 mL×3) was added for extraction. The organic phases were washed with saturated brine, dried over anhydrous sodium sulfate, filtered and concentrated. The residue was purified by Prep-TLC (petroleum ether/ethyl acetate=1/1) to give (2-ethyl-5-fluoro-2H-indazol-3-yl)(5-methoxypyridin-2-yl)methanone (15 mg, 5% yield) in the form of a yellow solid. LCMS (ESI) [M+H]$^+$=300.

Step 3: Synthesis of (2-ethyl-5-fluoro-2H-indazol-3-yl)(5-hydroxypyridin-2-yl)methanone

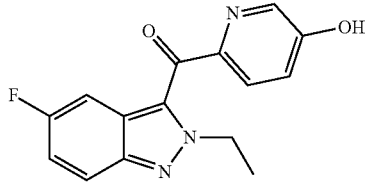 [SMILES: CCn1nc2ccc(F)cc2c1C(=O)c1ccc(O)cn1]

To a solution of (2-ethyl-5-fluoro-2H-indazol-3-yl)(5-methoxypyridin-2-yl)methanone (15 mg, 0.05 mmol) in anhydrous dichloromethane (1 mL) was added boron tribromide (2 mL, 17% in dichloromethane) dropwise at 0° C. under nitrogen atmosphere. The mixture was stirred at room temperature for 16 h. The mixture was slowly added to saturated aqueous sodium bicarbonate (100 mL) at 0° C. and then ethyl acetate (20 mL×3) was added for extraction. The organic phases were washed with saturated brine (150 mL), dried over anhydrous sodium sulfate, filtered and concentrated to give (2-ethyl-5-fluoro-2H-indazol-3-yl)(5-hydroxypyridin-2-yl)methanone (14 mg, 98%) in the form of a yellow solid, which was directly used in the next step without purification. LCMS (ESI) [M+H]$^+$=286.0.

Step 4: Synthesis of (4,6-dibromo-5-hydroxypyridin-2-yl)(2-ethyl-5-fluoro-2H-indazol-3-yl) methanone To a solution of (2-ethyl-5-fluoro-2H-indazol-3-yl)(5-hydroxypyridin-2-yl)methanone (14 mg, 0.05 mmol) in N,N-dimethylformamide (1 mL) was added N-bromosuccinimide (27 mg, 0.15 mmol) at 0° C. The mixture was stirred at room temperature for 2 h. The reaction was quenched with water (10 mL) and ethyl acetate (20 mL×2) was added for extraction. The organic phases were washed with saturated brine (150 mL), dried over anhydrous sodium sulfate, filtered and concentrated. The residue was purified by Prep-HPLC to give (4,6-dibromo-5-hydroxypyridin-2-yl)(2-ethyl-5-fluoro-2H-indazol-3-yl)methanone (4.1 mg, 19%). LCMS (ESI) [M+H]$^+$=442; $^1$H NMR (400 MHz, CD$_3$OD) δ 8.26 (s, 1H), 7.74-7.77 (m, 1H), 7.11-7.22 (m, 2H), 4.73 (q, J=6.4 Hz, 2H), 1.60 (t, J=6.8 Hz, 3H).

Example 9: Synthesis of (3,5-dibromo-4-hydroxyphenyl)(2-ethyl-5-fluoro-2H-indazol-3-yl) methanone

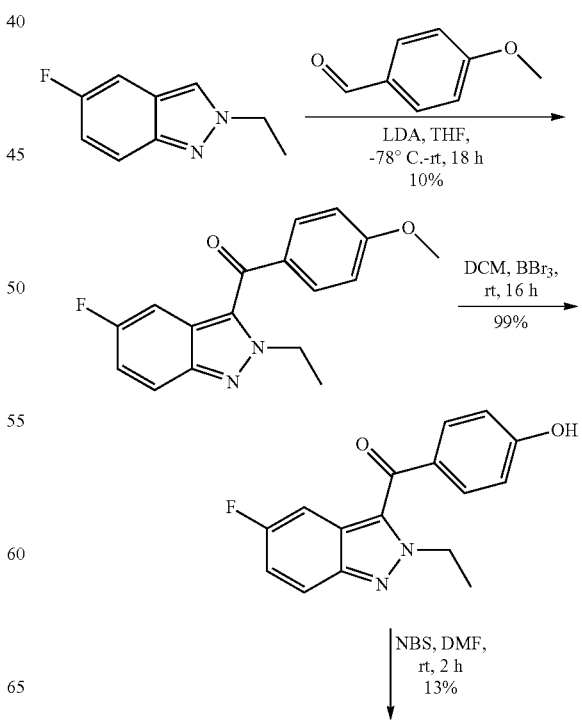

-continued

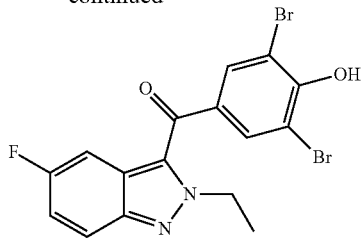

Step 1: Synthesis of (2-ethyl-5-fluoro-2H-indazol-3-yl)(4-methoxyphenyl)methanone

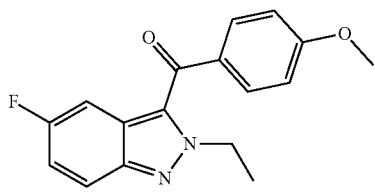 [SMILES: CCn1nc2ccc(F)cc2c1C(=O)c1ccc(OC)cc1]

To a solution of 2-ethyl-5-fluoro-2H-indazole (1.64 g, 10 mmol) in anhydrous tetrahydrofuran (30 mL) was added lithium diisopropylamide (10 mL, 2 M in tetrahydrofuran, 20 mmol) dropwise at 0° C. under argon atmosphere. The mixture was stirred at 0° C. for 30 min and then cooled to −78° C. 4-methoxybenzaldehyde (2.055 g, 15 mmol) was slowly added and the resulting mixture was stirred at room temperature for 16 h. The reaction was quenched with water (100 mL) and ethyl acetate (50 mL×3) was added for extraction. The organic phases were washed with saturated brine, dried over anhydrous sodium sulfate, filtered and concentrated. The residue was purified by Prep-TLC (petroleum ether/ethyl acetate=1/1) to give (2-ethyl-5-fluoro-2H-indazol-3-yl)(4-methoxyphenyl)methanone (300 mg, 10%) in the form of a yellow oil. LCMS (ESI) [M+H]$^+$=299.

Step 2: Synthesis of (2-ethyl-5-fluoro-2H-indazol-3-yl)(4-hydroxyphenyl)methanone

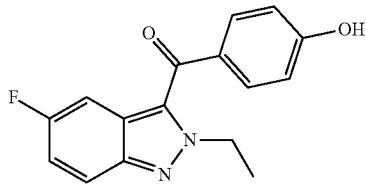

To a solution of (2-ethyl-5-fluoro-2H-indazol-3-yl)(4-methoxyphenyl)methanone (300 mg, 1 mmol) in anhydrous dichloromethane (2 mL) was added boron tribromide (8 mL, 17% in dichloromethane) dropwise at 0° C. under nitrogen atmosphere. The mixture was stirred at room temperature for 16 h. The mixture was slowly added to saturated aqueous sodium bicarbonate (100 mL) at 0° C. and then ethyl acetate (30 mL×3) was added for extraction. The organic phases were washed with saturated brine (150 mL), dried over anhydrous sodium sulfate, filtered and concentrated to give (2-ethyl-5-fluoro-2H-indazol-3-yl)(4-hydroxyphenyl) methanone (284 mg, 99%) in the form of a yellow oil, which was directly used in the next step without purification. LCMS (ESI) [M+H]$^+$=285.

Step 3: Synthesis of (3,5-dibromo-4-hydroxyphenyl)(2-ethyl-5-fluoro-2H-indazol-3-yl) methanone

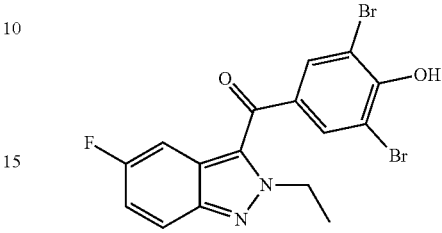

To a solution of (2-ethyl-5-fluoro-2H-indazol-3-yl)(4-hydroxyphenyl)methanone (100 mg, 0.35 mmol) in N,N-dimethylformamide (5 mL) was added N-bromosuccinimide (157 mg, 0.88 mmol) at 0° C. The mixture was stirred at room temperature for 2 h, then concentrated. The residue was purified by Prep-HPLC to give (3,5-dibromo-4-hydroxyphenyl)(2-ethyl-5-fluoro-2H-indazol-3-yl)methanone (20 mg, 13%). LCMS (ESI) [M+H]$^+$=441; $^1$H NMR (400 MHz, DMSO-d$_6$) δ 7.90-7.93 (m, 3H), 7.26-7.31 (m, 1H), 6.78-6.82 (m, 1H), 4.67 (q, J=6.4 Hz, 2H), 1.52 (t, J=6.8 Hz, 3H).

Example 10: Synthesis of 3-bromo-5-(2-ethyl-6-(trifluoromethyl)imidazo[1,2-a]pyrimidine-3-carbonyl)-2-hydroxybenzonitrile

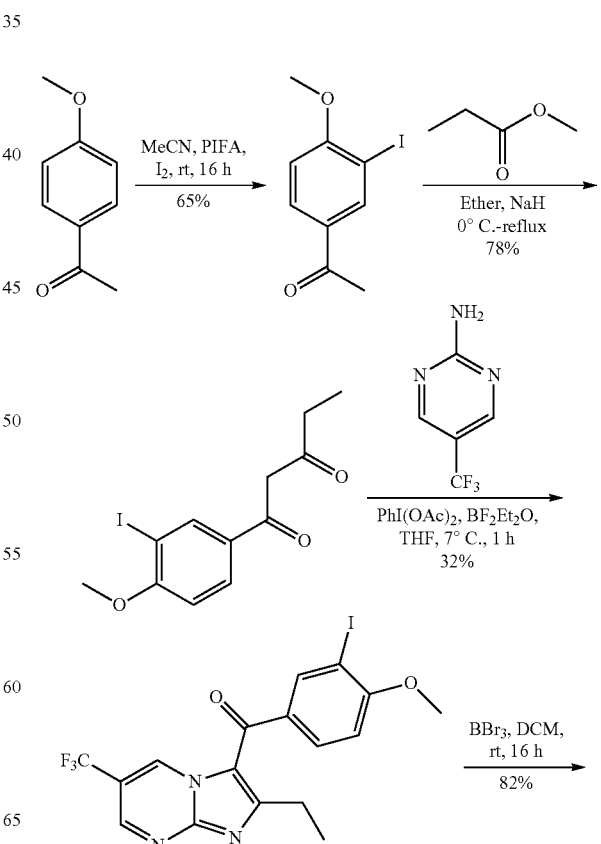

-continued

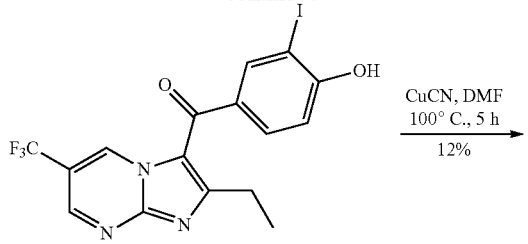

CuCN, DMF
100° C., 5 h
―――――――→
12%

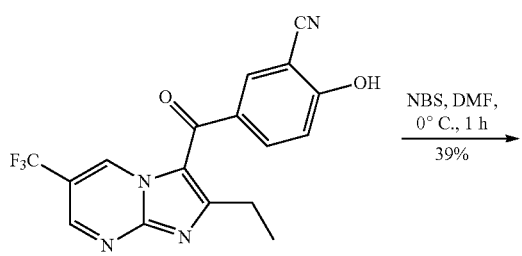

NBS, DMF,
0° C., 1 h
―――――――→
39%

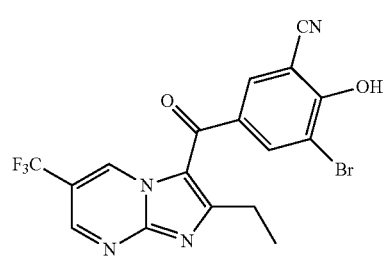

Step 1: Synthesis of
1-(3-iodo-4-methoxyphenyl)ethanone

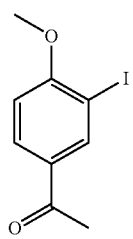

A mixture of 1-(4-methoxyphenyl)ethanone (15 g, 100 mmol), phenyliodine (III) bis(trifluoroacetate) (47.3 g, 110 mmol) and iodine (25.2 g, 100 mmol) in acetonitrile (300 mL) was stirred at room temperature for 16 h. The mixture was diluted with water (400 mL) and washed with aqueous sodium sulfite (100 mL×2), and then ethyl acetate (100 mL×4) was added for extraction. The organic phases were washed with saturated brine (150 mL), dried over anhydrous sodium sulfate, filtered and concentrated. The residue was purified by flash chromatography (petroleum ether/ethyl acetate=1/1) to give 1-(3-iodo-4-methoxyphenyl) ethanone (18 g, 65%) in the form of a yellow solid. LCMS (ESI) [M+H]$^+$=277.

Step 2: Synthesis of
1-(3-iodo-4-methoxyphenyl)pentane-1,3-dione

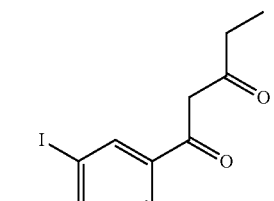

To a solution of sodium hydride (5 g, 60% in oil, 125 mmol) in diethyl ether (200 mL) was added a solution of 1-(3-iodo-4-methoxyphenyl)ethanone (13.8 g, 50 mmol) in diethyl ether (50 mL) dropwise at 0° C. Ethyl propionate (10.2 g, 100 mmol) was then added rapidly, and the resulting mixture was heated under reflux for 16 h. After cooling to room temperature, the mixture was diluted with water (400 mL). The pH value was adjusted to 5 with concentrated hydrochloric acid. Ethyl acetate (50 mL×4) was added for extraction. The organic phases were washed with saturated brine (150 mL), dried over anhydrous sodium sulfate, filtered and concentrated. The residue was purified by flash chromatography (petroleum ether/ethyl acetate=3/1) to give 1-(3-iodo-4-methoxyphenyl)pentane-1,3-dione (13 g, 78%) in the form of a yellow solid. LCMS (ESI) [M+H]$^+$=333.

Step 3: Synthesis of (2-ethyl-6-(trifluoromethyl) imidazo[1,2-a]pyrimidin-3-yl)(3-iodo-4-methoxyphenyl)methanone

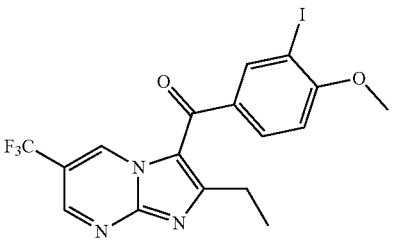 [SMILES: CCc1nc2ncc(C(F)(F)F)cn2c1C(=O)c1ccc(OC)c(I)c1]

A solution of 1-(3-iodo-4-methoxyphenyl)pentane-1,3-dione (332 mg, 1 mmol), (diacetoxyiodo)benzene (483 mg, 1.5 mmol) and 5-(trifluoromethyl)pyrimidin-2-amine (163 mg, 1 mmol) in tetrahydrofuran (5 mL) was stirred at 7° C. for 1 h. Boron trifluoride etherate (28 g, 0.2 mmol) was added slowly, and the resulting mixture was stirred at room temperature overnight. The mixture was poured into saturated aqueous sodium bicarbonate (20 mL) and then ethyl acetate (20 mL×3) was added for extraction. The organic phases were washed with saturated brine, dried over anhydrous sodium sulfate, filtered and concentrated. The residue was purified by flash chromatography (petroleum ether/ethyl acetate=3/2) to give (2-ethyl-6-(trifluoromethyl)imidazo[1,2-a]pyrimidin-3-yl)(3-iodo-4-methoxyphenyl)methanone (150 mg, 32%) in the form of a yellow solid. LCMS (ESI) [M+H]$^+$=476.

Step 4: Synthesis of (2-ethyl-6-(trifluoromethyl)imidazo[1,2-a]pyrimidin-3-yl)(3-iodo-4-hydroxyphenyl)methanone

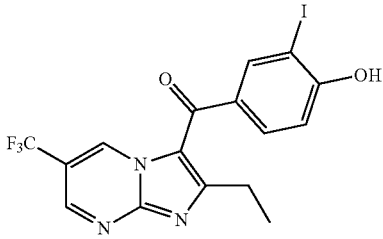 [SMILES: CCc1nc2ncc(C(F)(F)F)cn2c1C(=O)c1ccc(O)c(I)c1]

To a solution of (2-ethyl-6-(trifluoromethyl)imidazo[1,2-a]pyrimidin-3-yl)(3-iodo-4-methoxyphenyl)methanone (5 g, 10.53 mmol) in dichloromethane (25 mL) was added boron tribromide (10 mL, 99%), and the mixture was stirred at room temperature for 24 h. The mixture was slowly added to saturated aqueous sodium bicarbonate (100 mL) at 0° C. and then dichloromethane (150 mL×3) was added for extraction. The organic phases were washed with saturated brine (50 mL), dried over anhydrous sodium sulfate, filtered and concentrated. The residue was washed with petroleum ether (50 mL) and ethyl acetate (10 mL), and the filter cake was dried to give (2-ethyl-6-(trifluoromethyl)imidazo[1,2-a]pyrimidin-3-yl)(3-iodo-4-hydroxyphenyl)methanone (4 g, 82%) in the form of a yellow solid, which was directly used in the next step without purification. LCMS (ESI) [M+H]$^+$= 462.

Step 5: Synthesis of 5-(2-ethyl-6-(trifluoromethyl)imidazo[1,2-a]pyrimidine-3-carbonyl)-2-hydroxybenzonitrile

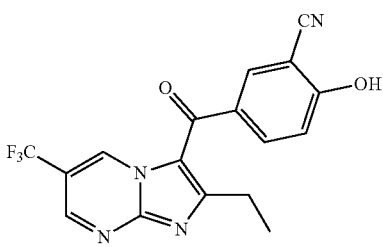 [SMILES: CCc1nc2ncc(C(F)(F)F)cn2c1C(=O)c1ccc(O)c(C#N)c1]

To a solution of (2-ethyl-6-(trifluoromethyl)imidazo[1,2-a]pyrimidin-3-yl)(3-iodo-4-hydroxyphenyl)methanone (0.8 g, 1.73 mmol) in N,N-dimethylformamide (5 mL) was added copper (I) cyanide (312 mg, 3.47 mmol). The resulting mixture was heated to 100° C. under nitrogen atmosphere, then stirred overnight. The mixture was diluted with saturated aqueous ammonium chloride (60 mL) and then dichloromethane (50 mL×3) was added for extraction. The organic phases were washed with saturated brine (20 mL), dried over anhydrous sodium sulfate, filtered and concentrated. The residue was purified by flash chromatography (petroleum ether/ethyl acetate=2/3) to give 5-(2-ethyl-6-(trifluoromethyl)imidazo[1,2-a]pyrimidine-3-carbonyl)-2-hydroxybenzonitrile (80 mg, 12%) in the form of a yellow solid. LCMS (ESI) [M+H]$^+$=361.

Step 6: Synthesis of 3-bromo-5-(2-ethyl-6-(trifluoromethyl)imidazo[1,2-a]pyrimidine-3-carbonyl)-2-hydroxybenzonitrile To a solution of 5-(2-ethyl-6-(trifluoromethyl)imidazo[1,2-a]pyrimidine-3-carbonyl)-2-hydroxybenzonitrile (80 mg, 0.22 mmol) in N,N-dimethylformamide (2 mL) was added N-bromosuccinimide (79 mg, 0.44 mmol). The mixture was stirred at room temperature for 1 h and then concentrated. The residue was purified by flash chromatography (methanol/dichloromethane=1/10) to give 3-bromo-5-(2-ethyl-6-(trifluoromethyl)imidazo[1,2-a]pyrimidine-3-carbonyl)-2-hydroxybenzonitrile (38.1 mg, 39%). LCMS (ESI) [M+H]$^+$= 439; $^1$H NMR (400 MHz, CD$_3$OD) δ 9.67 (s, 1H), 8.98 (d, J=2.4 Hz, 1H), 8.13 (d, J=2.4 Hz, 1H), 7.89 (d, J=2.0 Hz, 1H), 2.78 (q, J=7.6 Hz, 2H), 1.37 (t, J=7.6 Hz, 3H).

Example 11: Synthesis of 3-bromo-5-(3-ethyl-6-(trifluoromethyl)imidazo[1,2-a]pyrimidine-2-carbonyl)-2-hydroxybenzonitrile

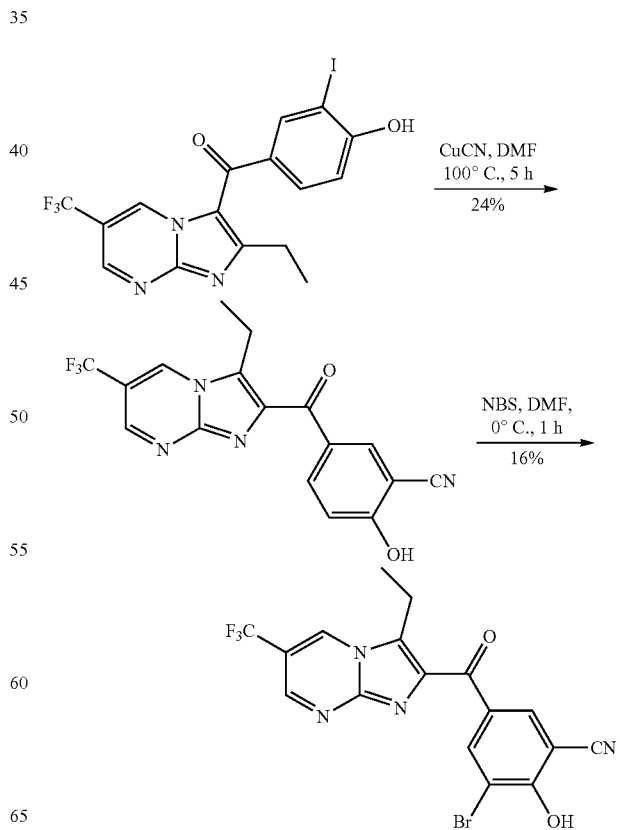

Step 1: Synthesis of 5-(3-ethyl-6-(trifluoromethyl)imidazo[1,2-a]pyrimidine-2-carbonyl)-2-hydroxybenzonitrile

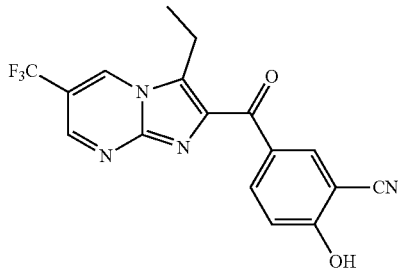 [SMILES: CCc1c(C(=O)c2ccc(O)c(C#N)c2)nc2ncc(C(F)(F)F)cn12]

To a solution of (2-ethyl-6-(trifluoromethyl)imidazo[1,2-a]pyrimidin-3-yl)(3-iodo-4-hydroxyphenyl)methanone (0.8 g, 1.73 mmol) in N,N-dimethylformamide (5 mL) was added copper (I) cyanide (312 mg, 3.47 mmol). The resulting mixture was heated to 100° C. under nitrogen atmosphere, then stirred overnight. The mixture was diluted with saturated aqueous ammonium chloride (60 mL) and then dichloromethane (50 mL×3) was added for extraction. The organic phases were washed with saturated brine (20 mL), dried over anhydrous sodium sulfate, filtered and concentrated. The residue was purified by flash chromatography (petroleum ether/ethyl acetate=2/3) to give 5-(3-ethyl-6-(trifluoromethyl)imidazo[1,2-a]pyrimidine-2-carbonyl)-2-hydroxybenzonitrile (150 mg, 24%) in the form of a yellow solid. LCMS (ESI) [M+H]$^+$=361.

Step 2: Synthesis of 3-bromo-5-(3-ethyl-6-(trifluoromethyl)imidazo[1,2-a]pyrimidine-2-carbonyl)-2-hydroxybenzonitrile

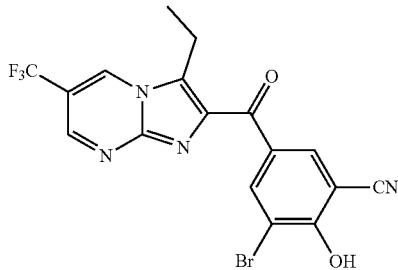 [SMILES: CCc1c(C(=O)c2cc(Br)c(O)c(C#N)c2)nc2ncc(C(F)(F)F)cn12]

To a solution of 5-(3-ethyl-6-(trifluoromethyl)imidazo[1,2-a]pyrimidine-2-carbonyl)-2-hydroxybenzonitrile (150 mg, 0.417 mmol) in N,N-dimethylformamide (3 mL) was added N-bromosuccinimide (148 mg, 0.833 mmol). The mixture was stirred at room temperature for 1 h and then concentrated. The residue was purified by flash chromatography (methanol/dichloromethane=1/10) to give 3-bromo-5-(3-ethyl-6-(trifluoromethyl)imidazo[1,2-a]pyrimidine-2-carbonyl)-2-hydroxybenzonitrile (30 mg, 16%). LCMS (ESI) [M+H]$^+$=439; $^1$H NMR (400 MHz, CD$_3$OD) δ 9.41 (s, 1H), 8.95 (d, J=2.4 Hz, 1H), 8.60 (d, J=2.0 Hz, 1H), 8.54 (s, 1H), 3.33 (q, J=7.2 Hz, 2H), 1.33 (t, J=7.6 Hz, 3H).

Example 12: Synthesis of 3-bromo-5-(2-ethyl-6-fluoroimidazo[1,2-a]pyrimidine-3-carbonyl)-2-hydroxybenzonitrile and 5-(2-ethyl-6-fluoroimidazo[1,2-a]pyrimidine-3-carbonyl)-2-hydroxyisophthalonitrile 2,2,2-trifluoroacetate

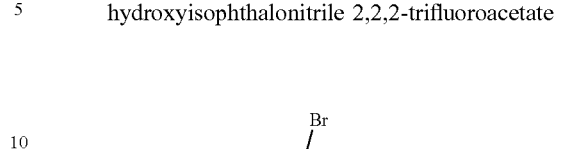

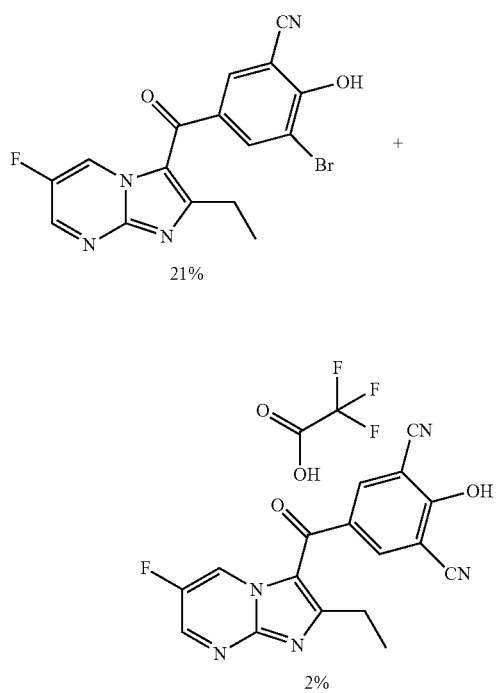

Step 1: Synthesis of 3-bromo-5-(2-ethyl-6-fluoroimidazo[1,2-a]pyrimidine-3-carbonyl)-2-hydroxybenzonitrile and 5-(2-ethyl-6-fluoroimidazo[1,2-a]pyrimidine-3-carbonyl)-2-hydroxyisophthalonitrile 2,2,2-trifluoroacetate

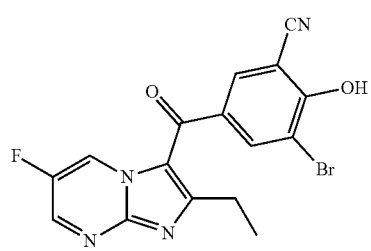

41

-continued

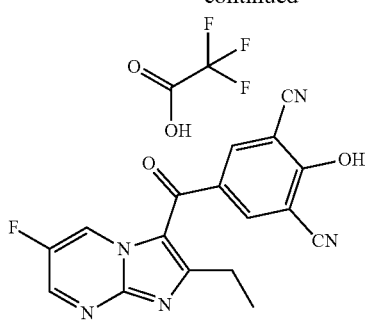

To a solution of (3,5-dibromo-4-hydroxyphenyl)(2-ethyl-6-fluoroimidazo[1,2-a]pyrimidin-3-yl)methanone (66 mg, 0.15 mmol) in 1-methyl-2-pyrrolidinone (2 mL) was added copper (I) cyanide (27 mg, 0.3 mmol) and then the mixture was stirred at 140° C. under microwave for 3 h. The mixture was diluted with saturated aqueous ammonium chloride (20 mL) and then ethyl acetate (20 mL×3) was added for extraction. The organic phases were washed with saturated brine, dried over anhydrous sodium sulfate, filtered and concentrated. The residue was purified by Prep-TLC (methanol/dichloromethane=1/9) to give a compound of 3-bromo-5-(2-ethyl-6-fluoroimidazo[1,2-a]pyrimidine-3-carbonyl)-2-hydroxybenzonitrile and 5-(2-ethyl-6-fluoroimidazo[1,2-a]pyrimidine-3-carbonyl)-2-hydroxyisophthalonitrile 2,2,2-trifluoroacetate, which was further purified by Pre-HPLC to give 3-bromo-5-(2-ethyl-6-fluoroimidazo[1,2-a]pyrimidine-3-carbonyl)-2-hydroxybenzonitrile (12 mg, 21%), LCMS (ESI) [M+H]$^+$=389; $^1$H NMR (400 MHz, CD$_3$OD) δ 9.22-9.24 (m, 1H), 8.69 (d, J=2.8 Hz, 1H), 7.95 (d, J=2.4 Hz, 1H), 7.70 (d, J=2.0 Hz, 1H), 2.65 (q, J=7.6 Hz, 2H), 1.21 (t, J=7.6 Hz, 3H);

and 5-(2-ethyl-6-fluoroimidazo[1,2-a]pyrimidine-3-carbonyl)-2-hydroxyisophthalonitrile 2,2,2-trifluoroacetate (1.6 mg, 2%). LCMS (ESI) [M-TFA+H]$^+$=336; $^1$H NMR (400 MHz, CD$_3$OD) δ 9.57-9.59 (m, 1H), 8.95 (d, J=2.8 Hz, 1H), 8.20 (s, 2H), 2.70 (q, J=7.2 Hz, 2H), 1.32 (t, J=7.6 Hz, 3H).

Example 13: Synthesis of 3-bromo-5-(2-ethyl-6-fluoroimidazo[1,2-a]pyrimidine-3-carbonyl)-2-hydroxybenzonitrile and (3,5-dibromo-4-hydroxyphenyl)(3-ethyl-6-fluoroimidazo[1,2-a]pyrimidin-2-yl)methanone

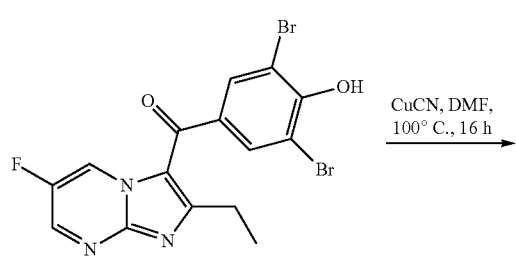

42

-continued

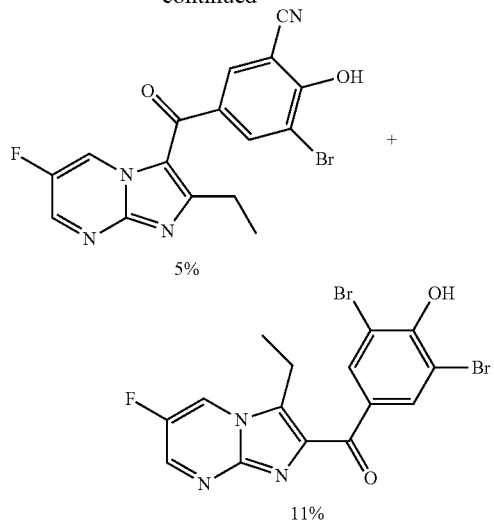

Step 1: Synthesis of 3-bromo-5-(2-ethyl-6-fluoroimidazo[1,2-a]pyrimidine-3-carbonyl)-2-hydroxybenzonitrile and (3,5-dibromo-4-hydroxyphenyl)(3-ethyl-6-fluoroimidazo[1,2-a]pyrimidin-2-yl)methanone

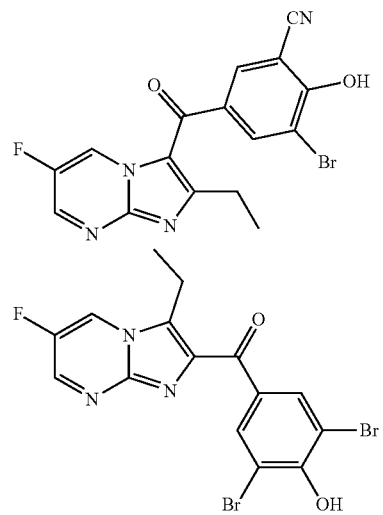

To a solution of (3,5-dibromo-4-hydroxyphenyl)(2-ethyl-6-fluoroimidazo[1,2-a]pyrimidin-3-yl)methanone (220 mg, 0.5 mmol) in N,N-dimethylformamide (2 mL) was added copper (I) cyanide (40 mg, 0.45 mmol). The mixture was heated to 100° C. under nitrogen atmosphere, then stirred for 16 h. The mixture was diluted with saturated aqueous ammonium chloride (60 mL) and then dichloromethane (50 mL×3) was added for extraction. The organic phases were washed with saturated brine, dried over anhydrous sodium sulfate, filtered and concentrated. The residue was purified by Prep-HPLC to give 3-bromo-5-(2-ethyl-6-fluoroimidazo[1,2-a]pyrimidine-3-carbonyl)-2-hydroxybenzonitrile (10 mg, 5%), LCMS (ESI) [M+H]$^+$=389; $^1$H NMR (400 MHz, CD$_3$OD) δ 9.61 (dd, J=4.4 Hz, 1H), 8.91 (d, J=3.2 Hz, 1H), 8.20 (d, J=2.4 Hz, 1H), 8.01 (d, J=2.0 Hz, 1H), 2.60 (q, J=7.6 Hz, 2H), 1.27 (t, J=7.2 Hz, 3H);

and (3,5-dibromo-4-hydroxyphenyl)(3-ethyl-6-fluoroimidazo[1,2-a]pyrimidin-2-yl) methanone (25 mg, 11%). LCMS (ESI) [M+H]$^+$=441; $^1$H NMR (400 MHz, DMSO-d$_6$) δ 11.01 (bs, 1H), 9.38 (dd, J=4.4 Hz, 1H), 8.90 (d, J=2.8 Hz, 1H), 8.59 (s, 2H), 3.24 (q, J=7.2 Hz, 2H), 1.21 (t, J=7.2 Hz, 3H).

Example 14: Synthesis of 3-bromo-5-(2-ethyl-6-fluoroimidazo[1,2-a]pyrimidine-3-carbonyl)-2-hydroxybenzonitrile

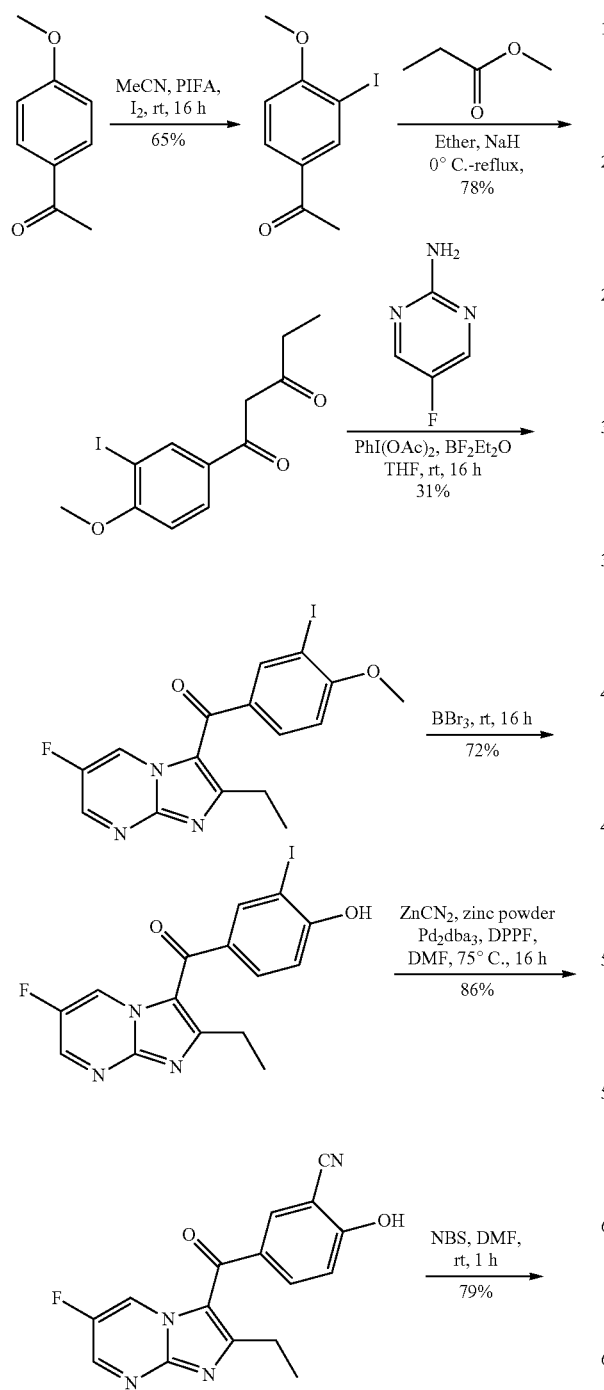

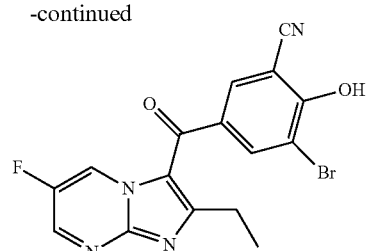

Step 1: Synthesis of 1-(3-iodo-4-methoxyphenyl)ethanone

A solution of 1-(4-methoxyphenyl)ethanone (15 g, 100 mmol), phenyliodine (III) bis(trifluoroacetate) (47.3 g, 110 mmol) and iodine (25.2 g, 100 mmol) in acetonitrile (300 mL) was stirred at room temperature for 16 h. The mixture was diluted with water (400 mL) and washed with aqueous sodium sulfite (100 mL×2), and then ethyl acetate (100 mL×4) was added for extraction. The organic phases were washed with saturated brine (150 mL), dried over anhydrous sodium sulfate, filtered and concentrated. The residue was purified by flash chromatography (petroleum ether/ethyl acetate=1/1) to give 1-(3-iodo-4-methoxyphenyl) ethanone (18 g, 65%) in the form of a yellow solid. LCMS (ESI) [M+H]$^+$=277.

Step 2: Synthesis of 1-(3-iodo-4-methoxyphenyl)pentane-1,3-dione

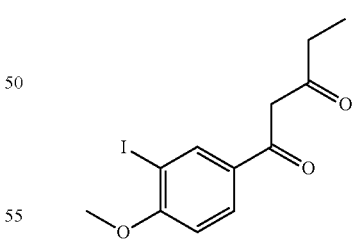

To a solution of sodium hydride (5 g, 60% in oil, 125 mmol) in diethyl ether (200 mL) was added a solution of 1-(3-iodo-4-methoxyphenyl)ethanone (13.8 g, 50 mmol) in diethyl ether (50 mL) dropwise at 0° C. Ethyl propionate (10.2 g, 100 mmol) was then added rapidly, and the resulting mixture was heated under reflux for 16 h. After cooling to room temperature, the mixture was diluted with water (400 mL). The pH value was adjusted to 5 with concentrated hydrochloric acid. Ethyl acetate (50 mL×4) was added for extraction. The organic phases were washed with saturated brine (150 mL), dried over anhydrous sodium sulfate, filtered and concentrated. The residue was purified by flash chromatography (petroleum ether/ethyl acetate=3/1) to give 1-(3-iodo-4-methoxyphenyl)pentane-1,3-dione (13 g, 78%) in the form of a yellow solid. LCMS (ESI) [M+H]$^+$=333.

Step 3: Synthesis of (2-ethyl-6-fluoroimidazo[1,2-a]pyrimidin-3-yl)(3-iodo-4-methoxyphenyl) methanone

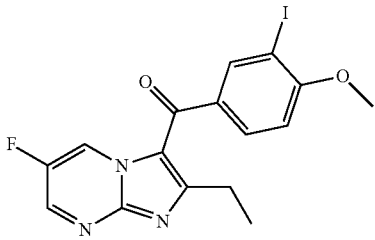 [SMILES: CCc1nc2ncc(F)cn2c1C(=O)c1ccc(OC)c(I)c1]

A solution of 1-(3-iodo-4-methoxyphenyl)pentane-1,3-dione (6.2 g, 18.6 mmol), (diacetoxyiodo)benzene (9 g, 27.9 mmol), and 5-fluoropyrimidin-2-amine (2.11 g, 18.6 mmol) in tetrahydrofuran (100 mL) was stirred at room temperature for 1 h. Then boron trifluoride etherate (0.53 g, 3.73 mmol) was added, and the resulting mixture was stirred at room temperature overnight and then concentrated. The residue was purified by flash chromatography (petroleum ether/ethyl acetate=1/3) to give (2-ethyl-6-fluoroimidazo[1,2-a]pyrimidin-3-yl) (3-iodo-4-methoxyphenyl)methanone (2.5 g, 31%) in the form of a yellow solid. LCMS (ESI) [M+H]$^+$=426.

Step 4: Synthesis of (2-ethyl-6-fluoroimidazo[1,2-a]pyrimidin-3-yl)(4-hydroxy-3-iodophenyl) methanone

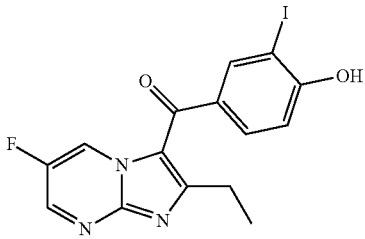 [SMILES: CCc1nc2ncc(F)cn2c1C(=O)c1ccc(O)c(I)c1]

To a solution of (2-ethyl-6-fluoroimidazo[1,2-a]pyrimidin-3-yl)(3-iodo-4-methoxyphenyl) methanone (2 g, 4.7 mmol) in dichloromethane (3 mL) was added boron tribromide (6 mL, 99%) at 0° C. The mixture was stirred at room temperature for 16 h. The mixture was slowly poured into ice and the pH value was adjusted to 9 with aqueous sodium bicarbonate (30 mL) at 0° C. The resulting mixture was stirred at room temperature for 1 h and then concentrated. The filter cake was washed with water (50 mL), ethyl acetate (10 mL) and petroleum ether (50 mL), then dried to give (2-ethyl-6-fluoroimidazo[1,2-a]pyrimidin-3-yl)(4-hydroxy-3-iodophenyl) methanone (1.4 g, 72%) in the form of a yellow solid, which was directly used in the next step without purification. LCMS (ESI) [M+H]$^+$=412.

Step 5: Synthesis of 5-(2-ethyl-6-fluoroimidazo[1,2-a]pyrimidine-3-carbonyl)-2-hydroxybenzonitrile

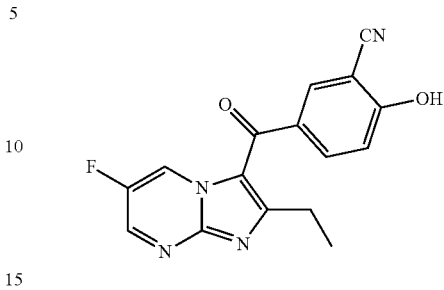

A solution of (2-ethyl-6-fluoroimidazo[1,2-a]pyrimidin-3-yl)(4-hydroxy-3-iodophenyl) methanone (1.4 g, 3.4 mmol), zinc cyanide (598 mg, 5.1 mmol), zinc powder (44 mg, 0.68 mmol), tris(dibenzylideneacetone)dipalladium (155 mg, 0.17 mmol) and 1,1'-ferrocenebis (diphenylphosphine) (94 mg, 0.17 mmol) in N,N-dimethylformamide (10 mL) was heated to 75° C. under nitrogen atmosphere and then stirred for 16 h. The reaction was quenched with saturated aqueous ammonium chloride (50 mL), and the mixture was diluted with dichloromethane (100 mL) and then filtered. The filter cake was washed with dichloromethane (50 mL) and methanol (10 mL), then dried to give 5-(2-ethyl-6-fluoroimidazo[1,2-a]pyrimidine-3-carbonyl)-2-hydroxybenzonitrile (910 mg, 86%) in the form of a yellow solid. LCMS (ESI) [M+H]$^+$=311.

Step 6: Synthesis of 3-bromo-5-(2-ethyl-6-fluoroimidazo[1,2-a]pyrimidine-3-carbonyl)-2-hydroxybenzonitrile

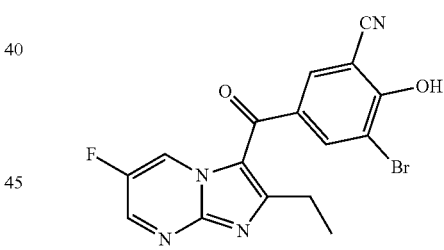

To a solution of 5-(2-ethyl-6-fluoroimidazo[1,2-a]pyrimidine-3-carbonyl)-2-hydroxybenzonitrile (910 mg, 2.93 mmol) in N,N-dimethylformamide (5 mL) was added N-bromosuccinimide (627 mg, 3.5 mmol). The mixture was stirred at room temperature for 1 h and then the reaction was quenched with water (25 mL). The mixture was filtered and the filter cake was washed with water (30 mL) and methanol (10 mL). The filtrate was extracted with ethyl acetate (30 mL×4), and the organic phases were concentrated. The residue and the filter cake was diluted with methanol (100 mL) and stirred at room temperature for 30 min. The mixture was filtered and the filter cake was washed with dichloromethane (50 mL), methanol (10 mL) and ethyl acetate (100 mL). The filtrate was concentrated and purified by Prep-TLC twice (methanol/dichloromethane=0 to 15%) to give 3-bromo-5-(2-ethyl-6-fluoroimidazo[1,2-a]pyrimidine-3-carbonyl)-2-hydroxybenzonitrile (900 mg, 79%). LCMS (ESI) [M+H]$^+$=389; $^1$H NMR (400 MHz, CD$_3$OD) δ 9.35

(dd, J=4.4 Hz, 1H), 8.80 (d, J=3.2 Hz, 1H), 8.06 (d, J=2.4 Hz, 1H), 7.82 (d, J=2.0 Hz, 1H), 2.77 (q, J=7.6 Hz, 2H), 1.33 (t, J=7.6 Hz, 3H).

Example 15: Synthesis of 3-bromo-5-(3-ethyl-6-fluoroimidazo[1,2-a]pyrimidine-2-carbonyl)-2-hydroxybenzonitrile

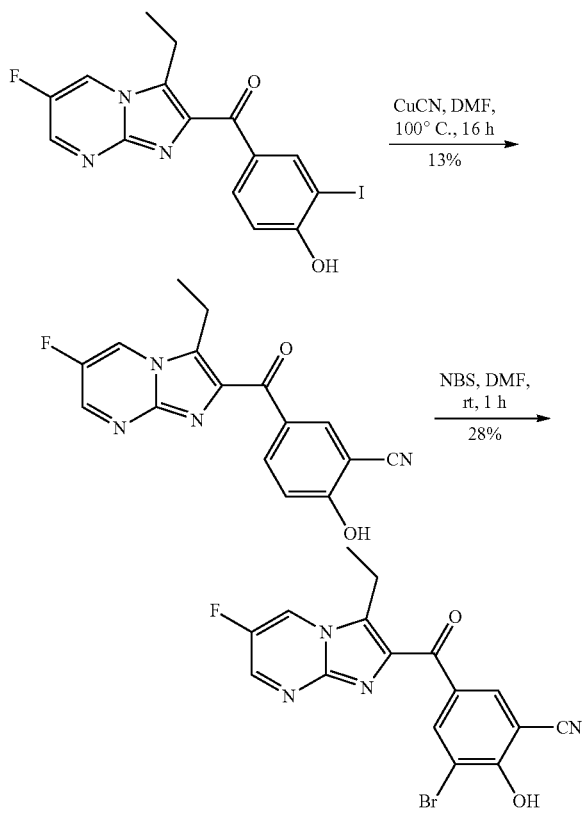

Step 1: Synthesis of 5-(3-ethyl-6-fluoroimidazo[1,2-a]pyrimidine-2-carbonyl)-2-hydroxybenzonitrile To a solution of (3-ethyl-6-fluoroimidazo[1,2-a]pyrimidin-2-yl)(4-hydroxy-3-iodophenyl) methanone (5 g, 12.1 mmol) in N,N-dimethylformamide (10 mL) was added copper (I) cyanide (2.19 g, 24.2 mmol). The resulting mixture was heated to 100° C. under nitrogen atmosphere and then stirred for 16 h. The mixture was poured into methanol (50 mL). The mixture was filtered and the filter cake was washed with methanol (10 mL). The filtrate was collected and concentrated, and the residue was purified by flash chromatography (ethyl acetate) to give 5-(3-ethyl-6-fluoroimidazo[1,2-a]pyrimidine-2-carbonyl)-2-hydroxybenzonitrile (500 mg, 13%) in the form of a yellow solid. LCMS (ESI) [M+H]$^+$=311.

Step 2: Synthesis of 3-bromo-5-(3-ethyl-6-fluoroimidazo[1,2-a]pyrimidine-2-carbonyl)-2-hydroxybenzonitrile To a solution of 5-(3-ethyl-6-fluoroimidazo[1,2-a]pyrimidine-2-carbonyl)-2-hydroxybenzonitrile (500 mg, 1.61 mmol) in N,N-dimethylformamide (3 mL) was added N-bromosuccinimide (574 mg, 3.22 mmol). The mixture was stirred at room temperature for 1 h and then the reaction was quenched with water (20 mL). The mixture was filtered and the filter cake was purified by Prep-HPLC to give 3-bromo-5-(3-ethyl-6-fluoroimidazo[1,2-a]pyrimidine-2-carbonyl)-2-hydroxybenzonitrile (175 mg, 28%). LCMS (ESI) [M+H]$^+$=389; $^1$H NMR (400 MHz, CD$_3$OD) δ 9.11 (dd, J=4.0 Hz, 1H), 8.80 (d, J=2.4 Hz, 1H), 8.74 (d, J=2.0 Hz, 1H), 8.64 (d, J=2.0 Hz, 1H), 3.33 (q, J=7.6 Hz, 2H), 1.33 (t, J=7.6 Hz, 3H).

Example 16: Synthesis of (3,5-dibromo-4-hydroxyphenyl)(2-ethyl-2H-pyrazolo[4,3-c]pyridin-3-yl)methanone

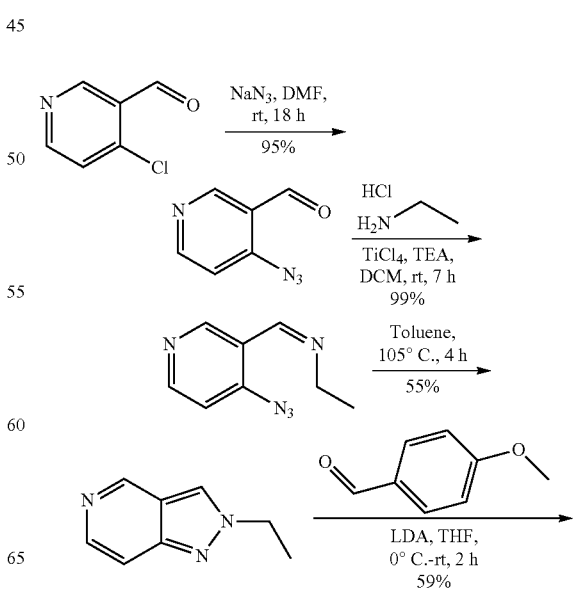

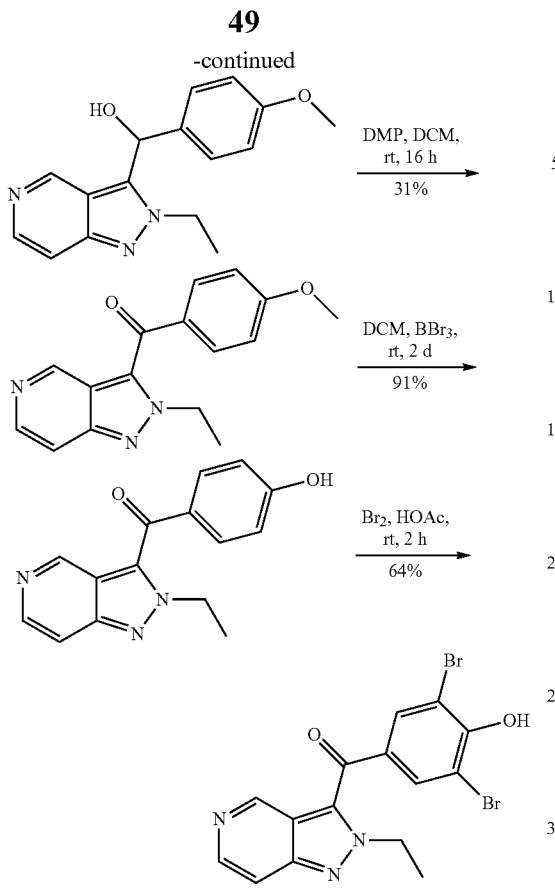

Step 1: Synthesis of 4-azidonicotinaldehyde

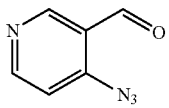

To a solution of 4-chloropyridine-3-carboxaldehyde (1 g, 7.06 mmol) in N,N-dimethylformamide (10 mL) was added sodium azide (459 mg, 7.06 mmol), and the mixture was stirred at room temperature for 16 h. The mixture was diluted with ethyl acetate (100 mL), then washed with water (20 mL×2), dried over anhydrous sodium sulfate, filtered and concentrated to give 4-azidonicotinaldehyde (1 g, 95%) in the form of a yellow solid, which was directly used in the next step without purification. LCMS (ESI) [M+H]$^+$=121.

Step 2: Synthesis of N-((4-azidopyridin-3-yl)methylene)ethanamine

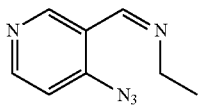

A solution of 4-azidonicotinaldehyde (1 g, 6.76 mmol), titanium tetrachloride (4 mL, 1 M in dichloromethane, 4 mmol) and ethanamine hydrochloride (551 mg, 6.76 mmol) in dichloromethane (10 mL) was stirred at room temperature for 7 h. The mixture was concentrated, and the residue was diluted with ethyl acetate (100 mL), then washed with water (20 mL×2), dried over anhydrous sodium sulfate, filtered and concentrated to give N-((4-azidopyridin-3-yl)methylene)ethanamine (1.2 g, 99%) in the form of a yellow solid, which was used directly in the next step without purification. LCMS (ESI) [M-28+H]$^+$=148.

Step 3: Synthesis of 2-ethyl-2H-pyrazolo[4,3-c]pyridine

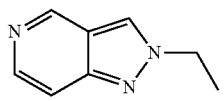

A solution of N-((4-azidopyridin-3-yl)methylene)ethanamine (1.2 g, 6.76 mmol) in toluene (60 mL) was stirred at 105° C. for 4 h. The mixture was concentrated, and the residue was purified by flash chromatography (petroleum ether/ethyl acetate=1/3) to give 2-ethyl-2H-pyrazolo[4,3-c]pyridine (0.55 g, 55%) in the form of a yellow oil. LCMS (ESI) [M+H]$^+$=148.0.

Step 4: Synthesis of (2-ethyl-2H-pyrazolo[4,3-c]pyridin-3-yl)(4-methoxyphenyl)methanol

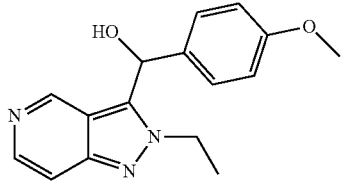 [SMILES: CCn1nc2ccncc2c1C(=O)c1ccc(OC)cc1]

To a solution of 2-ethyl-2H-pyrazolo[4,3-c]pyridine (0.3 g, 2.04 mmol) in anhydrous tetrahydrofuran (30 mL) was added lithium diisopropylamide (1.23 mL, 2 M, 2.45 mmol) dropwise at 0° C. under argon atmosphere. The mixture was stirred at 0° C. for 1 h and then cooled to −78° C. 4-methoxybenzaldehyde (278 mg, 2.04 mmol) was then added dropwise to the mixture. The resulting mixture was stirred at room temperature for 1 h. The reaction was quenched with water (100 mL) and then ethyl acetate (50 mL×3) was added for extraction. The organic phases were washed with saturated brine, dried over anhydrous sodium sulfate, filtered and concentrated. The residue was purified by flash chromatography (petroleum ether/ethyl acetate=1/3) to give (2-ethyl-2H-pyrazolo[4,3-c]pyridin-3-yl)(4-methoxyphenyl)methanol (340 mg, 59%) in the form of a colorless oil. LCMS (ESI) [M+H]$^+$=284.

Step 5: Synthesis of (2-ethyl-2H-pyrazolo[4,3-c]pyridin-3-yl)(4-methoxyphenyl)methanone

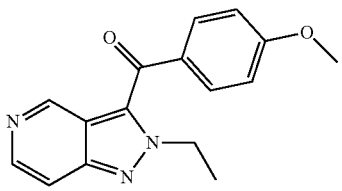

To a solution of (2-ethyl-2H-pyrazolo[4,3-c]pyridin-3-yl)(4-methoxyphenyl)methanol (0.34 g, 1.2 mmol) in dichloromethane (10 mL) was added Dess-Martin oxidant (1 g, 2.4 mmol) at 0° C. The mixture was stirred at room temperature for 16 h and then concentrated. The residue was purified by flash chromatography (petroleum ether/ethyl acetate=3/1) to give (2-ethyl-2H-pyrazolo[4,3-c]pyridin-3-yl)(4-methoxyphenyl)methanone (180 mg, 31%) in the form of a white solid. LCMS (ESI) [M+H]$^+$=282.

Step 6: Synthesis of (2-ethyl-2H-pyrazolo[4,3-c]pyridin-3-yl)(4-hydroxyphenyl)methanone

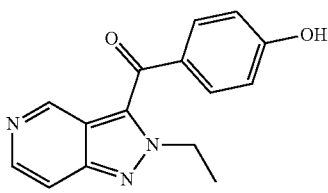 [SMILES: CCn1nc2ccncc2c1C(=O)c1ccc(O)cc1]

To a solution of (2-ethyl-2H-pyrazolo[4,3-c]pyridin-3-yl)(4-methoxyphenyl)methanone (90 mg, 0.32 mmol) in anhydrous dichloromethane (2 mL) was added boron tribromide (2 mL, 17% in dichloromethane) at 0° C. under nitrogen atmosphere. The mixture was stirred at room temperature for 2 days. The mixture was slowly added to saturated aqueous sodium bicarbonate (100 mL) at 0° C. and then ethyl acetate (30 mL×3) was added for extraction. The organic phases were washed with saturated brine (150 mL), dried over anhydrous sodium sulfate, filtered and concentrated to give (2-ethyl-2H-pyrazolo[4,3-c]pyridin-3-yl)(4-hydroxyphenyl) methanone (78 mg, 91%) in the form of a white solid, which was directly used in the next step without purification. LCMS (ESI) [M+H]$^+$=268.

Step 7: Synthesis of (3,5-dibromo-4-hydroxyphenyl)(2-ethyl-2H-pyrazolo[4,3-c]pyridin-3-yl) methanone

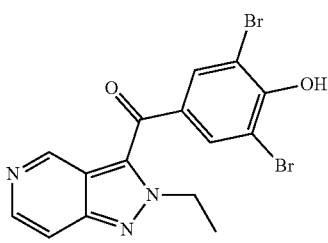 [SMILES: CCn1nc2ccncc2c1C(=O)c1cc(Br)c(O)c(Br)c1]

To a solution of (2-ethyl-2H-pyrazolo[4,3-c]pyridin-3-yl)(4-hydroxyphenyl)methanone (72 mg, 0.29 mmol) in acetic acid (2 mL) was added bromine water (186 mg, 1.17 mmol) at 0° C. The mixture was stirred at room temperature for 2 h. The mixture was concentrated and the residue was purified by Prep-HPLC to give (3,5-dibromo-4-hydroxyphenyl)(2-ethyl-2H-pyrazolo[4,3-c]pyridin-3-yl)methanone (80 mg, 64%). LCMS (ESI) [M+H]$^+$=424; $^1$H NMR (400 MHz, CD$_3$OD) δ 8.81 (d, J=0.9 Hz, 1H), 8.28 (d, J=6.4 Hz, 1H), 7.99 (s, 2H), 7.76 (dd, J=6.4 Hz, 1H), 4.74 (q, J=7.2 Hz, 2H), 1.64 (t, J=7.2 Hz, 3H).

Example 17: Synthesis of 3-bromo-5-(2-ethyl-7-(trifluoromethyl)imidazo[1,2-a]pyrimidine-3-carbonyl)-2-hydroxybenzonitrile

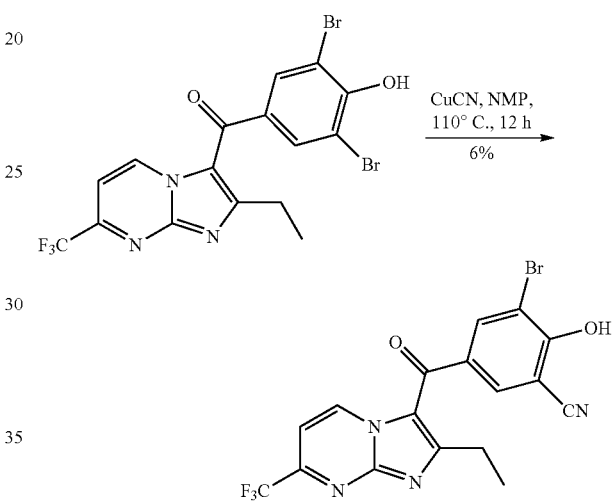

Step 1: Synthesis of 3-bromo-5-(2-ethyl-7-(trifluoromethyl)imidazo[1,2-a]pyrimidine-3-carbonyl)-2-hydroxybenzonitrile

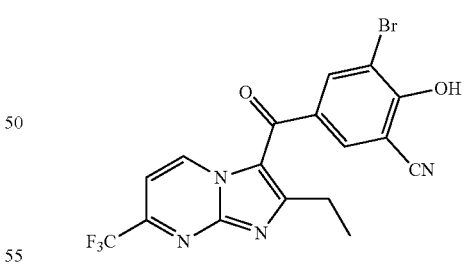

To a solution of (3,5-dibromo-4-hydroxyphenyl)(2-ethyl-7-(trifluoromethyl)imidazo[1,2-a]pyrimidin-3-yl)methanone (100 mg, 0.2 mmol) in 1-methyl-2-pyrrolidinone (5.0 mL) was slowly added copper (I) cyanide (36 mg, 0.40 mmol). The mixture was stirred at 110° C. for 12 h, then concentrated. The residue was purified by Prep-HPLC to give 3-bromo-5-(2-ethyl-7-(trifluoromethyl)imidazo[1,2-a]pyrimidine-3-carbonyl)-2-hydroxybenzonitrile (6 mg, 6%). LCMS (ESI) [M+H]$^+$=439; $^1$H NMR (400 MHz, DMSO-d$_6$) δ 9.75-9.74 (m, 1H), 8.24-8.23 (m, 1H), 8.05 (s, 1H), 7.68-7.66 (m, 1H), 2.67 (q, 2H), 1.32 (t, 3H).

Example 18: Synthesis of (3-bromo-4-hydroxy-5-(trifluoromethyl)phenyl)(2-ethyl-6-fluoroimidazo[1,2-a]pyrimidin-3-yl)methanone

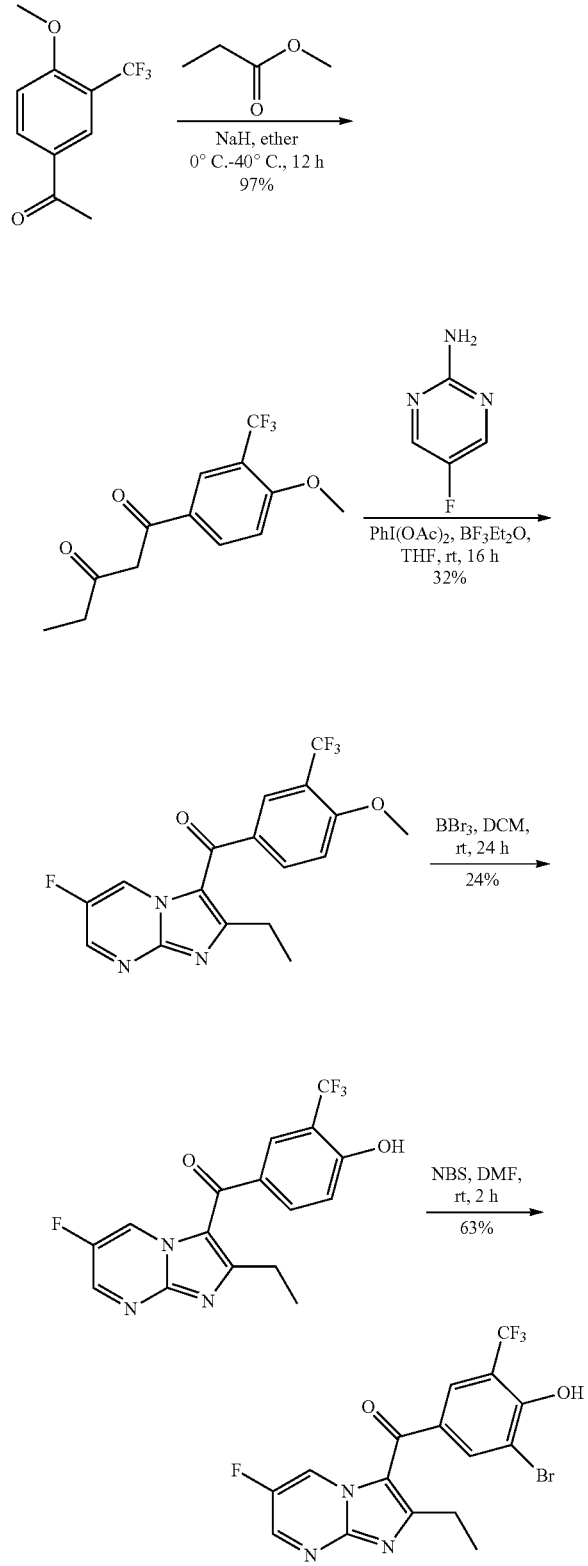

Step 1: Synthesis of 1-(4-methoxy-3-(trifluoromethyl)phenyl)pentane-1,3-dione

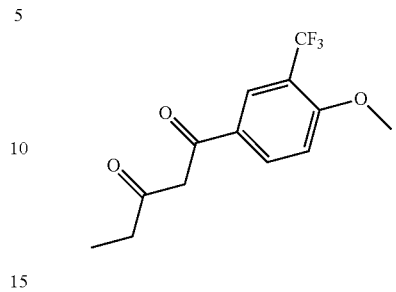

To a solution of 1-(4-methoxy-3-(trifluoromethyl)phenyl)ethanone (4.00 g, 18.34 mmol) in diethyl ether (200 mL) was added sodium hydride (60% in oil, 2.00 g, 180.34 mmol) at 0° C. and the mixture was stirred at 0° C. for 30 min. Methyl propionate (2.422 g, 27.5 mmol) was added, and the resulting mixture was stirred at 40° C. for 12 h. The reaction was quenched with water, and then ethyl acetate (20 mL×3) was added for extraction. The organic phases were washed with water (20 mL×2), dried over anhydrous sodium sulfate, filtered and concentrated. The residue was purified by flash chromatography (petroleum ether/ethyl acetate=3/1) to give 1-(4-methoxy-3-(trifluoromethyl)phenyl)pentane-1,3-dione (3.9 g, 97%) in the form of a yellow oil. LCMS (ESI) [M+H]$^+$=275.

Step 2: Synthesis of (2-ethyl-6-fluoroimidazo[1,2-a]pyrimidin-3-yl)(4-methoxy-3-(trifluoromethyl)phenyl)methanone

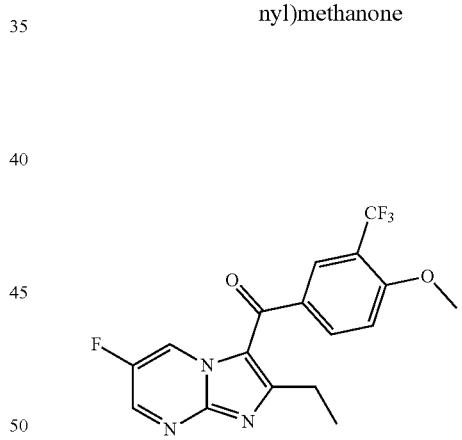

A solution of 1-(4-methoxy-3-(trifluoromethyl)phenyl)pentane-1,3-dione (2.0 g, 5.3 mmol), 5-fluoropyrimidin-2-amine (0.723 g, 6.4 mmol) and (diacetoxyiodo)benzene (2.55 g, 7.95 mmol) in tetrahydrofuran (40 mL) was stirred at 7° C. for 2 h. Then boron trifluoride etherate (0.149 g, 1.00 mmol) was added, and the resulting mixture was stirred overnight at room temperature. The reaction was quenched with water, and then ethyl acetate (20 mL×3) was added for extraction. The organic phases were washed with water (20 mL×2), dried over anhydrous sodium sulfate, filtered and concentrated. The residue was purified by flash chromatography (petroleum ether/ethyl acetate=3/1) to give (2-ethyl-6-fluoroimidazo[1,2-a]pyrimidin-3-yl)(4-methoxy-3-(trifluoromethyl)phenyl)methanone (640 mg, 32%) in the form of a yellow oil. LCMS (ESI) [M+H]$^+$=368.

Step 3: Synthesis of (2-ethyl-6-fluoroimidazo[1,2-a]pyrimidin-3-yl)(4-hydroxy-3-(trifluoromethyl)phenyl)methanone

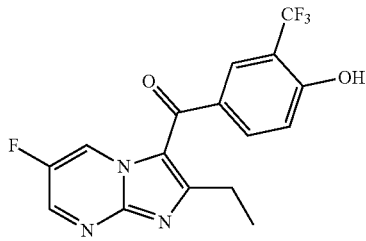

To a solution of (2-ethyl-6-fluoroimidazo[1,2-a]pyrimidin-3-yl)(4-hydroxy-3-(trifluoromethyl)phenylmethanone (610 mg, 1.66 mmol) in dichloromethane (2 mL) was added boron tribromide (17% in dichloromethane, 20 mL). The mixture was stirred at room temperature for 24 h. The reaction was quenched with water and then ethyl acetate (20 mL×3) was added for extraction. The organic phases were washed with water (20 mL×2), dried over anhydrous sodium sulfate, filtered and concentrated to give (2-ethyl-6-fluoroimidazo[1,2-a]pyrimidin-3-yl)(4-hydroxy-3-(trifluoromethyl)phenyl)methanone (150 mg, 24%) in the form of a brown solid. LCMS (ESI) [M+H]$^+$=354.

Step 4: Synthesis of (3-bromo-4-hydroxy-5-(trifluoromethyl)phenyl)(2-ethyl-6-fluoroimidazo[1,2-a]pyrimidin-3-yl)methanone

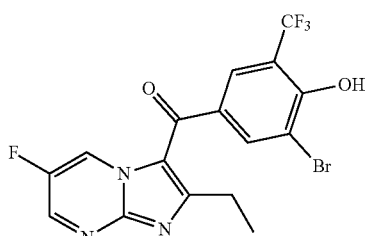

To a solution of (2-ethyl-6-fluoroimidazo[1,2-a]pyrimidin-3-yl)(4-hydroxy-3-(trifluoromethyl)phenyl)methanone (80 mg, 0.22 mmol) in N,N-dimethylformamide (4.5 mL) was added N-bromosuccinimide (120 mg, 0.67 mmol) slowly at 0° C. The mixture was stirred at room temperature for 2 h. The mixture was concentrated and the residue was purified by Prep-HPLC to give (3-bromo-4-hydroxy-5-(trifluoromethyl)phenyl)(2-ethyl-6-fluoroimidazo[1,2-a]pyrimidin-3-yl)methanone (60 mg, 63%). LCMS (ESI) [M+H]$^+$=432; $^1$H NMR (400 MHz, DMSO-d$_6$) δ 9.52-9.50 (m, 1H), 8.99 (s, 1H), 8.18-8.18 (m, 1H), 7.91-7.90 (m, 1H), 2.49 (q, 2H), 1.18 (t, 3H).

Example 19: Synthesis of (3-bromo-4-hydroxy-5-(trifluoromethyl)phenyl)(2-ethyl-6-(trifluoromethyl)imidazo[1,2-a]pyrimidin-3-yl)methanone

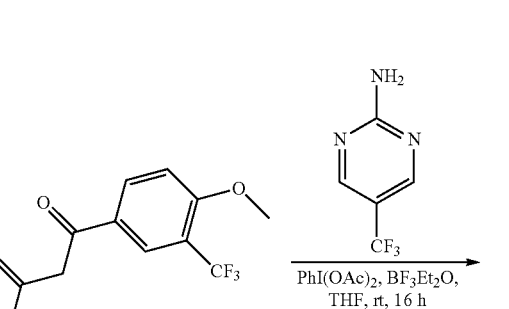

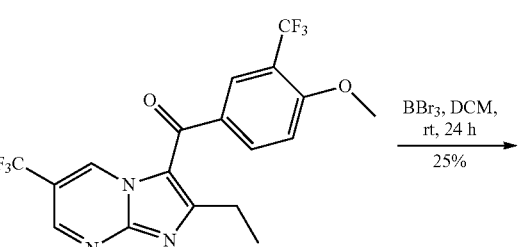

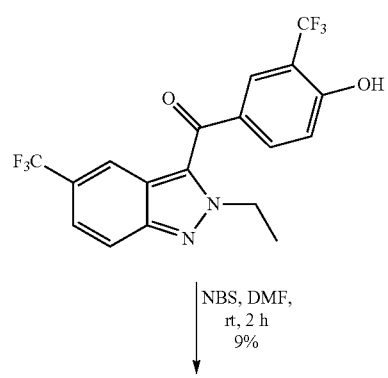

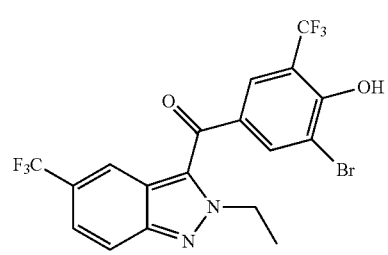

Step 1: Synthesis of (2-ethyl-6-(trifluoromethyl)imidazo[1,2-a]pyrimidin-3-yl)(4-methoxy-3-(trifluoromethyl)phenyl)methanone

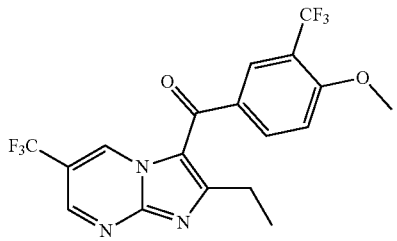 [SMILES: CCc1nc2ncc(C(F)(F)F)cn2c1C(=O)c1ccc(OC)c(C(F)(F)F)c1]

A solution of 1-(4-methoxy-3-(trifluoromethyl)phenyl)pentane-1,3-dione (1.5 g, 4.02 mmol), 5-(trifluoromethyl)pyrimidin-2-amine (0.78 g, 4.8 mmol) and (diacetoxyiodo)benzene (1.93 g, 6.0 mmol) in tetrahydrofuran (40 mL) was stirred at room temperature for 2 h. Then boron trifluoride etherate (0.111 g, 1.00 mmol) was added, and the resulting mixture was stirred overnight at room temperature. The reaction was quenched with water, and then ethyl acetate (20 mL×3) was added for extraction. The organic phases were washed with water (20 mL×2), dried over anhydrous sodium sulfate, filtered and concentrated. The residue was purified by flash chromatography (petroleum ether/ethyl acetate=3/1) to give (2-ethyl-6-(trifluoromethyl) imidazo[1,2-a]pyrimidin-3-yl)(4-methoxy-3-(trifluoromethyl)phenyl)methanone (400 mg, 26%) in the form of a yellow oil. LCMS (ESI) [M+H]$^+$=418.

Step 2: Synthesis of (2-ethyl-6-(trifluoromethyl)imidazo[1,2-a]pyrimidin-3-yl)(4-hydroxy-3-(trifluoromethyl)phenyl)methanone

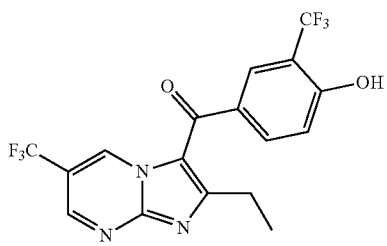 [SMILES: CCc1nc2ncc(C(F)(F)F)cn2c1C(=O)c1ccc(O)c(C(F)(F)F)c1]

To a solution of (2-ethyl-6-(trifluoromethyl)imidazo[1,2-a]pyrimidin-3-yl)(4-methoxy-3-(trifluoromethyl)phenyl)methanone (400 mg, 0.95 mmol) in dichloromethane (2 mL) was added boron tribromide (17% in dichloromethane, 20 mL). The mixture was stirred at room temperature for 24 h. The reaction was quenched with water and then ethyl acetate (20 mL×3) was added for extraction. The organic phases were washed with water (20 mL×2), dried over anhydrous sodium sulfate, filtered and concentrated to give (2-ethyl-6-(trifluoromethyl)imidazo[1,2-a]pyrimidin-3-yl)(4-hydroxy-3-(trifluoromethyl)phenyl)methanone (100 mg, 25%) in the form of a brown solid. LCMS (ESI) [M+H]$^+$=404.

Step 3: Synthesis of (3-bromo-4-hydroxy-5-(trifluoromethyl)phenyl)(2-ethyl-6-(trifluoromethyl) imidazo[1,2-a]pyrimidin-3-yl)methanone To a solution of (2-ethyl-6-(trifluoromethyl)imidazo[1,2-a]pyrimidin-3-yl)(4-hydroxy-3-(trifluoromethyl)phenyl)methanone (90 mg, 0.22 mmol) in N,N-dimethylformamide (4.5 mL) was added N-bromosuccinimide (120 mg, 0.67 mmol) slowly at 0° C. The mixture was stirred at room temperature for 2 h, then concentrated. The residue was purified by Prep-HPLC to give (3-bromo-4-hydroxy-5-(trifluoromethyl)phenyl)(2-ethyl-6-(trifluoromethyl)imidazo[1,2-a]pyrimidin-3-yl)methanone (8.1 mg, 9%). LCMS (ESI) [M+H]$^+$=482; $^1$H NMR (400 MHz, DMSO-d$_6$) δ 9.60 (s, 1H), 9.13 (s, 1H), 8.16 (s, 1H), 7.90 (s, 1H), 2.55 (q, 2H), 1.23 (t, 3H).

Example 20: Synthesis of 2,6-dibromo-4-([2-ethyl-imidazo[1,2-a]pyrimidin-3-yl]carbonyl) phenol

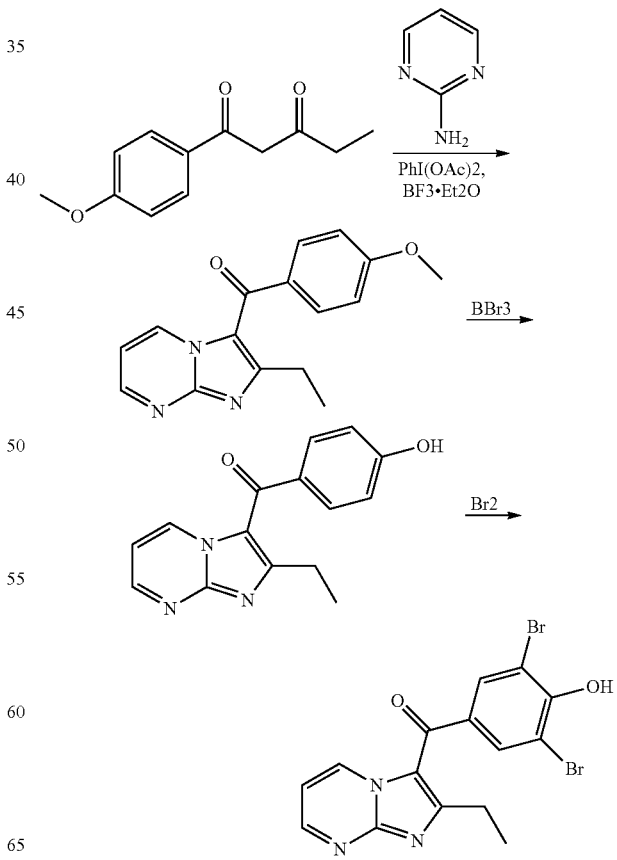

Step 1: Synthesis of 2-ethyl-3-[(4-methoxyphenyl)carbonyl]imidazo[1,2-a]pyrimidine To a 250-mL round-bottom flask was added a solution of pyrimidin-2-amine (950 mg, 9.99 mmol, 1.00 eq.), 1-(4-methoxyphenyl)pentane-1,3-dione (2.47 g, 11.98 mmol, 1.20 eq.) in THF (60 mL) at 0° C., and then (diacetoxyiodo)benzene (3.86 g, 11.98 mmol, 1.20 eq.), and BF3.Et2O (280 mg, 2.00 mmol, 0.20 eq.) were added. The resulting solution was stirred for 15 h at room temperature. The reaction was then quenched with 30 mL of water. The pH value of the mixture was adjusted to 7 with NaHCO$_3$ (aq.). The resulting solution was extracted with ethyl acetate (100 mL×3), and the organic phases were combined and dried over anhydrous sodium sulfate. The crude product was purified by Flash Prep-HPLC with the following conditions (CombiFlash-1): Column, silica gel; mobile phase, PE/EA=100/1 increasing to PE/EA=10/1 within 30 min. This resulted in 1.4 g of 2-ethyl-3-[(4-methoxyphenyl)carbonyl]imidazo[1,2-a]pyrimidine (50%) in the form of a brown solid. ESI-MS (EI$^+$, m/z): 282, 0.954 min

Step 2: Synthesis of 4-([2-ethylimidazo[1,2-a]pyrimidin-3-yl]carbonyl)phenol To a 60-mL sealed tube was added a solution of Compound 2 (1300 mg, 4.26 mmol, 1.00 eq.) in DCM (20 mL), and then BBr$_3$ (18 nil, 18 mmol, 4.00 eq.) was added. The reaction solution was stirred for 6 h at 50° C. The reaction was then quenched with 30 mL of ice water, and the pH value of the mixture was adjusted to 7 with NaHCO$_3$. The resulting solution was extracted with ethyl acetate (100 mL×3), and the organic phases were combined and dried over anhydrous sodium sulfate. This resulted in 1 g of 4-([2-ethylimidazo[1,2-a]pyrimidin-3-yl]carbonyl)phenol (81%) in the form of a white solid. ESI-MS (EI$^+$, m/z): 268, 0.816 min.

Step 3: Synthesis of 2,6-dibromo-4-([2-ethylimidazo[1,2-a]pyrimidin-3-yl]carbonyl)phenol To a 20-mL sealed tube was added a solution of 4-([2-ethylimidazo[1,2-a]pyrimidin-3-yl]carbonyl)phenol (130 mg, 0.49 mmol, 1.00 eq.) in DCM (10 mL), and then Br$_2$ (180 mg, 1.13 mmol, 2.20 eq.) was added. The resulting solution was stirred for 120 min at room temperature and then concentrated under vacuum. The crude product was purified by Prep-HPLC with the following conditions: Column: XBridge Prep C18 OBD Column, 5 um, 19×150 mm; Mobile Phase A: Water (0.1% FA), Mobile Phase B: CAN; Flow rate: 20 mL/min; Gradient: 36% B to 37% B in 7 min; 254, 220 nm; Rt: 5.82 min. This resulted in 22.8 mg of 2,6-dibromo-4-([2-ethylimidazo[1,2-a]pyrimidin-3-yl]carbonyl)phenol (11%). ESI-MS (EI$^+$, m/z): 426, 2.497 min. δ H (300 MHz, DMSO-d6) 1.20 (3H, t), 2.51 (3H, d), 7.31 (1H, dd), 7.90 (2H, s), 8.77 (1H, dd), 9.41 (1H, dd).

Example 21: Synthesis of (7-chloro-2-ethylimidazo[1,2-f]pyrimidin-3-yl)(3,5-dibromo-4-hydroxyphenyl)methanone

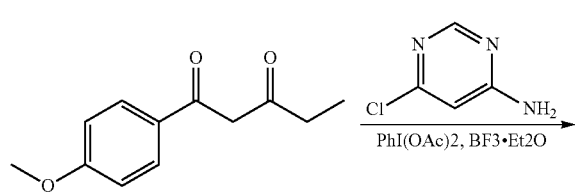

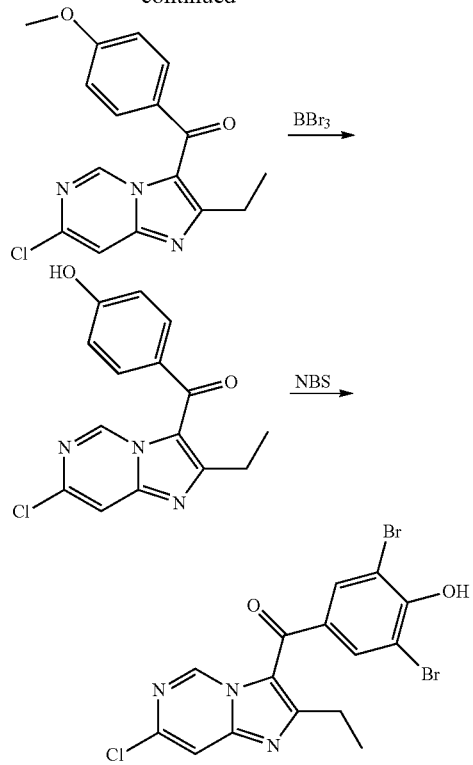

Step 1: Synthesis of (7-chloro-2-ethylimidazo[1,2-f]pyrimidin-3-yl)(4-methoxyphenyl) methanone Boron trifluoride etherate (0.280 g, 1.94 mmol) was added to a solution of (diacetoxyiodo) benzene (3.74 g, 11.65 mmol), 1-(4-methoxyphenyl)pentane-1,3-dione (2 g, 9.71 mmol) and 6-chloropyrimidin-4-amine (1.5 g, 11.65 mmol) in THF (4 mL) at 0° C. under nitrogen atmosphere. The resulting mixture was stirred overnight at room temperature. The reaction mixture was evaporated to dryness and redissolved in EtOAc (25 mL), and washed sequentially with saturated brine (25 mL×3). The organic phases were dried over Na$_2$SO$_4$, filtered and evaporated to give a crude product. The residue was purified by Prep-TLC (EtOAc: petroleum ether=1:2) to give (7-chloro-2-ethylimidazo[1,2-f]pyrimidin-3-yl)(4-methoxyphenyl) methanone (0.350 g, 11.4%) in the form of a yellow solid. m/z (ES$^+$), [M+H]$^+$= 316; base, HPLC Rt=1.124 min. $^1$H NMR (300 MHz, Chloroform-d) δ 10.67 (s, 1H), 7.97 (s, 1H), 7.74 (d, J=7.4 Hz, 1H), 7.31 (s, 1H), 7.18-7.06 (m, 1H), 6.34 (d, J=17.0 Hz, 1H), 6.12 (dd, J=17.0, 10.2 Hz, 1H), 5.66 (d, J=10.3 Hz, 1H), 1.39 (s, 12H).

Step 2: Synthesis of (7-chloro-2-ethylimidazo[1,2-f]pyrimidin-3-yl)(4-hydroxyphenyl) methanone A solution of boron tribromide in totuene (1.5 mL, 1 mol/L) was added to a solution of (7-chloro-2-ethylimidazo[1,2-f]pyrimidin-3-yl)(4-methoxyphenyl)methanone (150 mg, 0.43 mmol) in THF (5 mL) at 0° C. under nitrogen atmosphere. The reaction mixture was stirred at 50° C. for 14 h. The reaction mixture was evaporated to dryness and redissolved in EtOAc (25 mL), and washed sequentially with saturated brine (25 mL×3). The organic phases were dried over Na$_2$SO$_4$, filtered and evaporated to give a crude product. The residue was purified by Prep-TLC (EtOAc: petroleum ether=1:1) to give (7-chloro-2-ethylimidazo[1,2-f]pyrimidin-3-yl) (4-hydroxyphenyl)methanone (120 mg, 83.3%) in the form of a yellow solid. m/z (ES+), [M+H]+= 302; base, HPLC Rt=1.286 min. $^1$H NMR (300 MHz, Chloroform-d) δ 9.68 (d, J=1.3 Hz, 1H), 7.68-7.44 (m, 3H), 6.85 (dd, J=9.0, 2.3 Hz, 2H), 2.54 (q, J=7.5 Hz, 2H), 1.18-1.12 (m, 3H).

Step 3: Synthesis of (7-chloro-2-ethylimidazo[1,2-f]pyrimidin-3-yl)(3,5-dibromo-4-hydroxyphenyl)methanone NBS (120 mg, 0.66 mmol) was added to a solution of (7-chloro-2-ethylimidazo[1,2-f]pyrimidin-3-yl)(4-hydroxyphenyl)methanone (100 mg, 0.33 mmol) in MeCN (10 mL) under nitrogen atmosphere. The resulting mixture was stirred at room temperature for 2 h. The crude product was purified by Prep-HPLC (Column: Xselect CSH OBD Column, 30×150 mm, 5 um; Mobile Phase A: Water (0.1% FA), Mobile Phase B: CAN; Flow rate: 60 mL/min; Gradient: 47% B to 57% B in 7 min; 254; 220 nm; Rt: 7.12 min). Fractions containing the desired compound were evaporated to dryness to give (7-chloro-2-ethylimidazo[1,2-f]pyrimidin-3-yl) (3,5-dibromo-4-hydroxyphenyl)methanone (25.2 mg, 16.4%). m/z (ES+), [M+H]+=460; acid, HPLC Rt=1.548 min. $^1$H NMR (300 MHz, DMSO-d6) δ 11.06 (d, J=1.3 Hz, 1H), δ 9.61 (d, J=1.3 Hz, 1H), 8.02 (d, J=1.3 Hz, 1H), 7.89 (s, 2H), 2.44 (t, J=7.5 Hz, 2H), 1.17 (t, J=7.5 Hz, 3H).

Example 22: Synthesis of 3-bromo-5-(2-ethylimidazo[1,2-a]pyrimidine-3-carbonyl)-2-hydroxybenzonitrile

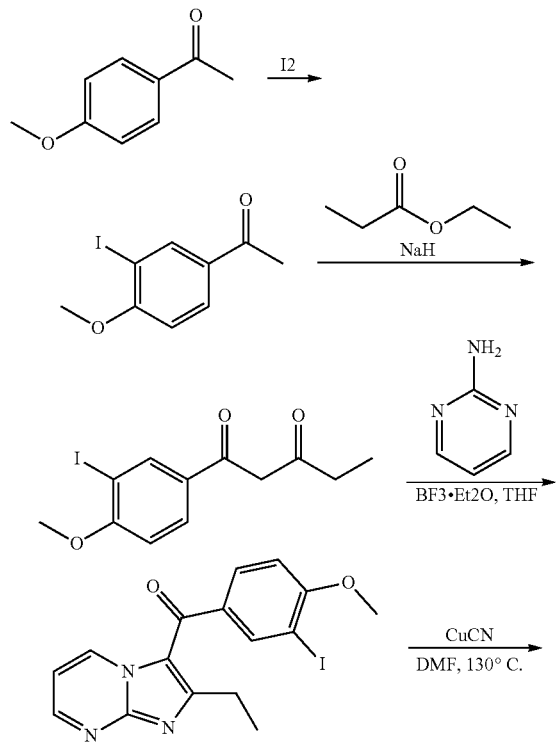

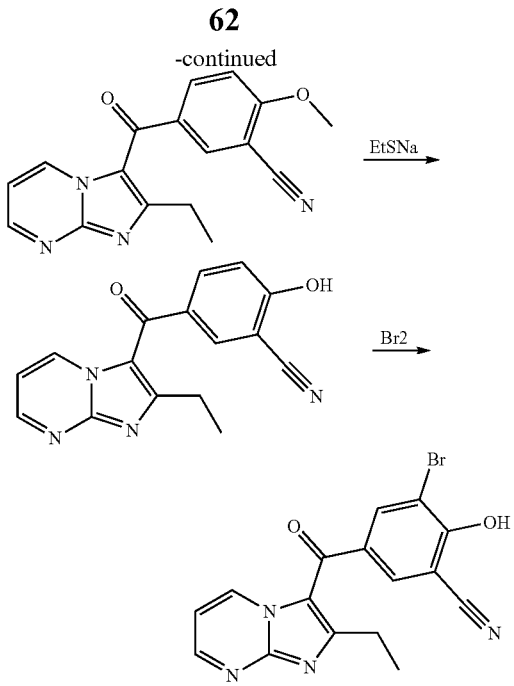

Step 1: Synthesis of 1-(3-iodo-4-methoxyphenyl)ethanone

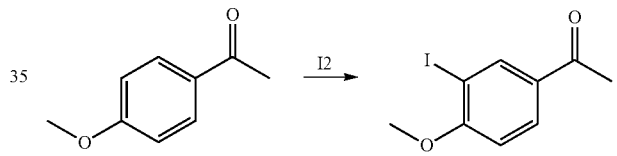

1-(3-iodo-4-methoxyphenyl)ethanone was synthesized according to the method in Step 1 of Example 10.

Step 2: Synthesis of 1-(3-iodo-4-methoxyphenyl)pentane-1,3-dione

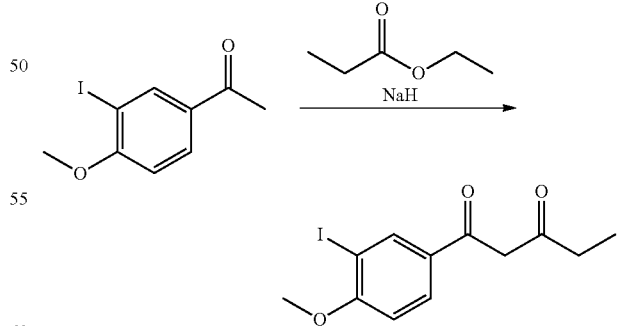

To a 100-mL sealed tube was added a solution of 1-(3-iodo-4-methoxyphenyl)ethanone (15 g, 100 mmol, 1 eq.) in DMF (100 mL). The mixture was stirred in an ice bath. NaH (7.87 g, 199.9 mmol, 2 eq.) was added at 0° C. The resulting solution was stirred at 0° C. for 2 h and then ethyl propionate (10.2 g, 100 mmol, 1 eq.) was added. The reaction mixture was stirred at room temperature overnight. The reaction was quenched with water (50 mL) and ethyl acetate was added for extraction. The organic phases were dried and concentrated to give a crude product, which was purified by silica gel column (petroleum ether:ethyl acetate=5:1, Rf=0.55) to give 1-(3-iodo-4-methoxyphenyl)pentane-1,3-dione (3.44 g, 19%).

Step 3: Synthesis of (2-ethylimidazo[1,2-a]pyrimidin-3-yl)(3-iodo-4-methoxyphenyl)methanone

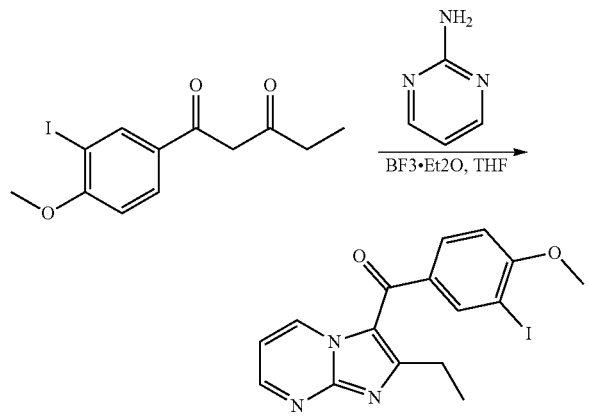

To a solution of 1-(3-iodo-4-methoxyphenyl)pentane-1,3-dione (3.8 g, 16.4 mmol, 1 eq.) and pyrimidin-2-amine (1.4 g, 14.8 mmol, 0.9 eq.) in THF (30 mL) was added (diacetoxyiodo) benzene (4.67 g, 16.4 mmol, 1 eq.) followed by BF$_3$.Et$_2$O (465 mg, 3.28 mmol, 0.2 eq.) at 0° C. The reaction mixture was stirred at room temperature overnight. The mixture was basified by NaHCO$_3$ (aq.) and extracted with ethyl acetate. The organic phases were dried and concentrated to give a crude product. The crude product was purified by silica gel column (petroleum ether:ethyl acetate=2:1, Rf=0.45) to give (2-ethylimidazo[1,2-a]pyrimidin-3-yl)(3-iodo-4-methoxyphenyl)methanone (1.66 g, 36%). $^1$H NMR (300 MHz, DMSO-d6) δ 1.17 (dt, J=9.9, 7.5 Hz, 3H), 2.49 (d, J=7.7 Hz, 2H), 3.83-4.01 (m, 3H), 7.12 (d, J=8.8 Hz, 1H), 7.31 (dt, J=6.9, 4.0 Hz, 1H), 8.21 (d, J=4.8 Hz, 2H), 8.76 (tt, J=4.8, 2.4 Hz, 1H), 9.44 (dd, J=6.9, 1.9 Hz, 1H). ESI-MS (EI$^+$, m/z): 408, 0.927 min.

Step 4: Synthesis of 5-(2-ethylimidazo[1,2-a]pyrimidine-3-carbonyl)-2-methoxybenzonitrile

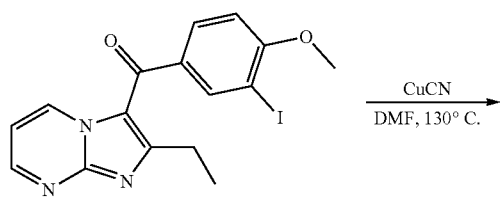

A solution of (2-ethylimidazo[1,2-a]pyrimidin-3-yl)(3-iodo-4-methoxyphenyl)methanone (1.66 g, 4 mmol, 1 eq.) and CuCN (0.725 g, 8 mmol, 2 eq.) in DMF (10 mL) was stirred at 130° C. for 2 h. The reaction mixture was cooled and filtered through celite. The filtrate was added to water and a green solid was formed. The solid was washed with water and crystallized in acetonitrile to give 5-(2-ethylimidazo[1,2-a]pyrimidine-3-carbonyl)-2-methoxybenzonitrile (280 mg, 22.4%) in the form of a yellow solid. ESI-MS (EI$^+$, m/z): 408, 0.927 min.

Step 5: Synthesis of 5-(2-ethylimidazo[1,2-a]pyrimidine-3-carbonyl)-2-hydroxybenzonitrile

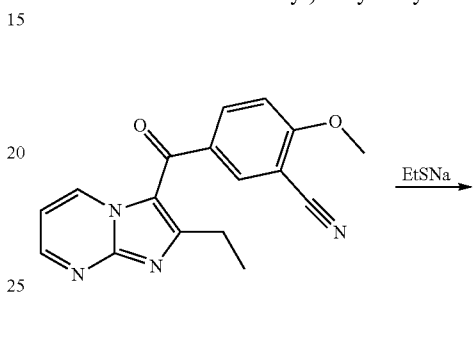

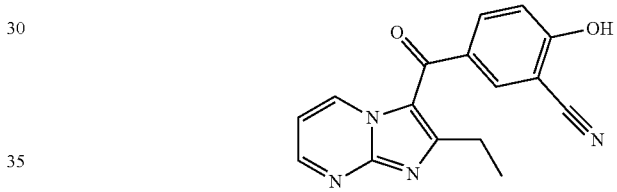

A solution of 5-(2-ethylimidazo[1,2-a]pyrimidine-3-carbonyl)-2-methoxybenzonitrile (180 mg, 0.59 mmol, 1 eq.) and NaSEt (1.76 mmol, 3 eq.) in DMF (5 mL) was stirred at 100° C. for 2 h. The reaction was complete based on LCMS. The mixture was cooled to room temperature and treated with H$_2$O (5 mL). The mixture was filtered and the filter cake was washed with water. The solid was dried and crystallized in acetonitrile to give 5-(2-ethylimidazo[1,2-a]pyrimidine-3-carbonyl)-2-hydroxybenzonitrile (150 mg, 41%). $^1$H NMR (400 MHz, DMSO-d6) δ 1.17 (t, J=7.5 Hz, 3H), 2.53-2.70 (m, 2H), 7.27-7.43 (m, 2H), 7.86 (dd, J=8.8, 2.2 Hz, 1H), 7.93-8.12 (m, 1H), 8.77 (dd, J=4.2, 2.0 Hz, 1H), 9.41 (dd, J=6.9, 2.0 Hz, 1H). ESI-MS (EI$^+$, m/z): 293, 0.794 min.

Step 6: Synthesis of 3-bromo-5-(2-ethylimidazo[1,2-a]pyrimidine-3-carbonyl)-2-hydroxybenzonitrile

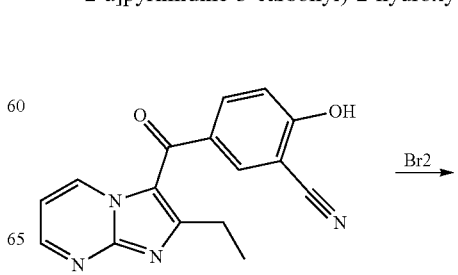

65

-continued

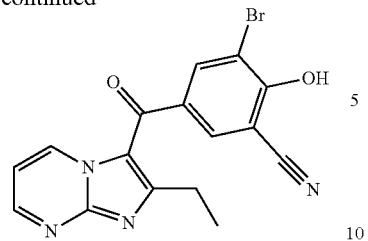

To a solution of 5-(2-ethylimidazo[1,2-a]pyrimidine-3-carbonyl)-2-hydroxybenzonitrile (150 mg, 0.51 mmol, 1 eq.) in AcOH (2 mL) was added a solution of Br₂ (120 mg, 0.75 mmol, 1.5 eq.) in AcOH (0.2 mL). The resulting mixture was stirred at room temperature for 1 h. The reaction was complete based on LCMS. The mixture was concentrated and crystallized in acetonitrile. The solid was purified by Prep-HPLC (Column: XSelect CSH Prep C18 OBD Column, 19×250 mm, 5 um; Mobile Phase A: Water (0.1% FA), Mobile Phase B: CAN; Flow rate: 25 mL/min; Gradient: 25% B to 84% B in 7 min; 254/220 nm; Rt: 6.5 min) to give 3-bromo-5-(2-ethylimidazo[1,2-a]pyrimidine-3-carbonyl)-2-hydroxybenzonitrile (16.3 mg, 8.57%). $^1$H NMR (300 MHz, DMSO-d6) δ 1.21 (t, J=7.5 Hz, 3H), 7.17-7.47 (m, 1H), 8.02 (s, 1H), 8.15 (d, J=2.0 Hz, 1H), 8.81 (s, 1H), 9.41 (d, J=7.0 Hz, 1H). ESI-MS (EI⁺, m/z): 371/373, 0.887 min.

Example 23: Synthesis of (3-bromo-4-hydroxy-5-(trifluoromethyl)phenyl)(2-ethylimidazo[1,2-a]pyrimidin-3-yl)methanone

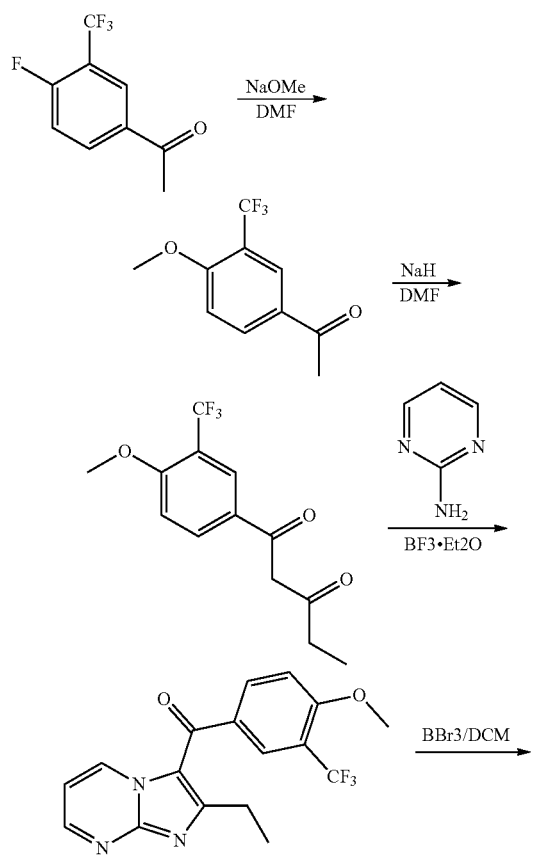

66

-continued

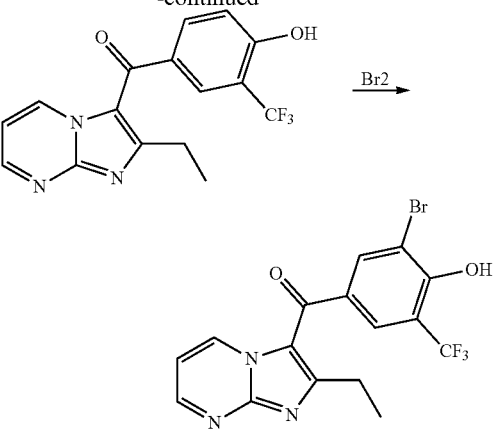

Step 1: Synthesis of 1-(4-methoxy-3-(trifluoromethyl)phenyl)ethanone

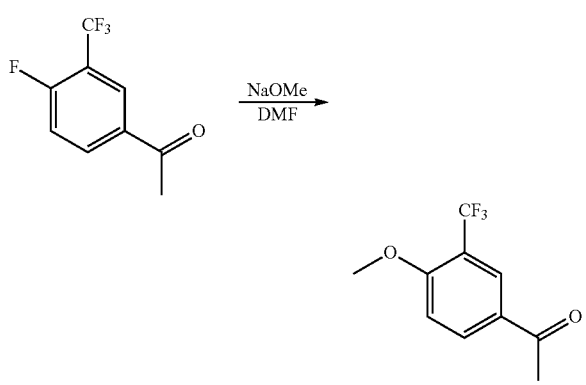

To a solution of 1-(4-fluoro-3-(trifluoromethyl)phenyl)ethanone (10 g, 48.5 mmol, 1 eq.) in DMF (100 mL) was added NaOMe (3.14 g, 58.2 mmol, 1.2 eq.) at 0° C. After the addition, the reaction mixture was stirred at room temperature for 1 h until the reaction was complete. The reaction was quenched with NH₄Cl (aq.) and the reaction mixture was extracted with ethyl acetate. The organic phases were washed with saturate brine and dried over anhydrous sodium sulfate. The solvent was removed under reduced pressure to give 1-(4-methoxy-3-(trifluoromethyl)phenyl)ethanone (15 g, crude product), which was used in the next step without further purification. $^1$H NMR (300 MHz, Chloroform-d) δ 2.59 (s, 3H), 3.98 (s, 3H), 7.06 (d, J=8.7 Hz, 1H), 8.01 (s, 1H), 8.14 (dd, J=8.7, 2.1 Hz, 1H).

Step 2: Synthesis of 1-(4-methoxy-3-(trifluoromethyl)phenyl)pentane-1,3-dione

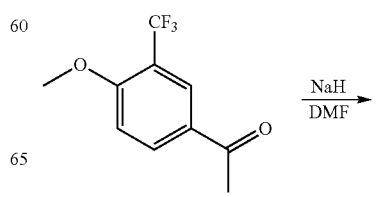

-continued

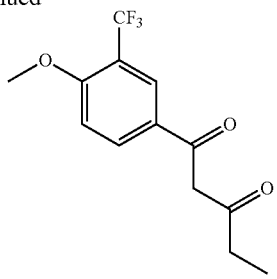

To a 100-mL sealed tube was added a solution of 1-(4-methoxy-3-(trifluoromethyl)phenyl) ethanone (4 g, 18.3 mmol, 1 eq.) in DMF (50 mL). The mixture was stirred in an ice bath. NaH (1.46 g, 36.6 mmol, 2 eq.) was added at 0° C. The resulting solution was stirred at 0° C. for 2 h and then ethyl propionate (1.86 g, 18.3 mmol, 1 eq.) was added. The reaction mixture was stirred at room temperature overnight. The reaction was quenched with NH₄Cl (20 mL) and the reaction mixture was extracted with ethyl acetate. The organic phases were dried and concentrated to give a crude product, which was purified by silica gel column (petroleum ether:ethyl acetate=5:1, Rf=0.5) to give 1-(4-methoxy-3-(trifluoromethyl)phenyl)pentane-1,3-dione (3.4 g).

Step 3: Synthesis of (2-ethylimidazo[1,2-a]pyrimidin-3-yl)(4-methoxy-3-(trifluoromethyl)phenyl)methanone

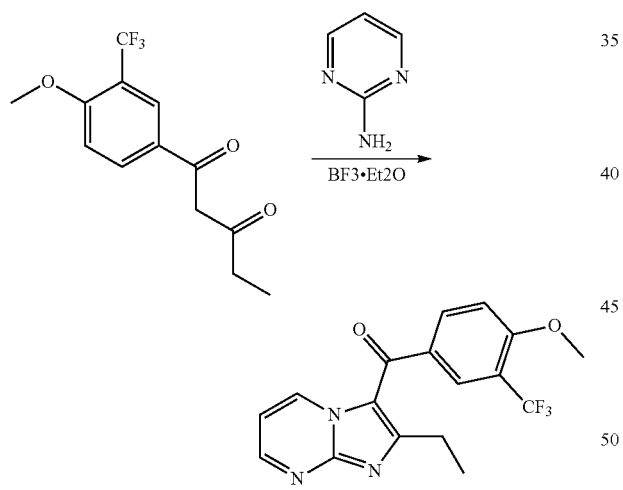

To a solution of 1-(4-methoxy-3-(trifluoromethyl)phenyl)pentane-1,3-dione (3.4 g, 12.4 mmol, 1 eq.) and pyrimidin-2-amine (1.0 g, 11.2 mmol, 0.9 eq.) in THF (30 mL) was added (diacetoxyiodo)benzene (3.53 g, 12.4 mmol, 1 eq.) followed by BF₃.Et₂O (352 mg, 2.48 mmol, 0.2 eq.) at 0° C. The reaction mixture was stirred at room temperature overnight. The mixture was basified by NaHCO₃ (aq.) and then extracted with ethyl acetate. The organic phases were dried and concentrated to give a crude product. The crude product was purified by silica gel column (petroleum ether:ethyl acetate=2:1, Rf=0.45) to give the (4-methoxy-3-(trifluoromethyl)phenyl)(2-ethylimidazo[1,2-a]pyrimidin-3-yl)methanone (420 mg, 9.8%). ¹H NMR (400 MHz, DMSO-d6) δ 1.15 (t, J=7.5 Hz, 3H), 2.43 (t, J=7.5 Hz, 2H), 4.02 (s, 3H), 7.32 (dd, J=6.9, 4.3 Hz, 1H), 7.46 (d, J=8.7 Hz, 1H), 7.97 (d, J=2.0 Hz, 1H), 8.05 (dd, J=8.7, 2.1 Hz, 1H), 8.69-8.85 (m, 1H), 9.40-9.51 (m, 1H). ESI-MS (EI⁺, m/z): 350, 0.796 min.

Step 4: Synthesis of (4-hydroxy-3-(trifluoromethyl)phenyl)(2-ethylimidazo[1,2-a]pyrimidin-3-yl)methanone

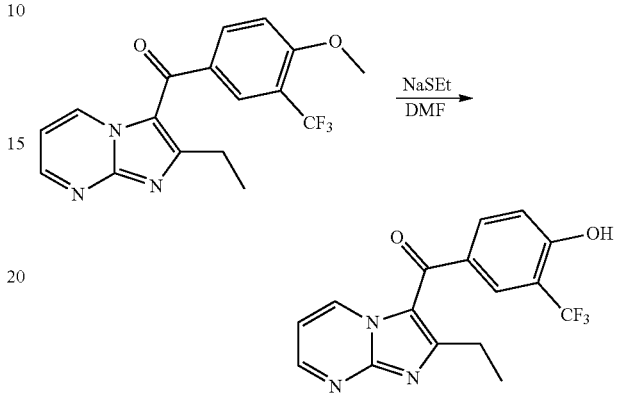

A solution of (4-methoxy-3-(trifluoromethyl)phenyl)(2-ethylimidazo[1,2-a]pyrimidin-3-yl) methanone (400 mg, 1.15 mmol, 1 eq.) and NaSEt (3.43 mmol, 3 eq.) in DMF (7 mL) was stirred at 100° C. for 2 h. The reaction was complete based on LCMS. The reaction mixture was cooled to room temperature and treated with water (10 mL). The reaction mixture was filtered and the filter cake was washed with water. The solid was purified by C18 flash column to give (4-hydroxy-3-(trifluoromethyl)phenyl)(2-ethylimidazo[1,2-a]pyrimidin-3-yl)methanone (110 mg, 28.7%). ¹H NMR (400 MHz, DMSO-d6) δ 1.14-1.31 (m, 3H), 2.66 (q, J=7.5 Hz, 2H), 6.13 (d, J=9.2 Hz, 1H), 7.12 (dd, J=6.8, 4.2 Hz, 1H), 7.48 (dd, J=9.2, 2.6 Hz, 1H), 7.64 (d, J=2.5 Hz, 1H), 8.60 (dd, J=4.2, 2.0 Hz, 1H), 9.02-9.10 (m, 1H). ESI-MS (EI⁺, m/z): 336, 0.927 min.

Step 5: Synthesis of (3-bromo-4-hydroxy-5-(trifluoromethyl)phenyl)(2-ethylimidazo[1,2-a]pyrimidin-3-yl)methanone

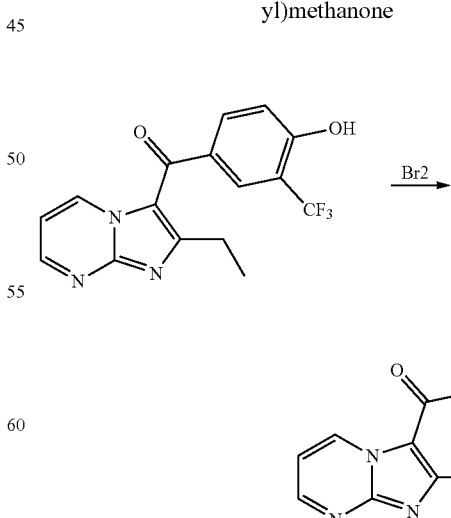

A solution of (4-hydroxy-3-(trifluoromethyl)phenyl)(2-ethylimidazo[1,2-a]pyrimidin-3-yl) methanone (110 mg, 0.33 mmol, 1 eq.) in AcOH (2 mL) was added to a solution of $Br_2$ (78.8 mg, 0.49 mmol, 1.5 eq.) in AcOH (0.2 mL). The reaction mixture was stirred at room temperature for 1 h. The reaction was complete based on LCMS. The mixture was concentrated and purified by Prep-HPLC (Column: SunFire Prep C18 OBD Column, 100 Å, 5 μm, 19 mm×250 mm; Mobile Phase A: Water (0.1% FA), Mobile Phase B: ACN; Flow rate: 25 mL/min; Gradient: 50% B to 50% B in 7 min; 254/220 nm; Rt: 6.3 min) to give (3-bromo-4-hydroxy-5-(trifluoromethyl)phenyl)(2-ethylimidazo[1,2-a]pyrimidin-3-yl)methanone (3.2 mg). $^1H$ NMR (300 MHz, DMSO-d6) δ 1.20 (t, J=7.5 Hz, 2H), 2.47 (d, J=7.4 Hz, 2H), 7.29 (dd, J=6.9, 4.2 Hz, 1H), 7.86 (s, 1H), 8.13 (d, J=4.7 Hz, 1H), 8.76 (dd, J=4.2, 2.0 Hz, 1H), 9.36 (d, J=6.8 Hz, 1H). ESI-MS ($EI^+$, m/z): 416, 1.151 min.

Example 24: Inhibition Test of the Compounds on hURAT1 in HEK293-Transfected Cells 1. Cell Culture and Inoculation 1) HEK-293T cells stably expressing hURAT1 were cultivated in culture medium (DMEM medium+10% fetal bovine serum+G418 (500 μg/mL)+1% P/S).

2) When the cells covered 80% of the culture medium, the culture medium was removed. The cells were washed with PBS once, followed by digestion with pancreatin-EDTA. After detachment, the cells were added with a culture medium, exfoliated by pipetting, and centrifuged for harvesting. The harvested cells were added with a culture medium and mixed well to give a cell suspension.

3) The cell density was adjusted to $3×10^5$ cells/mL, transferred into a white-wall, clear-bottom, 96-well cell culture plate with 100 μL/well, and incubated for 12-24 h.

2. Compound Preparation

1) A 20 mM stock solution of the compound was prepared with DMSO. Then the stock solution was diluted to a starting concentration of 2 mM with DMSO.

2) The solution was serially 4-fold diluted with DMSO from 2 nM to the 10th concentration on a 96-well plate serving as the 100× plate, and respective quality controls were prepared.

3) The solutions in corresponding wells were 10-fold diluted with Cl-free HBSS buffer on another 96-well plate serving as the 10× plate.

4) Buffer containing 0.1 μCi/mL $^{14}C$-uric acid, at 45 μL/well, and a 10× diluted compound, at 5 μL/well, were added to a third 96-well plate serving as the 1× plate for later use. The concentration of DMSO was 1%.

3. Uptake of $^{14}C$-Uric Acid in Cells Stably Expressing hURAT1

1) The uptake assay was performed after the cultivated cells in 96-well plates adhered.

2) The cells were washed once with pre-heated buffer at 200 μL/well.

3) After the wells were dried, corresponding compounds (50 μL/well) and 0.1 μCi/mL $^{14}C$-uric acid were immediately added.

4) The plate with the compound was incubated in a 37° C. incubator for 5 min.

5) 150 μL of ice-cold buffer was added to each well to terminate the uptake. Each well was washed three times with buffer. The cells were carefully washed to avoid detachment.

6) 50 μL of lysis buffer was added to each well, prior to shaking at 900 rpm on an oscillator for 5 min.

7) 150 μL of scintillation solution (Microint 40) was added to each well before shaking at 900 rpm for 5 min.

8) Finally, the microwell plate was transferred to a Micro-Beta Trilux (PerkinElmer Co. Ltd.) for detection.

4. Data Processing

The data were analyzed and the $IC_{50}$ of the quality controls and all test compounds on the plates were calculated using XL-fit software. See table 1 for the results.

Experimental results showed that these compounds have a good inhibitory effect on uric acid transferring by hURAT1 in transfected HEK293 cells, and the inhibitory effects of most compounds are superior to that of benzbromarone.

Example 25: Inhibition Assay of the Compounds on OAT1/OAT3 Targets in HEK293-Transfected Cells 1. Reagents and Consumables

| Reagent/consumable | Supplier | Catalog number |
|---|---|---|
| HEK293/OAT1 | HDB | |
| HEK293/OAT3 | HDB | |
| DMEM | Invitrogen | 10566-024 |
| FBS | Biowest | S1810-500 |
| 100x Pen/Strep | Gibco | 15140-122 |
| Hygromycin B | CABIOCHEM | 400052 |
| DMSO | Sigma | D8418 |
| DPBS | Sigma | D8537 |
| Trypsin | Invitrogen | 25200-056 |
| MatriGel ® Matrix | BD Bioscience | 354230 |
| 1M HEPES | Gibco | 15630-080 |
| 1x HBSS | Gibco | 14065 |
| 6-carboxyfluorescein | Sigma | C0662 |
| Probenecid | Sigma | P8761 |
| Benzbromarone | MCE | HY-B1135 |
| 100 mm dish | Corning | 430167 |
| Cell counter | Invitrogen | C10227 |
| ECHO LDV plate | LabCYTE | LP-0200 |
| 384-well plate | Costar | 3656 |
| 384-well plate (black/clear-bottom) | Costar | 3712 |
| Liquids instrument Bravo | Agilent | |
| Envision multifunctional plate reader | PerkinElmer | |
| Multidrop Combi reagent dispenser | Thermo | |
| Pipette | Thermo Fisher | |

2. Culture Media and Solutions

Thaw medium: 90% DMEM+10% FBS+1× Pen/Strep, preserved at 4° C. for later use.

Culture medium: 90% DMEM+10% FBS+1× Pen/Strep+100 μg/mL Hygromycin B, preserved at 4° C. for later use.

5× Matrigel: 1 vial of Matrigel was thawed overnight at 4° C., then diluted to 500 mL with cold DMEM. The resulting solution was preserved at 4° C. for later use after subpackaging.

Uptake assay buffer: 487.5 mL HBSS buffer was mixed with 12.5 mL 1M HEPES, with the final HEPES concentration being 25 mM. This was prepared right before the experiment.

30 mM probenecid: 2 mg of the powder was dissolved in 233.62 μL of 100% DMSO. The resulting solution was preserved at −20° C. for later use after subpackaging.

30 mM benzbromarone: 2 mg of the powder was dissolved in 157.20 μL of 100% DMSO. The resulting solution was preserved at −20° C. for later use after subpackaging.

1 mM 6-carboxyfluorescein (molecular weight: 376.32): 0.3763 mg of the powder was dissolved in 1 mL of uptake assay buffer. The resulting solution was preserved away from light at 4° C. for later use after subpackaging.

3. Instruments

Envision multimode plate reader (with parameters as follows)

Required filters:
Excitation wavelength: 485 nm
Emission wavelength: 590 nm
Excitation cutoff filter: 505 nm 4. Experimental Procedures 5.1 Cell Culture 1) Thawing The cells were quickly taken out from a liquid nitrogen tank and shaken in a water bath at 37° C. until completely thawed. The cell suspension was quickly added to a pre-heated culture medium and centrifuged at 1000 rpm for 5 min. The supernatant was discarded. A fresh pre-heated culture medium was added for resuspension. The cell suspension was transferred into a 100 mm dish and incubated at 37° C. at 5% $CO_2$.

2) Passage

When covering the dish by 80-90%, the cells were digested with 0.25% Trypsin-EDTA and resuspended using a new culture medium. Typically, the cells were passaged every 2-3 days in a ratio of 1:3 to 1:5.

5.2 Experiments

Day 1: Plating

1) Coating

5× Matrigel was added to a 384-well cell plate at 5 μL/well for incubation in an incubator at 37° C. for 30 min, followed by digestion.

2) Plating

Cells were collected after digestion, counted, resuspended at $1 \times 10^6$ cells/mL using a culture medium, and added to a coated plate at 60 μL/well by using a Multidrop Combi to give a cell density of $6 \times 10^4$ cells/well, followed by incubating overnight at 37° C. at 5% $CO_2$.

Day 2: Reaction Assay

3) Preparation of Uptake Assay Buffer

On the day of experiment, fresh buffer was prepared as needed.

4) Preparation of Compounds (Using ECHO)

Working solutions of 11 concentrations were prepared for plotting a curve with stock solutions of 3 concentrations using PlateMap. The 3 concentrations were 30 mM, 0.3 mM, 0.003 mM, all formulated in DMSO. Details of ECHO are given in the table below:

| Stock solution (mM) | Transferred volume (nL) | Added DMSO (nL) | Final volume (μL) | Working concentration (μM) | Final concentration (μM) |
|---|---|---|---|---|---|
| 30 | 600 | 0 | 30 | 600 | 300.1000 |
|  | 200.0 | 400 | 30 | 200 | 100.5000 |
|  | 67.5 | 532.5 | 30 | 67.50 | 33.0900 |
|  | 22.50 | 577.5 | 30 | 22.50 | 11.0300 |
|  | 7.50 | 592.5 | 30 | 7.5 | 3.6765 |
| 0.3 | 245.00 | 355 | 30 | 2.450 | 1.2375 |
|  | 82.50 | 517.5 | 30 | 0.825 | 0.4167 |
|  | 27.50 | 572.5 | 30 | 0.275 | 0.1348 |
|  | 10.00 | 590 | 30 | 0.1000 | 0.0490 |
| 0.003 | 302.50 | 297.5 | 30 | 0.0303 | 0.0153 |
|  | 102.50 | 497.5 | 30 | 0.01025 | 0.0051 |

5) Preparation of a Mixed Solution of 6-Carboxyfluorescein (6 μM) and Compounds

According to amount used, 6-carboxyfluorescein (1 mM) was diluted with uptake assay buffer to give a diluted 6-carboxyfluorescein solution (6 μM). The diluted 6-carboxyfluorescein solution (6 μM) was added to a compound plate prepared by ECHO with Combi at 30 μL/well, to give a mixed solution of 6-carboxyfluorescein and compounds. The mixture was preserved away from light for later use. The concentration of DMSO was 2% at this time.

6) Plate Washing

The cells were incubated overnight before the culture medium was carefully removed. Then 80 μL of uptake assay buffer was added to each well at room temperature for washing the cells 3 times. After washing, 20 μL of uptake assay buffer was added to each well.

7) Adding Compound

The mixed solution of 6-CF (6 μM) and compounds, prepared in step 5, was transferred to a cell plate at 20 μL/well with Bravo. The mixed solution was centrifuged at 400 rpm for 1 min, and incubated away from light at room temperature for 10 min. At this time, the concentration of 6-CF became 3 μM, the concentration of the compound became the final concentration, and the concentration of DMSO became 1%.

8) Plate Washing

The cells were washed 3 times with pre-cooled uptake assay buffer at 80 μL/well, to remove unbound 6-CF.

9) Plate Reading

The plate was read on the Envision. The data were recorded and processed to calculate $IC_{50}$.

5.3 Data Analysis

According to the fluorescence signals of HPE and ZPE on each cell plate, the inhibition rate (%) of the compound in each well on the cell plate was calculated. HPE, which contained a high concentration of a positive compound (400 μM probenecid), served as the 100% inhibition control. ZPE, which contained no compound but the solvent DMSO (1% DMSO), served as a 0% inhibition control.

The calculation formula of the inhibition rate is as follows:

$$\text{Inhibition \%} = 100 - (I_{compound} - I_{HPE})/(I_{ZPE} - I_{HPE}) \times 100$$

The XLfit software was used to plot the curve for calculating the $IC_{50}$ values of the compounds. The $IC_{50}$ value of the positive compound was also one of the criteria for controlling the quality of each experiment. See table 1 for the results.

The results shows that most of the compounds have better selectivity to OAT1/3 than benzbromarone.

TABLE 1

| Compound | $IC_{50, hURAT1}$ | $IC_{50, OAT1}/IC_{50, hURAT1}$ | $IC_{50, OAT3}/IC_{50, hURAT1}$ |
|---|---|---|---|
| Benzbromarone | C | 10.3 | 2.4 |
| Example 1 | A | ND | ND |
| Example 3 | A | 13.8 | 8.9 |
| Example 4 | A | 55.0 | 36.5 |
| Example 5 | A | 34.4 | 21.1 |
| Example 6 | A | 33.6 | 24.8 |
| Example 7 | B | 14.2 | 3.0 |
| Example 8 | B | ND | ND |
| Example 9 | B | 7.6 | 2.0 |
| Example 14 | B | 3.5 | 3.6 |
| Example 16 | A | 17.4 | 3.1 |
| Example 18 | A | 24.5 | 16.2 |
| Example 20 | A | 8.0 | 8.7 |
| Example 21 | A | 3.8 | 5.5 |
| Example 22 | C | 2.0 | 1.4 |
| Example 23 | B | 5.2 | 10.3 |

A: $IC_{50}$ < 50 nM; B: 50 < $IC_{50}$ < 200 nM; C: 200 < $IC_{50}$ < 500 nM

Example 26: Cytotoxicity Assay of Compounds on Primary Human Hepatocytes

Materials and Sources:

Primary human hepatocytes were purchased from Biorecamation IVT. Co., Ltd. (lot no.: AKB/S1391); the components of in vitro culture media of primary human cell and suppliers are as follows:

| Reagent | Supplier | Catalog number | Volume |
|---|---|---|---|
| Williams E medium | Sigma | W1878 | 46 mL |
| glutaMAX | Gibco | 35050 | 500 µL |
| HEPES | Gibco | 15630-080 | 750 µL |
| ITS | Sigma | 13146 | 500 µL |
| dexamethasone | NICPBP | — | 0.5 µL |
| Penicillin/Streptomycin | Solarbio | P1400-100 | 500 µL |

Experimental Procedures

1. Frozen primary human hepatocytes were thawed, then resuspended in a culture medium containing 10% FBS. The cells were transferred into a 96-well plate, at $8 \times 10^4$ cells/well, followed by incubating overnight in an incubator at 5% $CO_2$ at 37° C.;

2. The test compounds and reference drug (benzbromarone) of different concentrations gradients were prepared using culture media containing 10% FBS. The test compounds and control drug were added to wells, at 100 µL/well, to form test compound wells or reference wells, and the culture medium containing 10% FBS was added to wells, at 100 µL/well, as negative control. The cells were incubated in an incubator in the presence of 5% $CO_2$ at 37° C. for 48 h.

3. The primary human hepatocytes were washed with PBS (0.1 M, pH=7.4) twice, and were added with CellTiter-Glo reagent at 100 µL/well. Cell-free wells added with CellTiter-Glo reagent at 100 µL/well served as the blank control. The 96-well plate was shaken on a shaker for 5 min, and then left at room temperature for 10 min.

4. The chemiluminescence values were detected using Victor X4 (Perkin Elmer). The chemiluminescence values of the test compound wells were denoted as $F_{(test\ compound)}$, the chemiluminescence values of the blank control wells were denoted as $F_{(blank)}$, and the chemiluminescence values of the negative control wells were denoted as $F_{(negative\ control)}$. The cell viabilities at different concentrations were calculated according to the following formula. Each concentration was measured in triplicate to give the average and the standard deviation.

$$\text{Cell viability (\%)} = \frac{F_{(test\ compound)} - F_{(blank\ control)}}{F_{(negative\ compound)} - F_{(blank\ control)}} \times 100\%$$

5. The half maximal inhibitory concentration ($IC_{50}$) of the test compounds to the primary human hepatocytes were calculated using Prism Graph software.

See Table 2 for the results. From the results, it can be seen that all the compounds have much lower inhibitory effect on the growth of primary human hepatocytes than benzbromarone, suggesting that they are much less toxic to the liver than benzbromarone.

TABLE 2

| Compound | $IC_{50}$, µM |
|---|---|
| Benzbromarone | 6.65 |
| Example 4 | 257.00 |
| Example 5 | 77.78 |
| Example 14 | 1000 |
| Example 21 | 347.00 |

Example 27: Evaluating the Inhibitory Effects of Compounds on CYP2C9 Enzyme

The assay was performed in 100 mM phosphate buffer in a total volume of 200 µL. The microsome concentration in the reaction system was 0.25 mg/mL, the concentrations of the test compounds were 10, 3.33, 1.11, 0.37, 0.12, 0.04 and 0 µM, the CYP2C9-specific probe substrate and the concentration were diclofenac (10 µM). The mixture was pre-incubated in a 37° C. thermostatic oscillator for 5 min, and a NADPH-generating system (containing 1.3 mM $NADP^+$, 3.3 mM D(+)-glucopyranose-6-phosphate, 0.4 U/L glucose-6-phosphate dehydrogenase, 3.3 mM $MgCl_2$) was added to start the reaction. After incubation for 10 min, the reaction was terminated by adding an equal volume of acetonitrile. The mixture was vortexed and centrifuged at 13,000 rpm. The resulting supernatant was loaded to LC-MS-MS to determine the content of metabolites. The metabolite of diclofenac specifically obtained by CYP2C9 metabolism pathway is 4-hydroxydiclofenac. Sulfaphenazole was adopted as a specific CYP2C9 inhibitor. In the experiment, analysis was performed by GraphPad Primsm 5.0 to calculate the half maximal inhibitory concentration ($IC_{50}$ value).

According to the method described above, the compounds of examples 4, 5, 14, 20 and 21 in the present invention show very low or no inhibitory effect on various CYP enzymes, with higher $IC_{50}$ than that of benzbromarone.

Example 28: Study on Metabolites of Compound in Human and Rat Hepatocyte Incubation System 1. Preparation of Stock and Working Solutions Stock solution: A proper amount of test sample powders was dissolved in DMSO or other proper solvents, and the mixture was well mixed to give a stock solution (10 mM). The stock solution was preserved in a refrigerator at 4° C. for later use.

Working solution: The 10 mM stock solution was diluted to 1 mM working solution using acetonitrile, and well mixed for later use.

2. Preparation of Thawing Medium I

Williams' Medium E, glutamate, HEPES, fetal bovine serum albumin, human recombinant insulin, dexamethasone, and cell separation medium (Percoll™) were mixed in a ratio of 700:10:15:50:1:0.1:300 for use.

3. Preparation of Terminating Solution

An acetonitrile solution containing 0.1% formic acid was prepared as the terminating solution and preserved in a refrigerator at 4° C. for use.

4. Isolation and Preparation of Hepatocyte Suspension

The cryopreserved hepatocytes were thawed in a water bath at 37° C. for about 90 s, and quickly poured into the pre-heated isolating buffer. Residual hepatocytes were washed using the isolating buffer. Cells were combined and mixed well, and centrifuged at room temperature for 5 min at 100×g. The supernatant was discarded and the cells were resuspended using pre-heated William' Medium E. 20 µL of hepatocyte suspension was added into 100 μL of 0.4% Trypan blue. The cells were counted, and a cell viability over 70% was required. The hepatocyte density was adjusted to 1.25×10⁶ cells/mL using William' Medium E.

5. Incubation and Treatment of Samples

1) The test compound working solution was pre-incubated (pre-heated) in a constant-temperature incubator at 37° C. for 10 min. 2 μL of the working solution (1 mM) was pipetted to a cell culture plate containing 160 μL of hepatocyte suspension at 1.25×10⁶ cells/mL, and the mixture was well mixed. 38 μL of Williams' Medium E was added. The mixture was well mixed and incubated in an incubator (in a total volume of 200 μL), and the timer was started. For the blank control, 40 μL of Williams' Medium E was added instead of the working solution. For 0-min samples, 400 μL of acetonitrile (containing 0.1% formic acid) was added, followed by the working solution and Williams' Medium E.

2) After 180 min of incubation, the samples were measured for the cell viability. Then 400 μL of acetonitrile (containing 0.1% formic acid) solution was added to terminate the reaction.

3) After the reaction was terminated, the plate was shaken on a shaker at 300 rpm for 10 min, followed by centrifugation at least 10000×g for at least 10 min. After centrifugation, the supernatant was all transferred to centrifuge tubes and dried with nitrogen.

4) The residues were re-dissolved in a suitable solvent, and centrifuged at least 10000×g for at least 15 min at room temperature. The supernatant was transferred to a sample analysis plate for LC-MS analysis.

5) The methodology for 7-ethoxycoumarin (30 μM) was the same as that of test samples. Samples of the test compounds after incubation were used for metabolite assay only when the target metabolite was detected in the positive control sample. Otherwise, the above experiment should be repeated.

6. Data Acquisition and Analysis

1) Data Acquisition

LC-MSn (n=1-2) analytical methods were established on the basis of UPLC-PDA (Waters)-Q-E Plus (Thermo) or Waters UPLC-PDA-Q/TOF, and data acquisition was performed on samples using different mass spectrometry scan modes (MSE and MS2) and ultraviolet full wavelength (190-500 nm).

2) Data Analysis

The collected mass spectrometric data was processed using MetaboLynx or Compound Discover. Potential metabolites were screened by setting appropriate parameters according to the chemical structure of the test compounds.

The data processed by the software was further screened for metabolites relevant to the test compounds.

The metabolites produced by each species of liver microsomes were analyzed comprehensively, and the relative percentage of the integral ultraviolet peak area for each metabolite was given.

The possible structures of the metabolites were presumed by comparative analysis of the test compounds (parent compound) and fragments of the metabolites.

According to the assays of rat and human hepatocyte metabolites, toxic metabolites of benzbromarone produced by in vivo metabolism was not observed in any test compounds of examples 4, 5, 14, 20 and 21.

Example 29: Pharmacokinetics

Methodology for pharmacokinetics of compounds in rats:

1. Male SD rats were acclimatized in the animal room for 7 days after arrival.

2. Six SD rats were randomized into 2 groups, with 3 animals in each group. One group was administered by oral gavage (p.o.), and the other group was treated via tail vein injection (i.v.). Rats in the p.o. group were deprived of food overnight before administration.

3. After administration, about 200 μL of blood was collected from the orbital venous plexus at various time points.

4. The collected blood samples were centrifuged at 12000 rpm for 5 min at 4° C., and then the upper plasma samples were collected and preserved in a refrigerator at −20° C.

5. The procedures were summarized as follows:

| Route of administration | I.V. | P.O. |
|---|---|---|
| Dose | 1 mg/kg | 10 mg/kg |
| Concentration | 0.5 mg/ml | 2 mg/ml |
| Dosing volume | 2 ml/kg | 5 ml/kg |
| Vehicle | 5% DMSO, 5% Solutol, 90% PBS | 0.5% methylcellulose |
| Testing animals | 3 SD rats per group | |
| Blood sampling time point | 0.08, 0.25, 0.5, 1, 2, 4, 8, 12, and 24 h | |

6. LC-MS/MS (UPLC-MS/MS: liquid chromatography Waters Acquity UPLC (USA) and mass spectrometry 5500 Q Trap (Applied Biosystem/MDS SCIEX) or HPLC-MS\MS: liquid chromatography Agilent 1200 series (USA) and mass spectrometry API 4000 (Applied Biosystem/MDS SCIEX)) were used to determine the concentration of the compound in the plasma.

The pharmacokinetic parameters were calculated using the pharmacokinetic software WinNonlin [Model: Phoenix™ WinNonlin® 6.1; Manufacturer: Pharsight Corporation]. [Phoenix 1.1 User's Guide: p 251-p 300]

According to the above methods, the compounds of examples 4, 5, 14, 20 and 21, which were assayed in the previous example, exhibit a good bioavailability (>30%).

The invention claimed is:

1. A compound or the tautomer thereof or the pharmaceutically acceptable salt thereof, selected from the group consisting of:

(3,5-dibromo-4-hydroxyphenyl)(2-ethyl-7-(trifluoromethyl)imidazo[1,2-a]pyrimidin-3-yl)methanone;

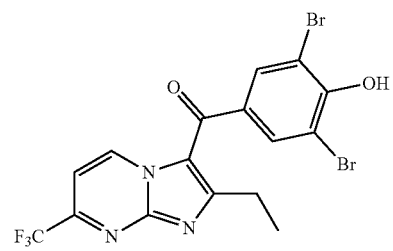

77

(6-bromo-2-ethylimidazo[1,2-a]pyrimidin-3-yl)(3,5-dibromo-4-hydroxyphenyl)methanone;

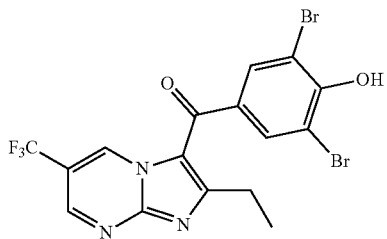 [SMILES: CCc1nc2ncc(C(F)(F)F)cn2c1C(=O)c1cc(Br)c(O)c(Br)c1]

(3,5-dibromo-4-hydroxyphenyl)(2-ethyl-6-fluoroimidazo[1,2-a]pyrimidin-3-yl)methanone;

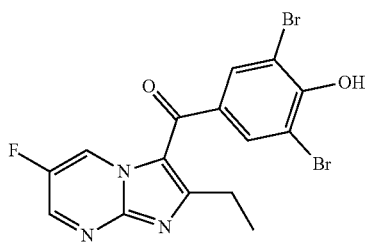

(3,5-dibromo-4-hydroxyphenyl)(2-ethyl-6-(trifluoromethyl)imidazo[1,2-a]pyrimidin-3-yl)methanone;

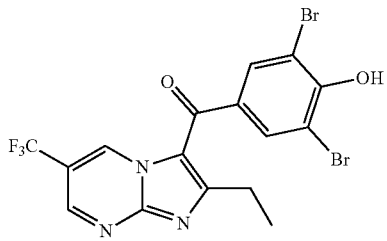 [SMILES: CCc1nc2ncc(C(F)(F)F)cn2c1C(=O)c1cc(Br)c(O)c(Br)c1]

(6-chloro-2-ethylimidazo[1,2-a]pyrimidin-3-yl)(3,5-dibromo-4-hydroxyphenyl)methanone;

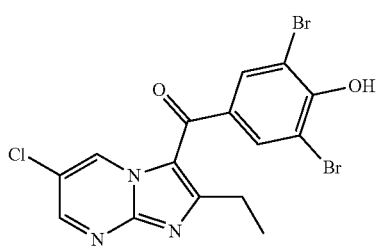 [SMILES: CCc1nc2ncc(Cl)cn2c1C(=O)c1cc(Br)c(O)c(Br)c1]

78

(3,5-dibromo-4-hydroxyphenyl)(2-ethyl-7-(trifluoromethyl)imidazo[1,2-c]pyrimidin-3-yl)methanone;

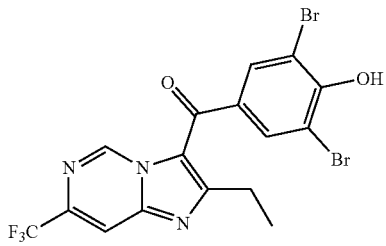 [SMILES: CCc1nc2cc(C(F)(F)F)ncn2c1C(=O)c1cc(Br)c(O)c(Br)c1]

3-bromo-5-(2-ethyl-6-(trifluoromethyl)imidazo[1,2-a]pyrimidin-3-carbonyl)-2-hydroxybenzonitrile;

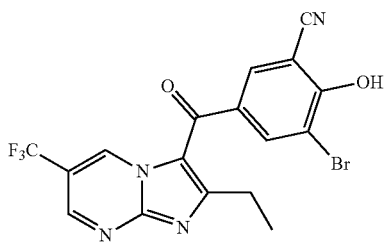 [SMILES: CCc1nc2ncc(C(F)(F)F)cn2c1C(=O)c1cc(Br)c(O)c(C#N)c1]

3-bromo-5-(2-ethyl-6-fluoroimidazo[1,2-a]pyrimidin-3-carbonyl)-2-hydroxybenzonitrile;

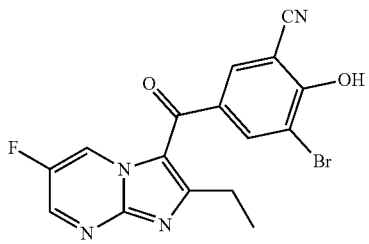 [SMILES: CCc1nc2ncc(F)cn2c1C(=O)c1cc(Br)c(O)c(C#N)c1]

5-(2-ethyl-6-fluoroimidazo[1,2-a]pyrimidine-3-carbonyl)-2-hydroxyisophthalonitrile 2,2,2-trifluoroacetate;

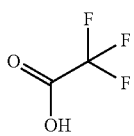
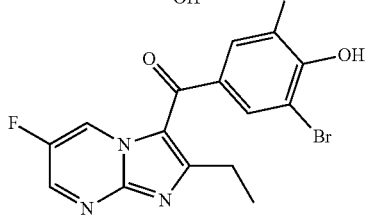

3-bromo-5-(2-ethyl-7-(trifluoromethyl)imidazo[1,2-a]pyrimidin-3-carbonyl)-2-hydroxybenzonitrile;

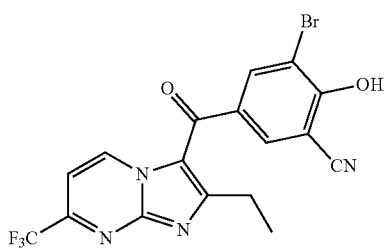 [SMILES: CCc1nc2nc(C(F)(F)F)ccn2c1C(=O)c1cc(Br)c(O)c(C#N)c1]

(3-bromo-4-hydroxy-5-(trifluoromethyl)phenyl)(2-ethyl-6-fluoroimidazo[1,2-a]pyrimidin-3-yl)methanone;

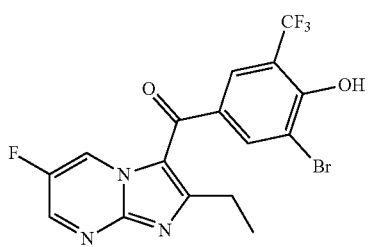 [SMILES: CCc1nc2ncc(F)cn2c1C(=O)c1cc(Br)c(O)c(C(F)(F)F)c1]

(3-bromo-4-hydroxy-5-(trifluoromethyl)phenyl)(2-ethyl-6-(trifluoromethyl)imidazo[1,2-a]pyrimidin-3-yl)methanone;

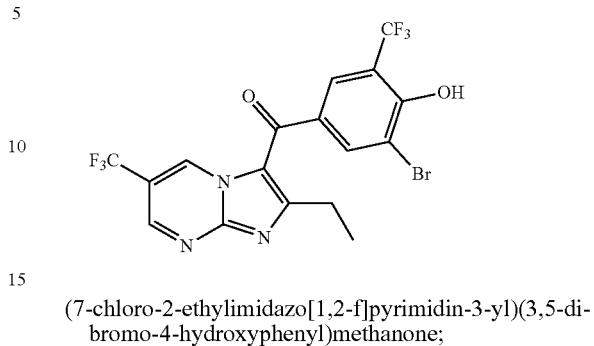

(7-chloro-2-ethylimidazo[1,2-f]pyrimidin-3-yl)(3,5-dibromo-4-hydroxyphenyl)methanone;

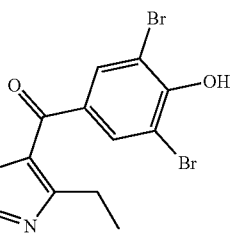

or tautomers or pharmaceutically acceptable salts thereof.

2. A pharmaceutical composition, comprising the compound according to claim 1, or the tautomer thereof or the pharmaceutically acceptable salt thereof, and a pharmaceutically acceptable carrier.

3. A method for preventing and/or treating hyperuricemia and gout comprising administering a prophylactic or therapeutic dosage of the pharmaceutical composition of claim 2 to a subject in need thereof.

* * * * *